United States Patent
Sakashita et al.

(10) Patent No.: US 8,592,118 B2
(45) Date of Patent: Nov. 26, 2013

(54) TONER, DEVELOPER, IMAGE FORMING APPARATUS, AND IMAGE FORMING METHOD

(75) Inventors: Shingo Sakashita, Shizuoka (JP); Kazumi Suzuki, Shizuoka (JP); Tatsuya Morita, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/456,659

(22) Filed: Apr. 26, 2012

(65) Prior Publication Data

US 2012/0288791 A1 Nov. 15, 2012

(30) Foreign Application Priority Data

May 11, 2011 (JP) ................. 2011-106418

(51) Int. Cl.
*G03G 9/087* (2006.01)
(52) U.S. Cl.
USPC ...................................... 430/108.4
(58) Field of Classification Search
USPC ............... 430/105, 109.4, 109.2, 137.18
See application file for complete search history.

(56) References Cited

U.S. PATENT DOCUMENTS

| | | | |
|---|---|---|---|
| 5,387,665 A * | 2/1995 | Misawa et al. | 528/81 |
| 2007/0015077 A1* | 1/2007 | Yamashita et al. | 430/109.4 |
| 2007/0160782 A1* | 7/2007 | Yatsuzuka et al. | 428/34.2 |
| 2010/0183967 A1 | 7/2010 | Sabu et al. | |
| 2010/0216068 A1 | 8/2010 | Kotsugai et al. | |
| 2010/0330489 A1 | 12/2010 | Inoue et al. | |
| 2011/0065036 A1 | 3/2011 | Inoue et al. | |
| 2011/0104608 A1 | 5/2011 | Nakajima et al. | |
| 2011/0136060 A1* | 6/2011 | Fujikawa et al. | 430/137.18 |
| 2011/0281213 A1 | 11/2011 | Sakashita et al. | |
| 2012/0082926 A1 | 4/2012 | Suzuki et al. | |

FOREIGN PATENT DOCUMENTS

| | | |
|---|---|---|
| JP | 2008-262179 | 10/2008 |
| JP | 2009-92927 | 4/2009 |
| JP | 2010-14757 | 1/2010 |

* cited by examiner

*Primary Examiner* — Mark F Huff
*Assistant Examiner* — Rashid Alam
(74) *Attorney, Agent, or Firm* — Oblon, Spivak, McClelland, Maier & Neustadt, L.L.P.

(57) ABSTRACT

In accordance with some embodiments, a toner including a first binder resin, a release agent, a release agent dispersing resin, and a colorant is provided. The first binder resin includes an amorphous polyester resin (a) having a polyhydroxycarboxylic acid skeleton in its main chain. The polyhydroxycarboxylic acid skeleton comprises optically-active monomers having an optical purity X of 80% by mole or less. The optical purity X is represented by the following formula:

$$X(\% \text{ by mole}) = |X(L\text{-form}) - X(D\text{-form})|$$

wherein X(L-form) and X(D-form) represent ratios (% by mole) of L-form and D-form optically-active monomers, respectively. The release agent includes an ester of a fatty acid having an average carbon number of 18 to 24 with glycerin or a polyglycerin having an average polymerization degree of 2 to 10. The ester has a melting point of 55 to 80° C.

13 Claims, 3 Drawing Sheets

TONER, DEVELOPER, IMAGE FORMING APPARATUS, AND IMAGE FORMING METHOD

CROSS-REFERENCE TO RELATED APPLICATIONS

This patent application is based on and claims priority pursuant to 35 U.S.C. §119 to Japanese Patent Application No. 2011-106418, filed on May 11, 2011, in the Japanese Patent Office, the entire disclosure of which is hereby incorporated herein by reference.

BACKGROUND

1. Technical Field

The present disclosure relates to a toner, a developer, an image forming apparatus, and an image forming method.

2. Description of Related Art

In an electrophotographic image forming apparatus or electrostatic recording device, an electric or magnetic latent image is developed into a toner image. In electrophotography, for example, an electrostatic latent image is formed on a photoreceptor and is developed into a toner image. The toner image is transferred onto a recording medium, such as paper, and fixed thereon by application of heat, etc.

It requires a large amount of electric power for melting and fixing the toner image on the recording medium. Therefore, toner is required to be fixable at much lower temperatures (this property is hereinafter referred to as "low-temperature fixability") from the viewpoint of energy saving. Toner is also required to be easily releasable from a heating member, such as a fixing roller, so as not to cause hot offset (this property is hereinafter referred to as "hot offset resistance").

One proposed method of improving hot offset resistance involves including a release agent in toner. (Such a toner may be referred to as an oilless toner.) As the release agent, natural waxes such as carnauba wax (i.e., plant) and paraffin wax (i.e., crude oil), and synthetic waxes such as polyethylene wax and polypropylene wax have been used for toner. However, these release agents not always sufficiently improve hot offset resistance of toner.

As an attempt to improve hot offset resistance, Japanese Patent Application Publication No. 2009-092927 proposes a release agent comprising an ester of a polyglycerin having an average polymerization degree of 2 to 10 with a fatty acid having an average carbon number of 16 to 24.

Low-temperature fixability of toner may be also improved by controlling thermal properties of binder resin. As an attempt to improve low-temperature fixability, Japanese Patent Application Publication Nos. 2008-262179 and 2010-014757 each propose a toner including an amorphous polyester resin, the main chain of which having a polyhydroxycarboxylic acid skeleton comprising L-monomer and D-monomer at a specific ratio (e.g., polylactic acid).

SUMMARY

In accordance with some embodiments, a toner including a first binder resin, a release agent, a release agent dispersing resin, and a colorant is provided. The first binder resin includes an amorphous polyester resin (a) having a polyhydroxycarboxylic acid skeleton in its main chain. The polyhydroxycarboxylic acid skeleton comprises optically-active monomers having an optical purity X of 80% by mole or less. The optical purity X is represented by the following formula:

$$X(\% \text{ by mole}) = |X(L\text{-form}) - X(D\text{-form})|$$

wherein X(L-form) and X(D-form) represent ratios (% by mole) of L-form and D-form optically-active monomers, respectively. The release agent includes an ester of a fatty acid having an average carbon number of 18 to 24 with glycerin or a polyglycerin having an average polymerization degree of 2 to 10. The ester has a melting point of 55 to 80° C.

In accordance with some embodiments, a developer including the above toner and a carrier is provided.

In accordance with some embodiments, an image forming apparatus is provided. The image forming apparatus includes an electrostatic latent image bearing member, an electrostatic latent image forming device adapted to form an electrostatic latent image on the electrostatic latent image bearing member, a developing device adapted to develop the electrostatic latent image into a toner image with the above developer, a transfer device adapted to transfer the toner image from the electrostatic latent image bearing member onto a recording medium, and a fixing device adapted to fix the toner image on the recording medium.

In accordance with some embodiments, an image forming method is provided. The image forming method includes the steps of forming an electrostatic latent image on an electrostatic latent image bearing member, developing the electrostatic latent image into a toner image with the above developer, transferring the toner image from the electrostatic latent image bearing member onto a recording medium, and fixing the toner image on the recording medium.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
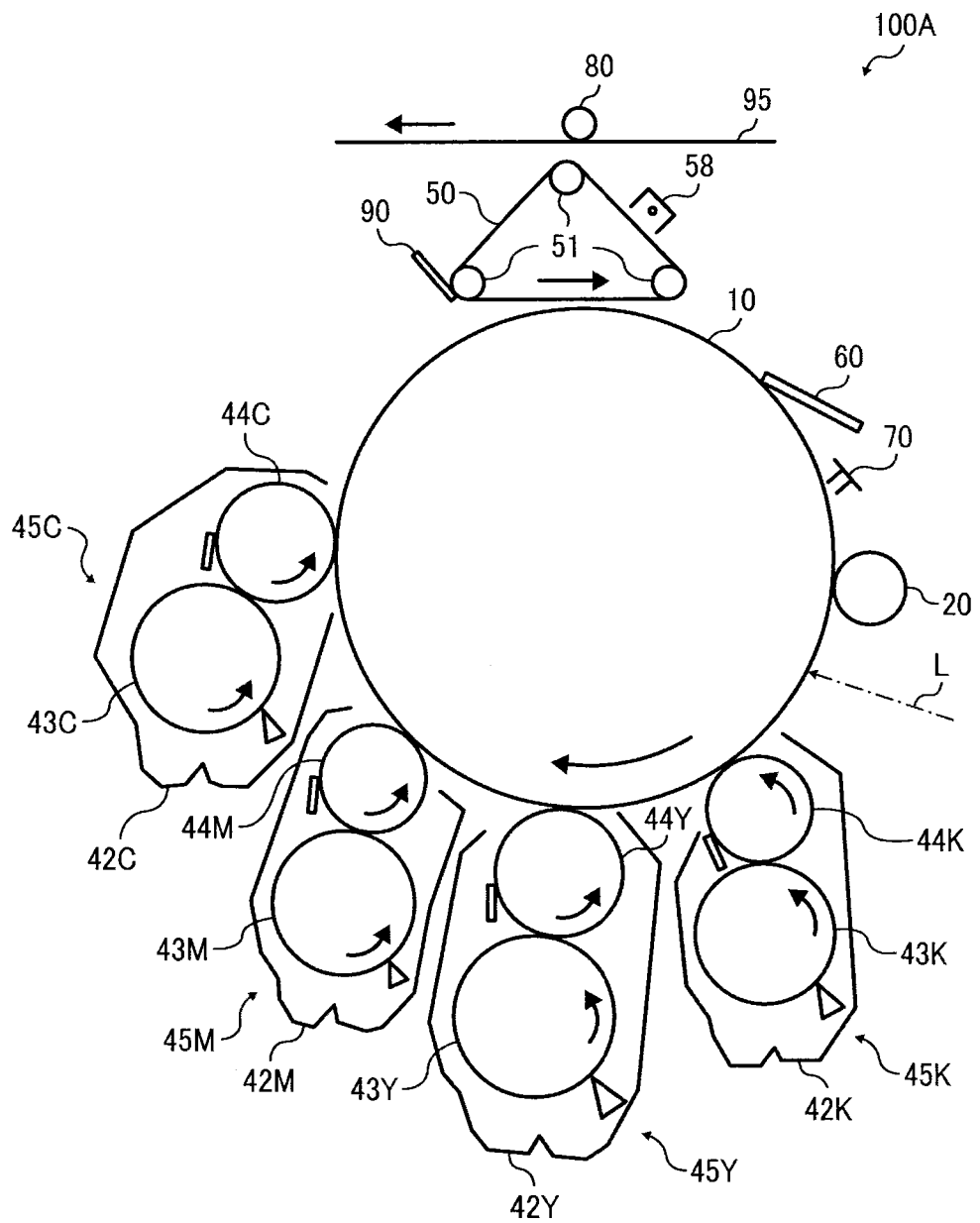
FIG. 1 is a schematic view of an image forming apparatus according to an embodiment.

Embodiments of the present invention are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that operate in a similar manner and achieve a similar result.

For the sake of simplicity, the same reference number will be given to identical constituent elements such as parts and materials having the same functions and redundant descriptions thereof omitted unless otherwise stated.

A toner according to an embodiment includes a first binder resin, a release agent, a release agent dispersing resin, and a colorant. The toner may be obtained by dissolving or dispersing the above toner components in an organic solvent and emulsifying the resulting oily toner components liquid in an aqueous medium.

The first binder resin includes an amorphous polyester resin (a) having a polyhydroxycarboxylic acid skeleton in its main chain. The polyhydroxycarboxylic acid skeleton comprises optically-active monomers.

The amorphous polyester resin (a) includes a high level of ester groups in its main chain and short-chain alkyl groups in its side chains. Thus, the amorphous polyester resin (a) includes a relatively higher level of ester groups per molecule compared to typical polyester resins not having polyhydroxycarboxylic acid skeleton in their main chains. Therefore, the amorphous polyester resin (a) has high affinity for paper, which results in improvement of low-temperature fixability. Because of being amorphous, the amorphous polyester resin (a) also has high transparency.

The polyhydroxycarboxylic acid skeleton comprises a skeleton in which a single hydroxycarboxylic acid is polymerized or multiple hydroxycarboxylic acids are copolymerized. The polyhydroxycarboxylic acid skeleton can be obtained by hydrolysis condensation of hydroxycarboxylic acids, ring-opening polymerization of cyclic esters of the hydroxycarboxylic acids, or lipase enzyme reaction, for example. In some embodiments, ring-opening polymerization of cyclic esters of hydroxycarboxylic acids is employed. In such embodiments, the resulting polyhydroxycarboxylic acid skeleton has a greater molecular weight.

In some embodiments, the optically-active monomers forming the polyhydroxycarboxylic acid skeleton include aliphatic hydroxycarboxylic acids or hydroxycarboxylic acids having 3 to 6 carbon atoms, in view of transparency and thermal property. Specific examples of such hydroxycarboxylic acids include, but are not limited to, lactic acid and 3-hydroxybutyric acid. Other than the hydroxycarboxylic acids, cyclic esters of the hydroxycarboxylic acids are also usable as raw materials of the polyhydroxycarboxylic acid skeleton. In this case, the resulting skeleton has a configuration in which the hydroxycarboxylic acids constituting the cyclic esters are polymerized. For example, the polyhydroxycarboxylic acid skeleton obtained from lactic acid lactide has a configuration in which lactic acids are polymerized.

The polyhydroxycarboxylic acid skeleton has an optical purity X of 80% by mole or less or 60% by mole or less. The optical purity is represented by the following formula:

$$X(\% \text{ by mole}) = |X(L\text{-form}) - X(D\text{-form})|$$

wherein X(L-form) and X(D-form) represent ratios (% by mole) of L-form and D-form optically-active monomers, respectively.

When the optical purity is 80% or less, the amorphous polyester resin (a) has excellent solvent solubility and transparency. The optical purity within the above range may be achieved when raw materials of the amorphous polyester resin (a) include a mixture of L-form and D-form compounds, meso compounds, or a mixture of meso compounds with either D-form or L-form compounds.

The amorphous polyester resin (a) may be copolymerized with another resin having a different skeleton so long as transparency and thermal property do not deteriorate. The amorphous polyester resin (a) may further comprise diols, dicarboxylic acids, polyols (e.g., glycerin, glycolic acid), and/or polyhydroxy acids (e.g., malic acid, tartaric acid).

In some embodiments, the amorphous polyester resin (a) has a weight average molecular weight (Mw) of 7,000 to 70,000, 10,000 to 40,000, or 15,00 to 35,000, in view of heat-resistant storage stability and low-temperature fixability.

In some embodiments, the amorphous polyester resin (a) has a glass transition temperature (Tg) of 50 to 70° C. or 55 to 65° C. When Tg is less than 50° C., heat-resistant storage stability may be poor. When Tg is greater than 70° C., low-temperature fixability may be poor.

The optical purity X can be measured as follows. First, mix an analyte (e.g., a resin having a polyester skeleton or a toner including the resin) with a mixture solvent of pure water, 1N sodium hydroxide solution, and isopropyl alcohol, and agitate the mixture at 70° C. to cause hydrolysis. Next, filter the mixture to remove solid components and add sulfuric acid to neutralize the filtrate. Thus, an aqueous solution containing L-hydroxycarboxylic acid and/or D-hydroxycarboxylic acid, produced from the polyester resin, is obtained. Subject the aqueous solution to a measurement with a high-speed liquid chromatography (HPLC) equipped with chiral ligand exchangeable columns SUMICHIRAL OA-5000 (from Sumika Analysis Chemical Service, Ltd.). Determine peak areas S(L) and S(D) corresponding to L-hydroxycarboxylic acid and D-hydroxycarboxylic acid, respectively, from the resulting chromatogram. Calculate optical purity X from the following formulae.

$$X(L\text{-form}) (\% \text{ by mol}) = 100 \times S(L)/\{S(L)+S(D)\}$$

$$X(D\text{-form}) (\% \text{ by mol}) = 100 \times S(D)/\{S(L)+S(D)\}$$

$$\text{Optical purity } X(\% \text{ by mol}) = |X(L\text{-form}) - X(D\text{-form})|$$

A polyester diol (a11) having a polyhydroxycarboxylic acid skeleton can be obtained by copolymerizing a diol (11) with raw materials of the polyhydroxycarboxylic acid skeleton. Specific examples of the diol (11) include, but are not limited to, 1,2-propanediol, 1,3-propanediol, 1,4-butanediol, 1,6-hexanediol, 2 to 30 mol alkylene oxide ("AO") (e.g., ethylene oxide ("EO"), propylene oxide ("PO"), butylene oxide ("BO")) adducts of bisphenols (e.g., bisphenol A, bisphenol F, bisphenol S), and combinations thereof. In some embodiments, 1,2-propanediol, 1,3-propanediol, 1,4-butanediol, or an AO adduct of bisphenol A is used.

In some embodiments, the amorphous polyester resin (a) comprises a straight-chain polyester diol (a11) having a polyhydroxycarboxylic acid skeleton, to more improve low-temperature fixability. In some embodiments, the amorphous polyester resin (a) includes a straight-chain polyester resin (A) obtained by reacting the straight-chain polyester diol (a11) with another polyester diol (a12) with an elongating agent, to more improve heat-resistant storage stability.

Generally, straight-chain polyester resins are easy to control molecular weight, thermal properties, compatibility, etc., due to their simple structures. The straight-chain polyester resin (A) comprises units of (a11) and (a12). Therefore, properties of the straight-chain polyester resin (A) are controllable by controlling chemical structure and/or chemical structure of the unit of (a12).

The polyester diol (a12) may be obtained by, for example, reacting a dicarboxylic acid (13) with an excessive amount of diol (11). Specific examples of the polyester diol (a12) include, but are not limited to, reaction products of at least one compound selected from 1,2-propanediol, 1,3-propanediol, 1,4-butanediol, 1,6-hexanediol, and 2 to 30 mol AO (e.g., EO, PO, BO) adducts of bisphenols (e.g., bisphenol A, bisphenol F, bisphenol S) with at least one compound selected from terephthalic acid, isophthalic acid, adipic acid, and succinic acid.

In some embodiments, each of the polyester diols (a11) and (a12) has a number average molecular weight (Mn) of 500 to 30,000, 1,000 to 20,000, or 2,000 to 5,000.

The elongating agent for elongating the polyester diols (a11) and (a12) includes two functional groups reactive with the hydroxyl groups included in (a11) and (a12). For example, dicarboxylic acids (13) and anhydrides thereof, difunctional polyisocyanates (15), and difunctional polyepoxides (19) are usable as the elongating agent. In some embodiments, diisocyanate compounds or dicarboxylic acid compounds are used in view of compatibility between (a11) and (a12). Specific examples of the elongating agent include, but are not limited to, succinic acid, adipic acid, maleic acid and anhydride thereof, fumaric acid and anhydride thereof, phthalic acid, isophthalic acid, terephthalic acid, 1,3- or 1,4-phenylene diisocyanate, 2,4- or 2,6-tolylene diisocyanate (TDI), 2,4'- or 4,4'-diphenylmethane diisocyanate (MDI), hexamethylene diisocyanate (HDI), dicyclohexylmethane-4,4'-diisocyanate (hydrogenated MDI), isophorone diisocyanate (IPDI), and bisphenol A diglycidyl ether. In some embodiments, succinic acid, adipic acid, isophthalic acid, terephthalic acid, maleic acid or anhydride thereof, fumaric acid or anhydride thereof, HDI, or IPDI is used. In some embodiments, maleic acid or anhydride thereof, fumaric acid or anhydride thereof, or IPDI is used.

In some embodiments, the content of the elongating agent in the straight-chain polyester resin (A) is 0.1 to 30% by weight or 1 to 20% by weight, in view of transparency and thermal properties.

In some embodiments, the weight ratio between the polyester diol (a11) having a polyhydroxycarboxylic acid skeleton and the polyester diol (a12) is 31:69 to 90:10 or 40:60 to 80:20, in view of transparency and thermal properties.

In some embodiments, the toner further includes particles of a second binder resin (b) adhered to its surface. The second binder resin (b) may include, for example, a polyester or styrene-acrylic resin having a glass transition temperature (Tg) of 55 to 80° C. When Tg is less than 55° C., heat-resistant storage stability may be poor. When Tg is greater than 80° C., low-temperature fixability may be poor. Therefore, when Tg is less than 55° C. or greater than 80° C., low-temperature fixability and heat-resistant storage stability may not go together.

In some embodiments, the second binder resin (b) has a weight average molecular weight (Mw) of 9,000 to 45,000.

The toner may further include a resin other than the first and second binder resins. Specific examples of usable resins include, but are not limited to, vinyl resins, polyester resins, polyurethane resins, and epoxy resins. In some embodiments, polyester resins or polyurethane resins are used. A resin obtainable by reacting a reactive prepolymer with a compound having an active hydrogen group, to be described in later, is also usable.

Glass transition temperatures (Tg) of the binder resins can be measured using a differential scanning calorimeter (DSC), such as DSC-60 available from Shimadzu Corporation, based on a method according to ASTM D3418-82. Alternatively, Tg of the binder resins can be measured using a flowtester, such as a flowtester capillary rheometer CFT-500 available from Shimadzu Corporation, under the following measurement conditions.

Load: 30 kg/cm$^2$
Heating rate: 3.0° C./min
Die orifice diameter: 0.50 mm
Die length: 10.0 mm Number average molecular weight (Mn) and weight average molecular weight (Mw) of THF-soluble components in the binder resins other than polyurethane resins can be measured by gel permeation chromatography (GPC) under the following measurement conditions, for example.

Instrument: HLC-8120 available from Tosoh Corporation
Columns: 1 column of TSKgel GMHXL and 2 columns of TSKgel Multipore HXL-M
Sample solution: 0.25% THF solution
Injection volume: 100 μL
Flow rate: 1 mL/min
Measurement temperature: 40° C.
Detector: Refractive index detector
Reference substance: 12 Polystyrene standards (TSK standard POLYSTYRENE available from Tosoh Corporation) each having a molecular weight of 500, 1,050, 2,800, 5,970, 9,100, 18,100, 37,900, 96,400, 190,000, 355,000, 1,090,000, and 2,890,000)

Mn and Mw of polyurethane resins can be measured by GPC under the following measurement conditions, for example.

Instrument: HLC-8220GPC available from Tosoh Corporation
Columns: Guardcolumn a TSKgel α-M
Sample solution: 0.125% Dimethylformamide solution
Injection volume: 100 μL
Flow rate: 1 mL/min
Measuring temperature: 40° C.
Detector: Refractive index detector
Reference substance: 12 Polystyrene standards (TSK standard POLYSTYRENE available from Tosoh Corporation) each having a molecular weight of 500, 1,050, 2,800, 5,970, 9,100, 18,100, 37,900, 96,400, 190,000, 355,000, 1,090,000, and 2,890,000)

The toner according to an embodiment includes a release agent including an ester of a fatty acid having an average carbon number of 18 to 24 with glycerin or a polyglycerin having an average polymerization degree of 2 to 10. The ester may be hereinafter referred to as "glycerin or polyglycerin ester". The glycerin or polyglycerin ester has a melting point of 55 to 80° C., 60 to 75° C., or 65 to 75° C. When the melting point is within the above range, the toner has a good combination of hot offset resistance (releasability), heat-resistant storage stability, and filming resistance. When the melting point is less than 55° C., heat-resistant storage stability and filming resistance of the toner may be poor. Additionally, it may be difficult to finely and uniformly disperse such an ester in toner particles, resulting in deterioration of releasability and manufacturability of toner. When the melting point is greater than 80° C., low-temperature fixability and image gloss may be poor.

Melting point of the glycerin or polyglycerin ester can be measured using a DSC system such as DSC-60 available from Shimadzu Corporation as follows. First, put 5.0 mg of a sample (i.e., the glycerin or polyglycerin ester) in an aluminum container. Put the container on a holder unit and set it in an electric furnace. Heat it from 20° C. to 200° C. at a heating rate of 10° C./min under nitrogen atmosphere. Cool it from 200° C. to 0° C. at a cooling rate of 10° C./min and heat it again to 200° C. at a heating rate of 10° C./min, thus obtaining a DSC curve. Analyze the DSC curve with an analysis program in the DSC-60 to determine an endothermic peak observed in the second heating. A temperature at which the endothermic peak is observed defines the melting point of the sample.

The greater the average polymerization degree of the polyglycerin, the more positively chargeable the toner. In view of this, in some embodiments, glycerin or a polyglycerin having an average polymerization degree of 2 is used. When the average polymerization degree is greater than 10, such a polyglycerin has too high a melt viscosity, resulting in deterioration of hot offset resistance of toner.

Because of including a high level of ester bonds and having a branched-chain molecular structure, the glycerin or polyglycerin ester has a moderate affinity for the amorphous polyester resin (a) having a polyhydroxycarboxylic acid skeleton in its main chain. Therefore, the glycerin or polyglycerin ester can be uniformly and finely dispersed in the amorphous polyester resin (a) having a polyhydroxycarboxylic acid skeleton in its main chain. The average polymerization degree of polyglycerin can be calculated from the hydroxyl value of the polyglycerin.

Hydroxyl value is defined as the amount (mg) of potassium hydroxide (KOH) needed for neutralizing acetic acid bound to hydroxyl groups when 1 g of a sample is acetylated as follows. Precisely weigh about 1 g of a sample and put it in a round-bottom flask. Precisely weigh 5 mL of an acetic anhydride/pyridine test solution and add it to the flask. Put a small funnel on an opening of the flask and heat the flask for 1 hour in an oil bath at 95 to 100° C. while immersing the bottom of the flask therein for a depth of about 1 cm. Subsequently, cool the flask and add 1 ml of water thereto. Shake the flask well and further heat it for 10 minutes. Cool the flask again and wash the small funnel and the neck of the flask with 5 mL of ethanol. After adding 1 mL of a phenolphthalein test solution as an indicator to the flask, titrate excessive acetic acid with a 0.5 mol/L potassium hydroxide ethanol solution (i.e., a main test). On the other hand, repeat the above procedure except for containing no sample in the flask (i.e., a blank test). Calculate hydroxyl value from the following equation:

$$OHV = ((a-b) \times 28.5)/W + AV$$

wherein OHV (mgKOH/g) represents a hydroxyl value; AV (mgKOH/g) represents an acid value; a and b (mL) represent amounts of the 0.5 mol/L potassium hydroxide ethanol solution consumed in the blank test and the main test, respectively; and W (g) represents an amount of the sample.

Specific examples of the fatty acids having an average carbon number of 18 to 24 include, but are not limited to, stearic acid, behenic acid, lignoceric acid, and combinations thereof. In some embodiments, stearic acid or behenic acid is used because they are capable of increasing melting point of the glycerin or polyglycerin ester and providing high releasability. When the average carbon number of the fatty acid is less than 18, melting point of the glycerin or polyglycerin ester may be too low, resulting in deterioration of heat-resistant storage stability and filming resistance of the toner. Additionally, it may be difficult to finely and uniformly disperse such an ester in toner particles. When the average carbon number of the fatty acid is greater than 24, melting point of the glycerin or polyglycerin ester may be too high, resulting in deterioration of low-temperature fixability and image gloss of the toner.

In some embodiments, the average esterification degree of the glycerin or polyglycerin ester, i.e., the ratio of hydroxyl groups (—OH) in the glycerin or polyglycerin forming ester bonds with fatty acids, is 90% or more or 95% or more. When the average esterification degree is less than 90%, hot offset resistance of the toner may be poor.

The glycerin or polyglycerin ester is sharply meltable at lower temperatures ("sharply-melting property"). In some embodiments, the glycerin or polyglycerin ester has a melt viscosity of 1 to 50 mPa·sec at 100° C. In such embodiments, the toner has a good combination of low-temperature fixability and offset resistance and is capable of producing high-gloss images. When the melt viscosity at 100° C. is greater than 50 mPa·sec, low-temperature fixability and image gloss may be poor. Melt viscosity can be measured by a Brookfield rotating viscometer.

In some embodiments, the glycerin or polyglycerin ester is dispersed in the toner with a dispersion diameter of 0.2 to 1.0 µm. The dispersion diameter is defined as the particle diameter in the maximum direction. When the dispersion diameter is greater than 1.0 µm, the content of the glycerin or polyglycerin ester in each toner particle may be vary considerably, which results in deterioration of releasability or particle size distribution of the toner. Additionally, it is likely that the glycerin or polyglycerin ester is exposed at the surface of the toner, which results in contamination of developing device or carrier particles. When the dispersion diameter is less than 0.2 µm, the occupation of the glycerin or polyglycerin ester inside the toner is too high, resulting in deterioration of releasability of the toner.

The dispersion diameter of the glycerin or polyglycerin ester can be measured as follows. Embed the toner in an epoxy resin and cut it into a ultrathin section having a thickness of about 100 nm. After dyeing the ultrathin section with ruthenium tetraoxide, observe and photograph the dyed ultrathin section with a transmission electron microscope (TEM) at a magnification of 10,000. Determine the dispersion diameter from the photograph.

Specific examples of the glycerin or polyglycerin ester are shown below. Two or more of the following materials can be used in combination.

Fatty acid esters of glycerin having a carbon number of 18 to 24: such as glycerin stearate, glycerin distearate, glycerin tristearate, glycerin behenate, glycerin dibehenate, glycerin tribehenate, glycerin lignocerate, glycerin dilignocerate, and glycerin trilignocerate. Fatty acid esters of diglycerin (i.e., polyglycerin having an average polymerization degree of 2) having a carbon number of 18 to 24: such as diglycerin stearate, diglycerin distearate, diglycerin tristearate, diglycerin tetrastearate, diglycerin behenate, diglycerin dibehenate, diglycerin tribehenate, diglycerin tetrabehenate, diglycerin lignocerate, diglycerin dilignocerate, diglycerin trilignocerate, and diglycerin tetralignocerate.

Fatty acid esters of tetraglycerin (i.e., polyglycerin having an average polymerization degree of 4) having a carbon number of 18 to 24: such as tetraglycerin stearate, tetraglycerin distearate, tetraglycerin tristearate, tetraglycerin tetrastearate, tetraglycerin pentastearate, tetraglycerin hexastearate, tetraglycerin behenate, tetraglycerin dibehenate, tetraglycerin tribehenate, tetraglycerin tetrabehenate, tetraglycerin pentabehenate, tetraglycerin hexabehenate, tetraglycerin lignocerate, tetraglycerin dilignocerate, tetraglycerin trilignocerate, tetraglycerin tetralignocerate, tetraglycerin pentalignocerate, and tetraglycerin hexalignocerate.

Fatty acid esters of hexaglycerin (i.e., polyglycerin having an average polymerization degree of 6) having a carbon number of 18 to 24: such as hexaglycerin stearate, hexaglycerin distearate, hexaglycerin tristearate, hexaglycerin tetrastearate, hexaglycerin pentastearate, hexaglycerin hexastearate, hexaglycerin heptastearate, hexaglycerin octastearate, hexaglycerin behenate, hexaglycerin dibehenate, hexaglycerin tribehenate, hexaglycerin tetrabehenate, hexaglycerin pentabehenate, hexaglycerin hexabehenate, hexaglycerin heptabehenate, hexaglycerin octabehenate, hexaglycerin lignocerate, hexaglycerin dilignocerate, hexaglycerin trilignocerate, hexaglycerin tetralignocerate, hexaglycerin pentalignocerate, hexaglycerin hexalignocerate, hexaglycerin heptalignocerate, and hexaglycerin octalignocerate.

Fatty acid esters of decaglycerin (i.e., polyglycerin having an average polymerization degree of 10) having a carbon number of 18 to 24: such as decaglycerin stearate, decaglycerin distearate, decaglycerin tristearate, decaglycerin tetrastearate, decaglycerin pentastearate, decaglycerin hexastearate, decaglycerin heptastearate, decaglycerin octastearate, decaglycerin nonastearate, decaglycerin decastearate, decaglycerin undecastearate, decaglycerin dodecastearate, decaglycerin behenate, decaglycerin dibehenate, decaglycerin tribehenate, decaglycerin tetrabehenate, decaglycerin pentabehenate, decaglycerin hexabehenate, decaglycerin heptabehenate, decaglycerin octabehenate, decaglycerin nonabehenate, decaglycerin decabehenate, decaglycerin undecabehenate, decaglycerin dodecabehenate, decaglycerin lignocerate, decaglycerin dilignocerate, decaglycerin trilignocerate, decaglycerin tetralignocerate, decaglycerin pentalignocerate, decaglycerin hexalignocerate, decaglycerin heptalignocerate, decaglycerin octalignocerate, decaglycerin nonalignocerate, decaglycerin decalignocerate, decaglycerin undecalignocerate, and decaglycerin dodecalignocerate. In some embodiments, glycerin tribehenate or diglycerin tetrabehenate is used in view of dispersibility in the toner and hot offset resistance.

In some embodiments, the content of the glycerin or polyglycerin ester in the toner is 3 to 15% by weight or 5 to 12% by weight based on resin components in the toner. When the content of the glycerin or polyglycerin ester is less than 3% by weight, hot offset resistance of the toner may be poor. When the content of the glycerin or polyglycerin ester is greater than 15% by weight, fluidity, transferability, and chargeability of the toner may be poor.

The content of the glycerin or polyglycerin ester in the toner can be determined by differential scanning calorimetry as follows. First, subject the glycerin or polyglycerin ester to a DSC measurement to determine the amount of heat Qw [J/mg] for melting unit weight of the glycerin or polyglycerin ester. Next, subject the toner to the DSC measurement to determine the amount of heat Qt [J/mg] for melting the glycerin or polyglycerin ester included in unit weight of the toner, from an endothermic peak of the glycerin or polyglycerin ester. The content W of the glycerin or polyglycerin ester can be calculated from the following formula:

$$W = Qt/Qw \times 100 (\% \text{ by weight})$$

The release agent can be introduced into the toner by dispersing the release agent in the binder resin by kneading and dispersing or dissolving the kneaded product in an oily toner composition, or dispersing or dissolving the release agent in a solvent in which a release agent dispersing resin, and the binder resin if needed, is/are dissolved.

The toner according to an embodiment includes a release agent dispersing resin. The release agent dispersing resin includes (1) a graft polymer comprising a polyolefin resin and a vinyl resin and/or (2) a polyester resin comprising a fatty acid ester having a branched structure comprising a fatty acid having a carbon number of 16 to 24 and a polyol having 3 or more valences.

(1) Graft polymer: The graft polymer has a main chain comprising a polyolefin resin to which a vinyl resin is grafted. The graft polymer may be obtained by graft-polymerizing a polyolefin resin and a vinyl monomer in an organic solvent in the presence of a polymerization initiator such as an organic peroxide. In some embodiments, the weight ratio between the polyolefin resin and the vinyl monomer is 1:99 to 30:70 or 5:95 to 25:75 in view of filming resistance.

Actually, the "graft polymer" may be a mixture resin of graft polymer with by-products including unreacted polyolefin resin and non-graft vinyl polymer produced from unreacted vinyl monomers. However, there is no need to remove these by-products. In some embodiments, the content of unreacted polyolefin resin in the mixture resin is 5% by weight or less or 3% by weight or less. In some embodiments, the content of non-graft vinyl polymer in the mixture resin is 10% by weight or less or 5% by weight or less. In some embodiments, the content of graft polymer in the mixture resin is 85% by weight or more or 90% by weight or more. Content of graft polymer in the mixture resin, molecular weights of graft polymer and vinyl polymer, etc. can be adjusted by controlling the raw material composition, reaction temperature, reaction time, etc.

In some embodiments, at least a part of the release agent is incorporated into or adhered to the graft polymer.

The graft polymer is adapted to suppress reaggregation of the finely-pulverized release agent in the toner components liquid and is also adapted to transfer the release agent from the surface to inside of the toner to suppress surface localization of the release agent. The graft polymer is able to suppress reaggregation of the release agent because polyolefin units in the graft polymer have high affinity for the release agent. The graft polymer is able to transfer the release agent from the surface to inside of the toner due to a particular interaction with the amorphous polyester resin (a).

The polyolefin resin may be comprised of, for example, ethylene, 1-butene, isobutylene, 1-hexene, 1-dodecene, and 1-octadecene.

Specific examples of usable polyolefin resins include, but are not limited to, olefin-based polymers and thermally-degraded products, oxides, and denatured products thereof; and olefin-based copolymers.

Specific examples of usable olefin-based polymer include, but are not limited to, polyethylene, polypropylene, ethylene-propylene copolymer, ethylene-1-butene copolymer, and propylene-1-hexene copolymer.

Specific examples of usable thermally-degraded olefin-based polymers include low-molecular-weight polyolefin resins obtained by heating polyolefin resins having a weight average molecular weight (Mw) of 50,000 to 5,000,000 to 250 to 450° C. In some embodiments, such low-molecular-weight polyolefin resins include 30 to 70% of double bonds per molecule, which is determined from the number average molecular weight (Mn).

Specific examples of usable oxides of olefin-based polymers include, but are not limited to, oxides of the above-described olefin-based polymers.

Specific examples of usable denatured products of olefin-based polymers include, but are not limited to, maleic acid derivative adducts of the above-described olefin-based polymers. Specific examples of the maleic acid derivatives include, but are not limited to, maleic anhydride, monomethyl maleate, monobutyl maleate, and dimethyl maleate.

Specific examples of usable olefin-based copolymers include, but are not limited to, copolymers of olefins with unsaturated carboxylic acids or alkyl esters thereof. Specific examples of the unsaturated carboxylic acids include, but are not limited to, acrylic acid, methacrylic acid, itaconic acid, and malic anhydride. Specific examples of the alkyl esters of unsaturated carboxylic acids include, but are not limited to, alkyl esters of acrylic, methacrylic, and maleic acids having 1 to 18 carbon atoms.

The polyolefin resin has a polyolefin molecular structure but monomers thereof need not necessarily have an olefin structure. Therefore, polymethylenes such as SASOL WAX can also be used.

In some embodiments, the polyolefin resin has a softening point of 60 to 170° C. in view of fluidity of the toner, or 70 to 150° C. or 70 to 130° C. in view of releasability of the toner.

In some embodiments, the polyolefin resin has a number average molecular weight (Mn) of 500 to 20,000 and a weight average molecular weight (Mw) of 800 to 100,000, Mn of 1,000 to 15,000 and Mw of 1,500 to 60,000, or Mn of 1,500 to 10,000 and Mw of 2,000 to 30,000, in view of filming resistance and releasability.

Specific examples of usable vinyl resins include, but are not limited to, homopolymers and copolymer of vinyl monomers such as styrene monomers, alkyl esters of unsaturated carboxylic acids having 1 to 18 carbon atoms, vinyl ester monomers, vinyl ether monomers, halogen-containing vinyl monomers, diene monomers, and unsaturated nitrile monomers such as acrylonitrile and methacrylonitrile. Two or more of these monomers can be used in combination.

Specific examples of the styrene monomers include, but are not limited to, styrene, α-methylstyrene, p-methylstyrene, m-methylstyrene, p-methoxystyrene, p-hydroxystyrene, p-acetoxystyrene, ethylstyrene, phenylstyrene, and benzylstyrene.

Specific examples of the alkyl esters of unsaturated carboxylic acids having 1 to 18 carbon atoms include, but are not limited to, methyl acrylate, methyl methacrylate, ethyl acrylate, ethyl methacrylate, butyl acrylate, butyl methacrylate, 2-ethylhexyl acrylate, and 2-ethylhexyl methacrylate.

Specific examples of the vinyl ester monomers include, but are not limited to, vinyl acetate. Specific examples of the vinyl ether monomers include, but are not limited to, vinyl methyl ether. Specific examples of the halogen-containing vinyl monomers include, but are not limited to, vinyl chloride. Specific examples of the diene monomers include, but are not limited to, butadiene and isobutylene.

In some embodiments, a styrene monomer, an alkyl ester of an unsaturated carboxylic acid, acrylonitrile, methacrylonitrile, or a combination thereof is used. In some embodiments, styrene alone or a combination of styrene with an alkyl ester of acrylic or methacrylic acid or acrylonitrile or methacrylonitrile is used.

The solubility parameter (SP) of the vinyl resin is adjusted in view of that of the amorphous polyester resin (a). Solubility parameters can be calculated by the Fedors method.

In some embodiments, the vinyl resin has a number average molecular weight (Mn) of 1,500 to 100,000 and a weight average molecular weight (Mw) of 5,000 to 200,000, Mn of 2,500 to 50,000 and Mw of 6,000 to 100,000, or Mn of 2,800 to 20,000 and Mw of 7,000 to 50,000.

In some embodiments, the vinyl resin has a glass transition temperature (Tg) of 50 to 80° C. or 55 to 70° C. in view of storage stability and low-temperature fixability of the toner.

For example, the graft polymer may comprise a combination of a polyolefin resin (R) and a vinyl resin (S) shown below.

(R): polyethylene, (S): styrene/acrylonitrile/butyl acrylate copolymer (R): polyethylene, (S): styrene/acrylonitrile/butyl acrylate/acrylic acid copolymer (R): polypropylene, (S): styrene/acrylonitrile/butyl acrylate copolymer (R): polypropylene, (S): styrene/acrylonitrile/butyl acrylate/acrylic acid copolymer (R): polypropylene, (S): styrene/acrylonitrile/butyl acrylate/monobutyl maleate copolymer (R): oxidized polypropylene, (S): styrene/acrylonitrile copolymer (R): polyethylene/polypropylene mixture, (S): styrene/acrylonitrile copolymer (R): ethylene/propylene copolymer, (S): styrene/acrylic acid/butyl acrylate copolymer (R): ethylene/propylene copolymer, (S): styrene/acrylonitrile/butyl acrylate copolymer (R): maleic-acid-modified polypropylene, (S): styrene/acrylonitrile/acrylic acid/butyl acrylate copolymer (R): maleic-acid-modified polypropylene, (S): styrene/acrylonitrile/acrylic acid/2-ethylhexyl acrylate copolymer (R): polyethylene/maleic-acid-modified polypropylene mixture, (S): acrylonitrile/butyl acrylate/styrene/monobutyl maleate copolymer The graft polymer may be produced by, for example, dissolving or dispersing a polyolefin resin in a solvent such as toluene and xylene, heating the resulting solution or dispersion to 100 to 200° C., dropping a vinyl monomer therein together with a peroxide-based initiator to initiate a polymerization, and removing the solvent. Specific examples of usable peroxide-based initiators include, but are not limited to, benzoyl peroxide, di-t-butyl peroxide, di-t-butylperoxyhexahydroterephthalate, and t-butyl peroxide benzoate.

In some embodiments, the used amount of the peroxide-based initiator is 0.2 to 10% by weight or 0.5 to 5% by weight based on the weight of raw material.

In some embodiments, the content of the graft polymer, including unreacted polyolefin and vinyl resins, in the toner is 30 to 100 parts by weight or 40 to 90 parts by weight, based on 100 parts by weight of the release agent, in view of stable dispersibility of the release agent.

(2) Polyester Resin comprising Fatty Acid Ester having Branched Structure: As described above, the release agent dispersing resin may include a polyester resin comprising a fatty acid ester having a branched structure comprising a fatty acid having a carbon number of 16 to 24 and a polyol having 3 or more valences.

The fatty acid ester having a branched structure may be obtained by reacting a fatty acid having a carbon number of 16 to 24 with a polyol having 3 or more valences. The fatty acid includes 16 to 24 carbon atoms or 18 to 24 carbon atoms. Specific examples of usable fatty acids include, but are not limited to, pahnitic acid, stearic acid, arachidic acid, eicosanoic acid, behenic acid, lignoceric acid, and combinations thereof. When the carbon number is less than 16, heat-resistant storage stability of the toner may be poor because the glass transition temperature (Tg) of the polyester resin comprising the fatty acid ester having a branched structure is too low. When the carbon number is greater than 24, low-temperature fixability of the toner may be poor. Specific examples of usable polyols having 3 or more valences include, but are not limited to, glycerin, trimethylolpropane, pentaerythritol, and dipentaerythritol.

The polyester resin primarily comprises a dicarboxylic acid component and a diol component.

Specific examples of the dicarboxylic acid component include, but are not limited to, aromatic dicarboxylic acids such as terephthalic acid and isophthalic acid; aliphatic dicarboxylic acids such as phthalic acid, sebacic acid, isodecyl succinic acid, maleic acid, fumaric acid, and adipic acid; and lower alkyl esters and acid anhydrides of the above compounds. Specific examples of the lower alkyl esters of dicarboxylic acids include, but are not limited to, monomethyl, monoethyl, dimethyl, and diethyl esters of the above-described dicarboxylic acids. Two or more of these dicarboxylic acid components can be used in combination. In some embodiments, terephthalic acid or isophthalic acid is used.

Specific examples of the diol component include, but are not limited to, aliphatic diols and aromatic diols.

Specific examples of the aliphatic diols include, but are not limited to, ethylene glycol, 1,2-propanediol, 1,3-propanediol, 1,3-butanediol, 1,4-butanediol, neopentyl glycol, diethylene glycol, triethylene glycol, polyethylene glycol, and 1,4-cyclohexanedimethanol. Two or more of these compounds can be used in combination. In some embodiments, ethylene glycol or neopentyl glycol is used.

Specific examples of the aromatic diols include, but are not limited to, polyoxyethylene-(2.0)-2,2-bis(4-hydroxyphenyl)

propane, polyoxypropylene-(2.0)-2,2-bis(4-hydroxyphenyl)propane, polyoxypropylene-(2.2)-polyoxyethylene-(2.0)-2,2-bis(4-hydroxyphenyl)propane, polyoxypropylene-(6)-2,2-bis(4-hydroxyphenyl)propane, polyoxypropylene-(2.2)-2,2-bis(4-hydroxyphenyl)propane, polyoxypropylene-(2.4)-2,2-bis(4-hydroxyphenyl)propane, and polyoxypropylene-(3.3)-2,2-bis(4-hydroxyphenyl)propane. Two or more of these compounds can be used in combination. In some embodiments, polyoxypropylene-(n)-2,2-bis(4-hydroxyphenyl)propane satisfying 2.1≤n≤8 or polyoxyethylene-(n)-2,2-bis(4-hydroxyphenyl)propane satisfying 2.0≤n≤3.0 is used.

The polyester resin may further comprise a polycarboxylic acid component having 3 or more valences and/or a polyol component having 3 or more valences.

Specific examples of the polycarboxylic acid component having 3 or more valences include, but are not limited to, trimellitic acid, pyromellitic acid, 1,2,4-cyclohexanetricarboxylic acid, 2,5,7-naphthalenetricarboxylic acid, 1,2,4-naphthalenetricarboxylic acid, 1,2,7,8-octanetetracarboxylic acid, and acid anhydrides thereof. Specific examples of the polyol component having 3 or more valences include, but are not limited to, sorbitol, 1,4-sorbitan, pentaerythritol, dipentaerythritol, tripentaerythritol, 2-methylpropanetriol, 1,2,4-butanetriol, 1,2,5-pentanetriol, glycerol, and trimethylolpropane. In some embodiments, trimellitic acid and/or acid anhydride thereof, pentaerythritol, or trimethylolpropane is used. Two or more of these compounds can be used in combination.

In some embodiments, the content of the fatty acid ester having a branched structure in the polyester resin is 1 to 5% by weight or 1.5 to 4% by weight. When the content of the fatty acid ester having a branched structure is less than 1% by weight, the release agent may not be finely dispersed in the toner. When the content of the fatty acid ester having a branched structure is greater than 5% by weight, heat-resistant storage stability of the toner may be poor.

The polyester resin comprising the fatty acid ester having a branched structure may be produced by, for example, preparing a polyester resin by polymerization, mixing the polyester resin with a fatty acid ester having a branched structure, and melt-kneading the mixture. Alternatively, the fatty acid ester having a branched structure may be added during the polymerization. The latter case is more advantageous in terms of reliable dispersion of the fatty acid ester having a branched structure throughout the polyester resin.

The fatty acid ester having a branched structure may be produced as follows, for example. First, an esterification reaction is developed between a polyol having 3 or more valences and an excessive amount of a fatty acid having a carbon number of 16 to 24 at a temperature of 120 to 240° C. in the presence or absence of a catalyst, thus obtaining an esterification crude product. Next, the excessive fatty acids are removed from the esterification crude product by deoxidation with an alkali aqueous solution. Usable alkali aqueous solutions in the deoxidation include, but are not limited to, aqueous solutions of alkali metal salts (e.g., sodium hydroxide, potassium hydroxide, sodium carbonate, potassium carbonate, sodium hydrogen carbonate) and ammonium salts (e.g., ammonium carbonate). The addition amount of the alkali may be the same or twice as much as the equivalent amount of the acid value of the esterification crude product. Additionally, hydrocarbon solvents (e.g., toluene, xylene, cyclohexane), alcohols (e.g., methanol, ethanol, isopropanol), and water-soluble organic solvents (e.g., ethylene glycol, propylene glycol) are also usable in the deoxidation. After removing the alkali aqueous phase separated in the deoxidation, the remaining ester phase is repeatedly washed with warm or hot water until the phase becomes neutral. When any hydrocarbon solvent or water-soluble organic solvent is used, these solvents are distilled away under reduced pressures after the washing of the ester phase. Thus, a fatty acid ester having a branched structure is obtained.

The polyester resin may be produced by, for example, heating the dicarboxylic acid and diol components, optionally with the polycarboxylic acid and/or polyol components having 3 or more valences in a reaction vessel, to cause an esterification or transesterification reaction. As described above, the fatty acid ester having a branched structure may be added during the above reaction so as to improve dispersibility of the fatty acid ester having a branched structure in the polyester resin. In some embodiments, the esterification or transesterification reaction is caused at a temperature of 150 to 300° C. Water or alcohol that may be produced in the reaction can be removed by any known method. Subsequently, a polycondensation is caused under vacuum at 150 mmHg (20 kPa) while removing the diol components. In some embodiments, the polycondensation is caused at a temperature of 150 to 300° C.

In the esterification or transesterification reaction and polycondensation, a catalyst may be used, such as titanium butoxide, dibutyltin oxide, tin acetate, zinc acetate, tin sulfide, antimony trioxide, and germanium dioxide.

In some embodiments, the polyester resin comprising the fatty acid ester having a branched structure has a number average molecular weight (Mn) of 2,000 to 10,000 and a weight average molecular weight (Mw) of 5,000 to 80,000, or Mn of 3,000 to 5,000 and Mw of 8,000 to 60,000.

In some embodiments, the polyester resin comprising the fatty acid ester having a branched structure has a glass transition temperature (Tg) of 50 to 80° C. or 55 to 70° C.

In some embodiments, the content of the polyester resin comprising the fatty acid ester having a branched structure in the toner is 30 to 100 parts by weight or 40 to 90 parts by weight, based on 100 parts by weight of the release agent, in view of stable dispersibility of the release agent.

Specific examples of usable colorants include, but are not limited to, carbon black, Nigrosine dyes, black iron oxide, NAPHTHOL YELLOW S, HANSA YELLOW (10G, 5G and G), Cadmium Yellow, yellow iron oxide, loess, chrome yellow, Titan Yellow, polyazo yellow, Oil Yellow, HANSA YELLOW (GR, A, RN and R), Pigment Yellow L, BENZIDINE YELLOW (G and GR), PERMANENT YELLOW (NCG), VULCAN FAST YELLOW (5G and R), Tartrazine Lake, Quinoline Yellow Lake, ANTHRAZANE YELLOW BGL, isoindolinone yellow, red iron oxide, red lead, orange lead, cadmium red, cadmium mercury red, antimony orange, Permanent Red 4R, Para Red, Fire Red, p-chloro-o-nitroaniline red, Lithol Fast Scarlet G, Brilliant Fast Scarlet, Brilliant Carmine BS, PERMANENT RED (F2R, F4R, FRL, FRLL and F4RH), Fast Scarlet VD, VULCAN FAST RUBINE B, Brilliant Scarlet G, LITHOL RUBINE GX, Permanent Red FSR, Brilliant Carmine 6B, Pigment Scarlet 3B, Bordeaux 5B, Toluidine Maroon, PERMANENT BORDEAUX F2K, HELIO BORDEAUX BL, Bordeaux 10B, BON MAROON LIGHT, BON MAROON MEDIUM, Eosin Lake, Rhodamine Lake B, Rhodamine Lake Y, Alizarine Lake, Thioindigo Red B, Thioindigo Maroon, Oil Red, Quinacridone Red, Pyrazolone Red, polyazo red, Chrome Vermilion, Benzidine Orange, perynone orange, Oil Orange, cobalt blue, cerulean blue, Alkali Blue Lake, Peacock Blue Lake, Victoria Blue Lake, metal-free Phthalocyanine Blue, Phthalocyanine Blue, Fast Sky Blue, INDANTHRENE BLUE (RS and BC), Indigo, ultramarine, Prussian blue, Anthraquinone Blue, Fast Violet B, Methyl Violet Lake, cobalt violet, manganese violet, dioxane violet, Anthraquinone Violet, Chrome Green, zinc green, chromium oxide, viridian, emerald green, Pigment Green B, Naphthol Green B, Green Gold, Acid Green Lake, Malachite Green Lake, Phthalocyanine Green, Anthraquinone Green, titanium oxide, zinc oxide, and lithopone. Two or more of these materials can be used in combination.

Usable colorants are not limited in its color. The toner may include either a black, cyan, magenta, or yellow colorant or a combination thereof.

Specific examples of usable black colorants include, but are not limited to, carbon blacks (C.I. Pigment Black 7) such as furnace black, lamp black, acetylene black, and channel black; metals such as copper, iron (C.I. Pigment Black 11), and titanium oxide; and organic pigments such as aniline black (C.I. Pigment Black 1).

Specific examples of usable magenta colorants include, but are not limited to, C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 48:1, 49, 50, 51, 52, 53, 53:1, 54, 55, 57, 57:1, 58, 60, 63, 64, 68, 81, 83, 87, 88, 89, 90, 112, 114, 122, 123, 163, 177, 179, 202, 206, 207, 209, and 211; C.I. Pigment Violet 19; and C.I. Vat Red 1, 2, 10, 13, 15, 23, 29, and 35.

Specific examples of usable cyan colorants include, but are not limited to, C.I. Pigment Blue 2, 3, 15, 15:1, 15:2, 15:3, 15:4, 15:6, 16, 17, and 60; C.I. Vat Blue 6; C.I. Acid Blue 45; copper phthalocyanine pigments having a phthalocyanine skeleton substituted with 1 to 5 phthalimidemethyl groups; and Green 7 and Green 35.

Specific examples of usable yellow colorants include, but are not limited to, c. i. Pigment Yellow 0-16, 1, 2, 3, 4, 5, 6, 7, 10, 11, 12, 13, 14, 15, 16, 17, 23, 55, 65, 73, 74, 83, 97, 110, 151, 154, and 180; C.I. Vat Yellow 1, 3, and 20; and Orange 36.

In some embodiments, the content of the colorant in the toner is 1 to 15% by weight or 3 to 10% by weight. When the colorant content is less than 1% by weight, coloring power of the toner may be poor. When the colorant content is greater than 15% by weight, coloring power and electric property of the toner may be poor because the colorant cannot be uniformly dispersed in the toner.

The colorant can be combined with a resin to be used as a master batch. Specific examples of usable resins include, but are not limited to, polyester, polylactic acid, polymers and copolymers of styrene or styrene derivatives, polymethyl methacrylate, polybutyl methacrylate, polyvinyl chloride, polyvinyl acetate, polyethylene, polypropylene, epoxy resin, epoxy polyol resin, polyurethane, polyamide, polyvinyl butyral, polyacrylic acid resin, rosin, modified rosin, terpene resin, aliphatic or alicyclic hydrocarbon resin, aromatic petroleum resin, chlorinated paraffin, and paraffin wax. Two or more of these resins can be used in combination. In some embodiments, polyester or polylactic acid is used.

The master batch can be obtained by mixing and kneading a resin and a colorant while applying a high shearing force. To increase the interaction between the colorant and the resin, an organic solvent may be used. More specifically, the maser batch can be obtained by a method called flushing in which an aqueous paste of the colorant is mixed and kneaded with the resin and the organic solvent so that the colorant is transferred to the resin side, followed by removal of the organic solvent and moisture. This method is advantageous in that the resulting wet cake of the colorant can be used as it is without being dried. When performing the mixing or kneading, a high shearing force dispersing device such as a three roll mill may be used.

The toner may further include additives such as charge controlling agent, shape controlling agent, external additive, fluidity improving agent, cleanability improving agent, and magnetic material. Charge controlling agents are adapted to give proper charging ability to toner.

Specific examples of usable charge controlling agents include, but are not limited to, colorless or whitish materials, such as triphenylmethane dyes, molybdic acid chelate pigments, Rhodamine dyes, alkoxyamines, quaternary ammonium salts (including fluorine-modified quaternary ammonium salts), alkylamides, phosphor and phosphor-containing compounds, tungsten and tungsten-containing compounds, fluorine activators, metal salts of salicylic acid, and metal salts of salicylic acid derivatives. Two or more of these materials can be used in combination.

Specific examples of commercially available charge controlling agents include, but are not limited to, BONTRON® P-51 (quaternary ammonium salt), BONTRON® E-82 (metal complex of oxynaphthoic acid), BONTRON® E-84 (metal complex of salicylic acid), and BONTRON® E-89 (phenolic condensation product), which are available from Orient Chemical Industries Co., Ltd.; TP-302 and TP-415 (molybdenum complexes of quaternary ammonium salts), which are available from Hodogaya Chemical Co., Ltd.; COPY CHARGES PSY VP2038 (quaternary ammonium salt), COPY BLUE® PR (triphenyl methane derivative), COPY CHARGES NEG VP2036 and COPY CHARGE® NX VP434 (quaternary ammonium salts), which are available from Hoechst AG; LRA-901, and LR-147 (boron complex), which are available from Japan Carlit Co., Ltd.; and quinacridone, azo pigments, and polymers having a functional group such as a sulfonate group, a carboxyl group, and a quaternary ammonium group.

The charge controlling agent may be melt-kneaded with the colorant-resin master batch before being added to a toner components liquid. Alternatively, the charge controlling agent may be added to an organic solvent together with other toner components in preparing a toner components liquid. Alternatively, the charge controlling agent may be fixed on the surface of the resulting toner particles. In some embodiments, a fluorine-containing quaternary ammonium salt is fixed on the surface of the toner particles.

In some embodiments, the content of the charge controlling agent is 0.01 to 5% by weight or 0.02 to 2% by weight based on 100% the binder resin. When the content of charge controlling agent is greater than 5% by weight, the toner may be excessively charged and excessively electrostatically attracted to a developing roller, resulting in poor fluidity of the developer and low image density. When the content of the charge controlling agent is less than 0.01% by weight, the toner may not be charged quickly and sufficiently, resulting in poor image quality.

Shape controlling agents are adapted to control the shape of toner. Specific materials usable as the shape controlling agent include, but are not limited to, layered inorganic minerals in which at least a part of interlayer ions are modified with an organic ion (hereinafter "modified layered inorganic minerals"). Specific examples of such modified layered inorganic minerals include, but are not limited to, organic-cation-modified smectite-based materials. Metal anions can be introduced to a layered inorganic mineral by replacing a part of divalent metals with trivalent metals. In this case, at least a part of the introduced metal anions may be modified with an organic anion so as not to increase hydrophilicity of the layered inorganic mineral.

Specific materials usable as the organic cation modifying agent include, but are not limited to, quaternary alkyl ammonium salts, phosphonium salts, and imidazolium salts. In some embodiments, quaternary alkyl ammonium salts are used. Specific examples of the quaternary alkyl ammonium include, but are not limited to, trimethyl stearyl ammonium, dimethyl stearyl benzyl ammonium, and oleylbis(2-hydroxyethyl)methyl ammonium.

Specific materials usable as the organic cation modifying agent further include, but are not limited to, sulfates, sulfonates, carboxylates, and phosphates having a branched, non-branched, or cyclic alkyl (C1-C44), alkenyl (C1-C22), alkoxy (C8-C32), hydroxyalkyl (C2-C22), ethylene oxide, or propylene oxide. In some embodiments, carboxylic acids having an ethylene oxide skeleton are used.

The modified layered inorganic mineral has proper hydrophilicity due to the modification by the organic ion. A toner components liquid including such a modified layered inorganic mineral expresses non-Newtonian viscosity, which is capable of controlling or varying the resulting toner shape. In some embodiments, the content of the modified layered inorganic mineral in the toner is 0.05 to 10% by weight or 0.05 to 5% by weight.

Specific examples of the modified layered inorganic minerals include, but are not limited to, montmorillonite, bentonite, hectorite, attapulgite, sepiolite, and mixtures thereof. In some embodiments, an organic-modified montmorillonite or bentonite is used. They can easily control viscosity of the toner components liquid at a small amount without adversely affecting other toner properties.

Specific examples of commercially available organic-cation-modified layered inorganic minerals include, but are not limited to, quaternium 18 bentonite such as BENTONE® 3, BENTONE® 38, and BENTONE® 38V (from Rheox), TIXOGEL VP (from United Catalyst), and CLAYTONE® 34, CLAYTONE® 40, and CLAYTONE® XL (from Southern Clay Products); stearalkonium bentonite such as BENTONE® 27 (from Rheox), TIXOGEL LG (from United Catalyst), and CLAYTONE® AF and CLAYTONE® APA (from Southern Clay Products); and quaternium 18/benzalkonium bentonite such as CLAYTONE® HT and CLAYTONE® PS (from Southern Clay Products). In some embodiments, CLAYTONE® AF or CLAYTONE® APA is used. Specific examples of commercially available oranic-anion-modified layered inorganic minerals include, but are not limited to, HITENOL 330T (from Dai-ichi Kogyo Seiyaku Co., Ltd.) obtainable by modifying DHT-4A (from Kyowa Chemical Industry Co., Ltd.) with an organic anion represented by the following formula:

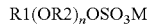

wherein R1 represents an alkyl group having 13 carbon atoms, R2 represents an alkylene group having 2 to 6 carbon atoms, n represents an integer of 2 to 10, and M represents a monovalent metal element.

External additives are adapted to adjust or improve fluidity, chargeability, and electric properties of toner. Specific materials usable as the external additive include, but are not limited to, fine particles of silica, hydrophobized silica, metal salts of fatty acids (e.g., zinc stearate, aluminum stearate), metal oxides (e.g., titania, alumina, tin oxide, antimony oxide), hydrophobized metal oxides, and fluoro polymers. In some embodiments, fine particles of hydrophobized silica, titania, or hydrophobized titania are used.

Specific examples of commercially available hydrophobized silica particles include, but are not limited to, HDK H2000, HDK H2000/4, HDK H2050EP, HVK21, and HDK H1303 (from Hoechst AG); and R972, R974, RX200, RY200, R202, R805, and R812 (from Nippon Aerosil Co., Ltd.).

Specific examples of commercially available titania particles include, but are not limited to, P-25 (from Nippon Aerosil Co., Ltd.); STT-30 and STT-65C-S (from Titan Kogyo, Ltd.); TAF-140 (from Fuji Titanium Industry Co., Ltd.); and MT-150W, MT-500B, MT-600B, and MT-150A (from TAYCA Corporation).

Specific examples of commercially available hydrophobized titania particles include, but are not limited to, T-805 (from Nippon Aerosil Co., Ltd.); STT-30A and STT-65S-S (from Titan Kogyo, Ltd.); TAF-500T and TAF-1500T (from Fuji Titanium Industry Co., Ltd.); MT-100S and MT-100T (from TAYCA Corporation); and IT-S (from Ishihara Sangyo Kaisha, Ltd.).

Hydrophobized particles of silica, titania, or alumina can be obtained by treating hydrophilic particles of silica, titania, or alumina with a silane coupling agent, such as methyltrimethoxysilane, methyltriethoxysilane, and octyltrimethoxysilane. Specific examples of usable hydrophobizing agents further include, but are not limited to, silane coupling agents (e.g., dialkyl dihalogenated silane, trialkyl halogenated silane, alkyl trihalogenated silane, hexaalkyl disilazane), sylation agents, silane coupling agents having a fluorinated alkyl group, organic titanate coupling agents, aluminum coupling agents, silicone oils, and modified silicone oils.

Alternatively, inorganic fine particles treated with a silicon oil upon application of heat are also usable. Specific examples of usable inorganic fine particles include, but are not limited to, silica, alumina, titanium oxide, barium titanate, magnesium titanate, calcium titanate, strontium titanate, iron oxide, copper oxide, zinc oxide, tin oxide, quartz sand, clay, mica, sand-lime, diatom earth, chromium oxide, cerium oxide, red iron oxide, antimony trioxide, magnesium oxide, zirconium oxide, barium sulfate, barium carbonate, calcium carbonate, silicon carbide, and silicon nitride. In some embodiments, silica or titanium dioxide is used.

Specific examples of usable silicone oils include, but are not limited to, dimethyl silicone oil, methyl phenyl silicone oil, chlorophenyl silicone oil, methyl hydrogen silicone oil, alkyl-modified silicone oil, fluorine-modified silicone oil, polyether-modified silicone oil, alcohol-modified silicone oil, amino-modified silicone oil, epoxy-modified silicone oil, epoxy-polyether-modified silicone oil, phenol-modified silicone oil, carboxyl-modified silicone oil, mercapto-modified silicone oil, acrylic-modified or methacrylic-modified silicone oil, and a-methylstyrene-modified silicone oil.

In some embodiments, the inorganic fine particles have an average primary particle diameter of 1 to 100 nm or 3 to 70 nm. When the average primary particle diameter is less than 1 nm, the inorganic fine particles may be buried in the toner without exerting their effect. When the average primary particle diameter is greater than 100 nm, an electrostatic latent image bearing may be damaged by the inorganic fine particles.

In some embodiments, the hydrophobized inorganic fine particles have an average primary particle diameter of 1 to 100 nm or 5 to 70 nm. In some embodiments, the toner includes at least two kinds of hydrophobized inorganic fine particles each having an average primary particle diameter of 20 nm or less and at least one kind of an inorganic fine particle having an average primary particle diameter of 30 nm or more. In some embodiments, the inorganic fine particles have a BET specific surface area of 20 to 500 $m^2/g$.

In some embodiments, the content of the external additive in the toner is 0.1 to 5% by weight or 0.3 to 3% by weight.

Additionally, resin particles are also usable as the external additive. For example, fine particles of polystyrene obtained by soap-free emulsion polymerization, suspension polymerization, or dispersion polymerization; copolymers of methacrylates or acrylates; polycondensation resins such as silicone, benzoguanamine, and nylon; and thermosetting resins, are usable. Combination use of inorganic and resin particles improves chargeability of toner while reducing oppositely-charged toner particles, resulting in prevention of the occurrence of background fouling.

In some embodiments, the content of the resin particles in the toner is 0.01 to 5% by weight or 0.1 to 2% by weight.

Fluidity improving agents are adapted to improve hydrophobicity of toner by surface treatment so as to prevent deterioration of fluidity and chargeability in high-humidity conditions. Specific materials usable as the fluidity improving agent include, but are not limited to, silane coupling agents, silylation agents, silane coupling agents having a fluorinated alkyl group, organic titanate coupling agents, aluminum coupling agents, silicone oils, and modified silicone oils. The above-described silica and titania particles can also be hydrophobized with the fluidity improving agent.

Cleanability improving agents are adapted to improve removability of toner from a photoreceptor or primary transfer medium. Specific materials usable as the cleanability improving agent include, but are not limited to, metal salts of fatty acids (e.g., zinc stearate, calcium stearate) and fine particles of polymers prepared by soap-free emulsion polymerization (e.g., polymethyl methacrylate, polystyrene). In some embodiments, the fine particles of polymers have a narrow size distribution and a volume average particle diameter of 0.01 to 1 μm.

Magnetic materials are adapted to give magnetic property to toner. Specific examples of usable magnetic materials include, but are not limited to, iron powder, magnetite, and ferrite. In some embodiments, a magnetic material having a whitish color is used.

The toner according to an embodiment may be produced by, for example, a polyaddition method in which a prepolymer having an isocyanate group is directly elongated and/or cross-linked with an amine in an aqueous phase, a pulverization method, or a melt-spraying method.

In some embodiments, the toner is prepared by dissolving or dispersing toner components, including a compound ($\beta$) having an active hydrogen group, a prepolymer ($\alpha$) having a reactive group, a first binder resin including an amorphous polyester resin (a), a colorant, and a release agent, in an organic solvent to prepare a toner components liquid; emulsifying or dispersing the toner components liquid in an aqueous medium containing particles of a second resin (b); reacting the compound ($\beta$) having an active hydrogen group with the prepolymer ($\alpha$) having a reactive group in the aqueous medium to prepare particles; and removing the organic solvent. (This method may be hereinafter referred to as the manufacturing method (I).)

Particles of the second binder resin (b) may be obtained in the form of aqueous dispersion. An aqueous dispersion of resin particles can be obtained by the following methods (i) to (viii), for example.

(i) An aqueous dispersion of a vinyl resin is obtainable by directly subjecting raw materials including a vinyl monomer to a suspension polymerization, an emulsion polymerization, a seed polymerization, or a dispersion polymerization.

(ii) An aqueous dispersion of a polyaddition or polycondensation resin (e.g., polyester resin, polyurethane resin, epoxy resin) is obtainable by dispersing a precursor (e.g., monomer, oligomer) of the resin or a solution thereof in an aqueous medium in the presence of a dispersant, and curing the precursor by application of heat or addition of a curing agent.

(iii) An aqueous dispersion of a polyaddition or polycondensation resin (e.g., polyester resin, polyurethane resin, epoxy resin) is obtainable by dissolving an emulsifier in a precursor (e.g., monomer, oligomer) of the resin or a solution (preferably in a liquid state, or which may be liquefied by application of heat) thereof, and further adding water thereto to cause phase-transfer emulsification.

(iv) An aqueous dispersion of a resin produced by a polymerization reaction (e.g., addition polymerization, ring-opening polymerization, polyaddition, addition condensation, polycondensation) is obtainable by pulverizing the resin into particles by a mechanical rotary pulverizer or a jet pulverizer, classifying the particles by size to collect desired-size particles, and dispersing the collected particles in an aqueous medium in the presence of a dispersant.

(v) An aqueous dispersion of a resin produced by a polymerization reaction (e.g., addition polymerization, ring-opening polymerization, polyaddition, addition condensation, polycondensation) is obtainable by dissolving the resin in a solvent, spraying the resulting resin solution to form resin particles, and dispersing the resin particles in an aqueous medium in the presence of a dispersant.

(vi) An aqueous dispersion of a resin produced by a polymerization reaction (e.g., addition polymerization, ring-opening polymerization, polyaddition, addition condensation, polycondensation) is obtainable by dissolving the resin in a solvent and further adding a poor solvent to the resulting resin solution, or dissolving the resin in a solvent by application of heat and cooling the resulting resin solution, to precipitate resin particles, removing the solvents to isolate the resin particles, and dispersing the resin particles in an aqueous medium in the presence of a dispersant.

(vii) An aqueous dispersion of a resin produced by a polymerization reaction (e.g., addition polymerization, ring-opening polymerization, polyaddition, addition condensation, polycondensation) is obtainable by dissolving the resin in a solvent, dispersing the resulting resin solution in an aqueous medium in the presence of a dispersant, and removing the solvent by application of heat and/or reduction of pressure.

(viii) An aqueous dispersion of a resin produced by a polymerization reaction (e.g., addition polymerization, ring-opening polymerization, polyaddition, addition condensation, polycondensation) is obtainable by dissolving the resin in a solvent, dissolving an emulsifier in the resulting resin solution, and adding water thereto to cause phase-transfer emulsification.

In some embodiments, the particles of the second resin (b) have a volume average particle diameter of 3 to 10 μm or 4 to 8 μm.

The prepolymer (a) having a reactive group is defined as a polymer having a functional group ($\alpha 1$) reactive with a compound having an active hydrogen group.

The functional group ($\alpha 1$) reactive with a compound having an active hydrogen group may be, for example, an isocyanate group ($\alpha 1a$), a blocked isocyanate group ($\alpha 1b$), an epoxy group ($\alpha 1c$), an acid anhydride group ($\alpha 1d$), and acid halide group ($\alpha 1e$). In some embodiments, an isocyanate group ($\alpha 1a$), a blocked isocyanate group ($\alpha 1b$), or an epoxy group ($\alpha 1c$) is employed. In some embodiments, an isocyanate group ($\alpha 1a$) or a blocked isocyanate group ($\alpha 1b$) is employed. The blocked isocyanate group ($\alpha 1b$) is defined as an isocyanate group blocked with a blocking agent.

Specific materials usable as the blocking agent include, but are not limited to, oximes (e.g., acetoxime, methyl isobutyl ketoxime, diethyl ketoxime, cyclopentanone oxime, cyclohexanone oxime, methyl ethyl ketoxime), lactams (e.g., γ-butyrolactam, ε-caprolactam, γ-valerolactam), aliphatic alcohols having 1 to 20 carbon atoms (e.g., methanol, ethanol, octanol), phenols (e.g., phenol, cresol, xylenol, nonylphenol), active methylene compounds (e.g., acetylacetone, ethyl malonate, ethyl acetoacetate), basic nitrogen-containing compounds (e.g., N,N-diethylhydroxylamine, 2-hydroxypyridine, pyridine-N-oxide, 2-mercaptopyridine), and mixtures thereof. In some embodiments, an oxime is used. In some embodiments, methyl ethyl oxime is used.

The prepolymer (α) having a reactive group may comprise a polyether (αw) skeleton, a polyester (αx) skeleton, an epoxy resin (αy) skeleton, or a polyurethane (αz) skeleton. In some embodiments, a polyester (αx) skeleton, an epoxy (αy) skeleton, or a polyurethane (αz) skeleton is employed. In some embodiments, a polyester (αx) skeleton or a polyurethane (αz) skeleton is employed.

The polyether (αw) may be, for example, polyethylene oxide, polypropylene oxide, polybutylene oxide, or polytetramethylene oxide.

The polyester (αx) may be, for example, a polycondensation product of a diol with a dicarboxylic acid or a polylactone (i.e., a ring-opening polymerization product of ε-caprolactone).

The epoxy resin (αy) may be, for example, an addition condensation product of a bisphenol (e.g., bisphenol A, bisphenol F, bisphenol S) with epichlorohydrin.

The polyurethane (αz) may be, for example, a polyaddition product of a diol with a polyisocyanate or a polyaddition product of the polyester (αx) with a polyisocyanate.

A reactive group can be introduced to the polyester (αx), epoxy resin (αy), or polyurethane (αz) by the following methods [1] and [2].

[1] React two or more components with one particular component being excessive so that a functional group of the particular component remains on a terminal.

[2] React two or more components with one particular component being excessive so that a functional group of the particular component remains on a terminal, and further react the remaining functional group with a compound having both a functional group reactive with the remaining functional group and a reactive group.

The above method [1] can produce, for example, polyester prepolymer having hydroxyl group, polyester prepolymer having carboxyl group, polyester prepolymer having acid halide group, epoxy resin prepolymer having hydroxyl group, epoxy resin prepolymer having epoxy group, polyurethane prepolymer having hydroxyl group, and polyurethane prepolymer having isocyanate group.

For example, a polyester prepolymer having hydroxyl group may comprise a polyol and a polycarboxylic acid with the equivalent ratio [OH]/[COOH] of hydroxyl groups [OH] from the polyol to carboxyl groups [COOH] from the polycarboxylic acid being 2/1 to 1/1, 1.5/1 to 1/1, or 1.3/1 to 1.02/1.

In the above method [2], for example, prepolymer having isocyanate group, prepolymer having blocked isocyanate group, prepolymer having epoxy group, and prepolymer having acid anhydride group can be produced by reacting the prepolymer produced by the method [1] with polyisocyanate, blocked polyisocyanate, polyepoxide, and poly(acid anhydride), respectively.

For example, a polyester prepolymer having isocyanate group can be obtained by reacting a polyester having hydroxyl group with a polyisocyanate with the equivalent ratio [NCO]/[OH] of isocyanate groups [NCO] from the polyisocyanate to hydroxyl groups [OH] from the polyester having hydroxyl group being 5/1 to 1/1, 4/1 to 1.2/1, or 2.5/1 to 1.5/1.

In some embodiments, the average number of reactive groups included in one molecule of the prepolymer (α) having a reactive group is 1 or more, 1.5 to 3, or 1.8 to 2.5. Within the above range, the reaction product of the prepolymer (α) having a reactive group with the compound (β) having an active hydrogen group has a high molecular weight. In some embodiments, the prepolymer (α) having a reactive group has a number average molecular weight (Mn) of 500 to 30,000, 1,000 to 20,000, or 2,000 to 10,000. In some embodiments, the prepolymer (α) having a reactive group has a weight average molecular weight (Mw) of 1,000 to 50,000, 2,000 to 40,000, or 4,000 to 20,000. In some embodiments, the prepolymer (α) having a reactive group has a viscosity of 2,000 poise or less or 1,000 poise or less at 100° C. When the viscosity is 2,000 poise or less, toner particles having a narrow size distribution can be obtained with use of a small amount of organic solvents.

The compound (β) having an active hydrogen group may be, for example, a polyamine (βa) which may be blocked with a releasable compound, a polyol (βb), a polymercaptan (βc), and water (βd). In some embodiments, a polyamine (βa) which may be blocked with a releasable compound, a polyol (βb), or water (βd) is used. In some embodiments, a polyamine (βa) or water (βd) is used. In some embodiments, a blocked polyamine or water (βd) is used. The polyamine (βa) may be, for example, 4,4'-diaminodiphenylmethane, xylylenediamine, isophoronediamine, ethylenediamine, diethylenetriamine, triethylenetetramine, or a mixture thereof.

The polyamine (βa) which is blocked with a releasable compound may be, for example, a ketimine compound obtained from a polyamine and a ketone having 3 to 8 carbon atoms (e.g., acetone, methyl ethyl ketone, methyl isobutyl ketone), an aldimine compounds obtained from an aldehyde compounds having 2 to 8 carbon atoms (e.g., formaldehyde, acetaldehyde), an enamine compound, or an oxazoline compound.

The polyol (βb) may be, for example, a diol or a polyol. In some embodiments, a diol alone or a mixture of a diol with a small amount of a polyol is employed.

The polymercaptan (βc) may be, for example, ethylenedithiol, 1,4-butanedithiol, or 1,6-hexanedithiol.

Specific examples of the polyamine (βa) further include the following compounds (1) to (4).

(1) Aliphatic polyamines (C2-C18)

(1-1) Aliphatic polyamines, such as alkylene(C2-C6)diamines (e.g., ethylenediamine, propylenediamine, trimethylenediamine, tetramethylenediamine, hexamethylenediamine) and polyalkylene(C2-C6)polyamines (e.g., diethylenetriamine, iminobispropylamine, bis(hexamethylene)triamine, triethylenetetramine, tetraethylenepentamine, pentaethylenehexamine).

(1-2) Alkyl(C1-C4) or hydroxyalkyl(C2-C4) substitutions of the aliphatic polyamines of (1-1), such as dialkyl(C1-C3)aminopropylamine, trimethylhexamethylenediamine, aminoethylethanolamine, 2,5-dimethyl-2,5-hexamethylenediamine, and methyliminobispropylamine.

(1-3) Alicyclic or heterocyclic aliphatic polyamines, such as 3,9-bis(3-aminopropyl)-2,4,8,10-tetraoxaspiro[5,5]undecane.

(1-4) Aromatic aliphatic amines (C8-C15), such as xylylenediamine and tetrachloro-p-xylylenediamine.

(2) Alicyclic polyamines (C4-C15), such as 1,3-diaminocyclohexane isophoronediamine, mencenediamine, and 4,4'-methylenedicyclohexanediamine (hydrogenated methylenedianiline).

(3) Heterocyclic polyamines (C4-C15), such as piperazine, N-aminoethylbipiperazine, 1,4-diaminoethylbipiperazine, 1,4-bis(2-amino-2-methylpropyl)piperazine.

(4) Aromatic polyamines (C6-C20)

(4-1) Unsubstituted aromatic polyamines, such as 1,2-, 1,3-, or 1,4-phenylenediamine, 2,4'- or 4,4'-diphenylmethanediamine, crude diphenylmethanediamine (polyphenyl polymethylene polyamine), diaminodiphenylsulfone, benzidine, thiodianiline, bis(3,4-diaminophenyl)sulfone, 2,6-diaminopyridine, m-aminobenzylamine, triphenylmethane-4,4',4"-triamine, and naphthylenediamine.

(4-2) Aromatic polyamines having a nuclear-substituted alkyl group (e.g., an alkyl(C1-C4) group such as methyl, ethyl, or n- or i-propylbutyl group), such as 2,4- or 2,6-tolylenediamine, crude tolylenediamine, diethyltolylenediamine, 4,4'-diamino-3,3'-dimethyldiphenylmethane, 4,4'-bis (o-tolidine), dianisidine, diaminoditolyl sulfone, 1,3-dimethyl-2,4-diaminobenzene, 1,3-dimethyl-2,6-diaminobenzene, 1,4-diisopropyl-2,5-diaminobenzene, 2,4-diaminomesitylene, 1-methyl-3,5-diethyl-2,4-diaminobenzene, 2,3-dimethyl-1,4-diaminonaphthalene, 2,6-dimethyl-1,5-diaminonaphthalene, 3,3,5,5-tetramethylbenzidine, 3,3,5,5-tetramethyl-4,4'-diaminodiphenylmethane, 3,5-diethyl-3'-methyl-2',4-diaminodiphenylmethane, 3,3'-diethyl-2,2'-diaminodiphenylmethane, 4,4-diamino-3,3'-dimethyldiphenylmethane, 3,3,5,5-tetraethyl-4,4-diaminobenzophenone, 3,3,5,5-tetraethyl-4,4'-diaminophenyl ether, 3,3,5,5-tetraisopropyl-4,4'-diaminodiphenyl sulfone, and mixtures thereof with their isomers.

(4-3) Aromatic polyamines having a nuclear-substituted electron withdrawing group (e.g., a halogen such as Cl, Br, I, or F, an alkoxy group such as methoxy or ethoxy group, nitro group), such as methylenebis-o-chloroaniline, 4-chloro-o-phenylenediamine, 2-chloro-1,4-phenylenediamine, 3-amino-4-chloroaniline, 4-bromo-1,3-phenylenediamine, 2,5-dichloro-1,4-phenylenediamine, 5-nitro-1,3-phenylenediamine, 3-dimethoxy-4-aminoaniline, 4,4'-diamino-3,3'-dimethyl-5,5'-dibromo-diphenylmethane, 3,3-dichlorobenzidine, 3,3-dimethoxybenzidine, bis(4-amino-3-chlorophenyl) oxide, bis(4-amino-2-chlorophenyl) propane, bis(4-amino-2-chlorophenyl)sulfone, bis(4-amino-3-methoxyphenyl)decane, bis(4-aminophenyl)sulfide bis(4-aminophenyl)telluride, bis(4-aminophenyl)selenide, bis(4-amino-3-methoxyphenyl)disulfide, 4,4-methylenebis(2-iodoaniline), 4,4-methylenebis(2-bromoaniline), 4,4-methylenebis(2-fluoroaniline), and 4-aminophneyl-2-chloroaniline.

(4-4) Aromatic polyamines having a secondary amino group, i.e., the above aromatic polyamines (4-1) to (4-3) in which part or all of —NH$_2$ groups are substituted with —NH—R' groups (R' represents an alkyl group such as methyl or ethyl group), such as 4,4-di(methylamino)diphenylmethane and 1-methyl-2-methylamino-4-aminobenzene; polyamide polyamines, such as a low-molecular-weight polyamide polyamine obtained from condensation between a dicarboxylic acid (e.g., dimer acid) and an excessive amount of (i.e., 2 mol or more per 1 mol of the acid) a polyamine (e.g., an alkylenediamine, a polyalkylenediamine); and polyether polyamines, such as a hydride of a cyanoethylation product of a polyether polyol (e.g., a polyalkylene glycol).

A reaction terminator (βs) may be optionally used in combination with the compound (β) having an active hydrogen group. Combination use of the reaction terminator (βs) and the compound (β) having an active hydrogen group at a specific ratio properly adjusts the molecular weight of the resin obtained from a reaction between the prepolymer (α) having a reactive group and the compound (β) having an active hydrogen group.

Specific examples of the reaction terminator (βs) include, but are not limited to, monoamines (e.g., diethylamine, dibutylamine, laurylamine, monoethanolamine, diethanolamine), blocked monoamines (e.g., ketimine compounds), monools (e.g., methanol, ethanol, isopropanol, butanol, phenol), monomercaptans (e.g., butylmercaptan, laurylmercaptan), monoisocyanates (e.g., lauryl isocyanate, phenyl isocyanate), and monoepoxides (e.g., butyl glycidyl ether).

In some embodiments, the ratio [α]/[β] of the equivalent amount [α] of reactive groups in the prepolymer (α) having a reactive group to the equivalent amount [β] of active hydrogen groups in the compound (β) having an active hydrogen group is 1/2 to 2/1, 1.5/1 to 1/1.5, or 1.2/1 to 1/1.2. The water (βd) as the compound (β) having an active hydrogen group is regarded as a divalent compound having an active hydrogen group.

In the above manufacturing method (I), the aqueous medium may include a water-miscible organic solvent (e.g., acetone, methyl ethyl ketone) other than water. The kind and content of water-miscible organic solvent are not particularly limited so long as granulation process of resin particles is not disturbed. In some embodiments, the aqueous medium includes a water-miscible organic solvent, which can be removed by drying without remaining in the resulting resin particles, in an amount of 40% by weight or less based on total weight of the aqueous medium.

Specific examples of usable organic solvents for preparing the toner components liquid in the manufacturing method (I) include, but are not limited to, aromatic hydrocarbon solvents, such as toluene, xylene, ethylbenzene, and tetralin; aliphatic or alicyclic hydrocarbon solvents such as n-hexane, n-heptane, and mineral spirit cyclohexane; halogen solvents, such as methyl chloride, methyl bromide, methyl iodide, methylene dichloride, carbon tetrachloride, trichloroethylene, and perchloroethylene; ester or ester ether solvents, such as ethyl acetate, butyl acetate, methoxybutyl acetate, methyl cellosolve acetate, and ethyl cellosolve acetate; ether solvents, such as diethyl ether, tetrahydrofuran, dioxane, ethyl cellosolve, butyl cellosolve, and propylene glycol monomethyl ether; ketone solvents, such as acetone, methyl ethyl ketone, methyl isobutyl ketone, di-n-butyl ketone, and cyclohexanone; alcohol solvents, such as methanol, ethanol, n-propanol, isopropanol, n-butanol, isobutanol, t-butanol, 2-ethylhexyl alcohol, and benzyl alcohol; amide solvents, such as dimethylformamide and dimethylacetamide; sulfoxide solvents such as dimethylsulfoxide; and heterocyclic compound solvents, such as N-methylpyrrolidone. Two or more of these organic solvents can be used in combination.

In the manufacturing method (I), an emulsifier or dispersant may be used for emulsifying or dispersing toner components. Any surfactant or water-soluble polymer can be used as the emulsifier or dispersant. The above-described organic solvent or any plasticizer can be used in combination as an auxiliary emulsifier or dispersant. Usable surfactants include anionic surfactants, cationic surfactants, ampholytic surfactants, and nonionic surfactants. Two or more kinds of surfactants can be used in combination.

Specific examples of usable anionic surfactants include, but are not limited to, carboxylic acids or salts thereof, sulfate salts, carboxymethylated salts, sulfonates, and phosphate salts.

Specific examples of the carboxylic acids include, but are not limited to, saturated or unsaturated fatty acids having 8 to 22 carbon atoms, such as capric acid, lauric acid, myristic acid, palmitic acid, stearic acid, arachidic acid, behenic acid, oleic acid, linoleic acid, ricinoleic acid; and mixtures of higher fatty acids obtained by saponifying palm oil, palm kernel oil, rice bran oil, or beef tallow. Their salts include sodium salts, potassium salts, amine salts, ammonium salts, quaternary ammonium salts, and alkanolamine salts (e.g., monoethanolamine salts, diethanolamine salts, triethanolamine salts).

Specific examples of the sulfate salts include, but are not limited to, higher alcohol sulfate salts (i.e., sulfate salts of aliphatic alcohols having 8 to 18 carbon atoms), higher alkyl ether sulfate salts (i.e., sulfate salts of EO or PO 1-10 mol adducts of aliphatic alcohols having 8 to 18 carbon atoms), sulfated oils (obtained by sulfating and neutralizing natural unsaturated fats or waxes having 12 to 50 carbon atoms), sulfated fatty acid esters (obtained by sulfating and neutralizing lower alcohol (C1-C8) esters of unsaturated fatty acids (C6-C40)), and sulfated olefins (obtained by sulfating and neutralizing olefins having 12 to 18 carbon atoms).

Their salts include sodium salts, potassium salts, amine salts, ammonium salts, quaternary ammonium salts, and alkanolamine salts (e.g., monoethanolamine salts, diethanolamine salts, triethanolamine salts).

Specific examples of the higher alcohol sulfate salts include, but are not limited to, octyl alcohol sulfate salt, decyl alcohol sulfate salt, lauryl alcohol sulfate salt, stearyl alcohol sulfate salt, sulfate salts of alcohols obtained using Ziegler catalysts (e.g., ALFOL 1214 available from CONDEA), and sulfate salts of alcohols obtained by oxo methods (e.g., DOBANOL 23, 25, and 45 and DIADOL 115, 115H, and 135 available from Mistubishi Chemical Corporation; TRIDECANOL available from KH Neochem Co., Ltd.; and OXO-COL 1213, 1215, and 1415 available from Nissan Chemical). Specific examples of the higher alkyl ether sulfate salts include, but are not limited to, sulfate salt of EO 2 mol adduct of lauryl alcohol and sulfate salt of EO 3 mol adduct of octyl alcohol. Specific examples of the sulfated oils include, but are not limited to, salts of sulfated castor oil, sulfated peanut oil, sulfated canola oil, sulfated beef tallow, and sulfated mutton tallow. Specific examples of the sulfated fatty acid esters include, but are not limited to, salts of sulfated butyl oleate and sulfated butyl ricinoleate. Specific examples of the sulfated olefin include, but are not limited to, TEEPOL (available from Shell Chemical Co.).

Specific examples of the carboxymethylated salts include, but are not limited to, carboxymethylated salts of aliphatic alcohols having 8 to 16 carbon atoms and carboxymethylated salts of EO or PO 1-10 mol adducts of aliphatic alcohols having 8 to 16 carbon atoms.

Specific examples of the carboxymethylated salts of the aliphatic alcohols include, but are not limited to, octyl alcohol carboxymethylated sodium salt, lauryl alcohol carboxymethylated sodium salt, carboxymethylated sodium salt of DOBANOL 23, and tridecanol carboxymethylated sodium salt.

Specific examples of the carboxymethylated salts of EO or PO 1-10 mol adducts of aliphatic alcohols include, but are not limited to, carboxymethylated sodium salt of EO or PO 3 mol adduct of octyl alcohol, carboxymethylated sodium salt of EO or PO 4 mol adduct of lauryl alcohol, and carboxymethylated sodium salt of EO or PO 5 mol adduct of tridecanol.

Specific examples of the sulfonates include, but are not limited to, alkylbenzene sulfonates, alkylnaphthalene sulfonates, sulfosuccinate diester salts, and sulfonates of IGEPON T or aromatic compounds. Specific examples of the alkylbenzene sulfonate include, but are not limited to, sodium dodecylbenzene sulfonate. Specific examples of the alkylnaphthalene sulfonate include, but are not limited to, sodium dodecylnaphthalene sulfonate. Specific examples of the sulfosuccinate diester salts include, but are not limited to, sulfosuccinate di-2-ethylhexyl ester sodium salt. Specific examples of the sulfonates of aromatic compounds include, but are not limited to, monosulfonate and disulfonate of alkylated diphenyl ethers and styrenated phenol sulfonate.

Specific examples of the phosphate salts include, but are not limited to, higher alcohol phosphate salts and phosphate salts of EO adducts of higher alcohols. Specific examples of the higher alcohol phosphate salts include, but are not limited to, lauryl alcohol phosphate monoester disodium salt and lauryl alcohol phosphate diester disodium salt. Specific examples of the phosphate salts of EO adducts of higher alcohols include, but are not limited to, monoester disodium salt of EO 5 mol adduct of oleyl alcohol phosphate. Specific examples of usable cationic surfactants include, but are not limited to, quaternary ammonium salt surfactants and amine salt surfactants.

A quaternary ammonium salt surfactant can be obtained by reacting a tertiary amine having 3 to 40 carbon atoms with a quaternization agent (e.g., an alkylation agent such as methyl chloride, methyl bromide, ethyl chloride, benzyl chloride, and dimethyl sulfate; ethylene oxide). Specific examples of such quaternary ammonium salt surfactants include, but are not limited to, lauryl trimethyl ammonium chloride, didecyl dimethyl ammonium chloride, dioctyl dimethyl ammonium bromide, stearyl trimethyl ammonium bromide, lauryl dimethyl benzyl ammonium chloride (benzalkonium chloride), cetyl pyridinium chloride, polyoxyethylene trimethyl ammonium chloride, and stearamidoethyl diethyl methyl ammonium methosulfate.

An amine salt surfactant can be obtained by neutralizing a primary, secondary, or tertiary amine with an inorganic acid (e.g., hydrochloric acid, nitric acid, sulfuric acid, hydroiodic acid, phosphoric acid, perchloric acid) or an organic acid (e.g., acetic acid, formic acid, lactic acid, gluconic acid, adipic acid, alkyl phosphoric acid having 2 to 24 carbon atoms, malic acid, citric acid). Specific examples of primary amine salt surfactants include, but are not limited to, inorganic and organic acid salts of aliphatic higher amines having 8 to 40 carbon atoms (e.g., lauryl amine, stearyl amine, cetyl amine, hardened beef tallow amine, rosin amine) and salts of higher fatty acids having 8 to 40 carbon atoms (e.g., stearic acid, oleic acid) with lower amines having 2 to 6 carbon atoms. Specific examples of secondary amine salt surfactants include, but are not limited to, inorganic and organic acid salts of EO adducts of aliphatic amines having 4 to 40 carbon atoms. Specific examples of tertiary amine salt surfactants include, but are not limited to, inorganic and organic acid salts of aliphatic amines having 4 to 40 carbon atoms (e.g., triethylamine, ethyldimethylamine, N,N,N',N'-tetramethylethylenediamine), EO adducts (2 mol or more) of aliphatic amines having 2 to 40 carbon atoms, alicyclic amines having 6 to 40 carbon atoms (e.g., N-methylpyrrolidine, N-methylpiperidine, N-meyhylhexamethyleneimine, N-methylmorpholine, 1,8-diazabicyclo(5,4,0)-7-undecene), and nitrogen-containing heterocyclic aromatic amines having 5 to 30 carbon atoms (e.g., 4-dimethylaminopyridine, N-methylimidazole, 4,4'-dipyridyl); and inorganic and organic acid salts of tertiary amines, such as triethanolamine monostearate and stearamidoethyl diethyl methyl ethanolamine.

Specific examples of usable ampholytic surfactants include, but are not limited to, carboxylate ampholytic surfactants, sulfate salt ampholytic surfactants, sulfonate ampholytic surfactants, and phosphate salt ampholytic surfactants.

Specific examples of the carboxylate ampholytic surfactants include, but are not limited to, amino acid ampholytic surfactants, betaine ampholytic surfactants, and imidazoline ampholytic surfactants.

An amino acid ampholytic surfactant has both amino group and carboxyl group per molecule, and is represented by the following formula:

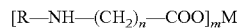

[R—NH—(CH$_2$)$_n$—COO]$_m$M wherein R represents a monovalent hydrocarbon group, n represents an integer of 1 or 2, m represents an integer of 1 or 2, and M represents a hydrogen ion, an alkali metal ion, an alkali earth metal ion, an ammonium cation, an amine cation, or an alkanolamine cation.

Specific examples of such amino acid ampholytic surfactants include, but are not limited to, alkyl(C6-C40) aminopropionic acid ampholytic surfactants (e.g., sodium stearyl aminopropionate, sodium lauryl aminopropionate) and alkyl (C4-C24) aminoacetic acid ampholytic surfactants (e.g., sodium lauryl aminoacetate).

A betaine ampholytic surfactant has both a quaternary-ammonium-salt-based cationic site and a carboxylic-acid-based anionic site per molecule. Specific examples of such betaine ampholytic surfactants include, but are not limited to, alkyl(C6-C40) dimethyl betaines (e.g., stearyl dimethyl aminoacetic betaine, lauryl dimethyl aminoacetic betaine), amide betaines having 6 to 40 carbon atoms (e.g., palm oil fatty acid amide propyl betaine), and alkyl(C6-C40) dihydroxyalkyl (C6-C40) betaines (e.g., lauryl dihydroxyethyl betaine).

An imidazoline ampholytic surfactant has an imidazoline-ring-based cationic site and a carboxylic-acid-based anionic site per molecule. Specific examples of such imidazoline ampholytic surfactants include, but are not limited to, 2-undecyl-N-carboxymethyl-N-hydroxyethyl imidazolinium betaine.

Usable ampholytic surfactants further include glycine ampholytic surfactants such as lauroyl glycine sodium salt, lauryl diaminoethyl glycine sodium salt, lauryl diaminoethyl glycine hydrochloride, dioctyl diaminoethyl glycine hydrochloride; sulfobetaine ampholytic surfactants such as pentadecyl sulfotaurine; sulfonate ampholytic surfactants; and phosphate salt ampholytic surfactants.

Specific examples of usable nonionic surfactants include, but are not limited to, alkylene oxide (AO) adduct nonionic surfactants and polyol nonionic surfactants.

An AO adduct nonionic surfactant can be obtained by directly adding an AO(C2-C20) to a higher alcohol, higher fatty acid, or alkylamine having 8 to 40 carbon atoms; reacting a higher fatty acid with a polyalkylene glycol obtained by adding an AO to glycol; adding an AO to an esterification product between a polyol and a higher fatty acid; or adding an AO to a high fatty acid amide.

The alkylene oxide (AO) may be ethylene oxide (EO), propylene oxide (PO), or butylene oxide (BO), for example. In some embodiments, EO adduct or EO-PO random or block adduct is employed. In some embodiments, the added amount of AO is 10 to 50 mol. In some embodiments, AO includes 50 to 100% of EO.

Specific examples of the AO adduct nonionic surfactants include, but are not limited to, oxyalkylene(C2-C24) alkyl (C8-C40) ethers (e.g., EO 20 mol adduct of octyl alcohol, EO 20 mol adduct of lauryl alcohol, EO 10 mol adduct of stearyl alcohol, EO 5 mol adduct of oleyl alcohol, EO 10 mol PO 20 mol block adduct of lauryl alcohol); polyoxyalkylene(C2-C24) higher fatty acid(C8-C40) esters (e.g., EO 10 mol adduct of stearic acid, EO 10 mol adduct of lauric acid); polyoxyalkylene(C2-C24) polyol(C3-C40) higher fatty acid (C8-C40) esters (e.g., polyethylene glycol (polymerization degree=20) laurate diester, polyethylene glycol (polymerization degree=20) oleate diester); polyoxyalkylene(C2-C24) alkyl(C8-C40) phenyl ethers (e.g., EO 4 mol adduct of nonyl phenol, EO 8 mol PO 20 mol block adduct of nonyl phenol, EO 10 mol adduct of octyl phenol, EO 10 mol adduct of bisphenol A, EO 20 mol adduct of styrenated phenol); polyoxyalkylene(C2-C24) alkyl(C8-C40) amino ethers (e.g., EO 10 mol adduct of laurylamine, EO 10 mol adduct of stearylamine); and polyoxyalkylene(C2-C24) alkanolamides(C8-C24:acyl site) (e.g., EO 10 mol adduct of hydroxyethyl lauric acid amide, EO 20 mol adduct of hydroxypropyl oleic acid amide).

Specific examples of the polyol nonionic surfactants include, but are not limited to, polyol fatty acid esters, AO adducts of polyol fatty acid esters, polyol alkyl ethers, and AO adducts of polyol alkyl ethers. The carbon number of the polyol, fatty acid, and AO may be 3 to 24, 8 to 40, and 2 to 24, respectively.

Specific examples of the polyol fatty acid esters include, but are not limited to, pentaerythritol monolaurate, pentaerythritol monooleate, sorbitan monolaurate, sorbitan monostearate, sorbitan dilaurate, sorbitan dioleate, and sucrose monostearate.

Specific examples of the AO adducts of polyol fatty acid esters include, but are not limited to, EO 10 mol adduct of ethylene glycol monooleate, EO 20 mol adduct of ethylene glycol monostearate, EO 20 mol PO 10 mol random adduct of trimethylolpropane monostearate, EO 10 mol adduct of sorbitan monolaurate, EO 20 mol adduct of sorbitan distearate, and EO 12 mol PO 24 mol random adduct of sorbitan dilaurate.

Specific examples of the polyol alkyl ethers include, but are not limited to, pentaerythritol monobutyl ether, pentaerythritol monolauryl ether, sorbitan monomethyl ether, sorbitan monostearyl ether, methyl glycoside, and lauryl glycoside.

Specific examples of the AO adducts of polyol alkyl ethers include, but are not limited to, EO 10 mol adduct of sorbitan monostearyl ether, EO 20 mol PO 10 mol random adduct of methyl glycoside, EO 10 mol adduct of lauryl glycoside, and EO 20 mol PO 20 mol random adduct of stearyl glycoside.

Specific examples of usable water-soluble polymers include, but are not limited to, cellulose compounds (e.g., methyl cellulose, ethyl cellulose, hydroxyethyl cellulose, ethyl hydroxyethyl cellulose, carboxymethyl cellulose, hydroxypropyl cellulose, and saponified products thereof), gelatin, starch, dextrin, gum arabic, chitin, chitosan, polyvinyl alcohol, polyvinyl pyrrolidone, polyethylene glycol, polyethyleneimine, polyacrylamide, acrylate-containing polymers (e.g., sodium polyacrylate, potassium polyacrylate, ammonium polyacrylate, polyacrylic acids partially neutralized with sodium hydroxide, sodium acrylate-acrylate copolymer), styrene-maleic anhydride copolymers (partially) neutralized with sodium hydroxide, and water-soluble polyurethanes (e.g., reaction products of polyethylene glycols or polycaprolactone diol with polyisocyanate).

The toner particles may be further mixed with an additive such as inorganic fine particles (e.g., hydrophobized silica powder) to improve fluidity, storage stability, developability, and transferability of the toner.

The toner particles and additive can be mixed by a powder mixer which may be equipped with a jacket for controlling inner temperature. To vary load history given to the additive, the additive may be gradually added from the initial stage of mixing or added from the middle of the mixing, while optionally varying the revolution, rotating speed, time, and temperature of the mixer. The additive may be first applied with strong load and subsequently weak load, or vice versa. Specific examples of usable mixers include, but are not limited to, a V-type mixer, a Rocking mixer, a Loedige mixer, a Nauta mixer, and a Henschel mixer. Undesired coarse or aggregated particles are removed by a 250-mesh sieve.

The toner according to an embodiment is not limited in its properties, such as shape and size.

In some embodiments, the toner has an average circularity of 0.900 to 0.980 or 0.950 to 0.975. The circularity is defined as the ratio of the perimeter of a circle having the same area as a projected image of a toner particle to the perimeter of the projected image of the toner particle. In some embodiments, the toner includes particles having a circularity less than 0.94 in an amount of 15% or less.

When the average circularity is less than 0.900, transferability of the toner may be poor and therefore high-quality images cannot be obtained. When the average circularity is greater than 0.980, such toner particles may not be sufficiently removed from a photoreceptor or a transfer belt in image forming systems employing a blade cleaning member. For example, when toner particles remain on a photoreceptor without being transferred onto paper due to the occurrence of paper jam, especially in forming an image having a high image area ratio such as a photographic image, such residual toner particles may undesirably retransferred onto background portions of a next image. Alternatively, such residual toner particles may contaminate and deteriorate a charging roller for charging the photoreceptor.

The average circularity of toner can be determined using a flow particle image analyzer FPIA-2100 (from Sysmex Corporation) and an analysis software FPIA-2100 Data Processing Program for FPIA version 00-10 as follows. First, charge a 100-mL glass beaker with 0.1 to 0.5 mL of a 10% by weight surfactant (an alkylbenzene sulfonate NEOGEN SC-A from Dai-ichi Kogyo Seiyaku Co., Ltd.). Add 0.1 to 0.5 g of a toner to the beaker and mix with a micro spatula. Further add 80 mL of ion-exchange water to the beaker. Subject the resulting dispersion to a dispersion treatment for 3 minutes using an ultrasonic disperser (from Honda Electronics). Subject the dispersion, having a concentration of 5,000 to 15,000 particles per micro-liter, to a measurement of shape distribution by FPIA-2100. In terms of measurement reproducibility, it is important that the dispersion has a concentration of 5,000 to 15,000 particles per micro-liter. To make the dispersion have the desired concentration, the amounts of surfactant and toner included in the dispersion are adjusted. When the amount of surfactant in the dispersion is too large, noisy bubbles may be undesirably generated. When the amount of surfactant in the dispersion is too small, toner particles cannot sufficiently get wet or dispersed. The proper amount of toner in the dispersion depends on particle diameter of toner. The smaller the particle diameter of toner, the smaller the proper amount of the toner. When a toner has a particle diameter of 3 to 10 μm, 0.1 to 0.5 g of the toner should be included in the dispersion so that the dispersion has a concentration of 5,000 to 15,000 particles per micro-liter.

In some embodiments, the toner has a volume average particle diameter of 3 to 10 μm or 3 to 8 μm. When the volume average particle diameter is less than 3 μm, such toner particles may undesirably fuse on the surfaces of carrier particles and degrade charging ability of the carrier particles after a long-term agitation in a developing device, when used for a two-component developer. When volume average particle diameter is greater than 10 μm, it may be difficult to produce high-resolution and high-quality images. Moreover, the average particle diameter of such toner particles in a developer may largely vary upon consumption and supply of the toner particles.

In some embodiments, the ratio of the volume average particle diameter to the number average particle diameter of the toner is 1.00 to 1.25 or 1.10 to 1.25.

Volume average particle diameter and number average particle diameter of toner can be measured by a particle size analyzer MULTISIZER III (from Beckman Coulter, Inc.) having an aperture size of 100 μm and an analysis software program Beckman Coulter Multisizer 3 Version 3.51 as follows. First, charge a 100-mL glass beaker with 0.5 mL of a 10% by weight surfactant (an alkylbenzene sulfonate NEOGEN SC-A from Dai-ichi Kogyo Seiyaku Co., Ltd.). Add 0.5 g of a toner to the beaker and mix with a micro spatula. Further add 80 mL of ion-exchange water to the beaker. Subject the resulting dispersion to a dispersion treatment for 10 minutes using an ultrasonic disperser (W-113 MK-II from Honda Electronics). Subject the dispersion to a measurement by the MULTISIZER III using a measuring solution ISOTON III (from Beckman Coulter, Inc.). During the measurement, the dispersion is dropped so that the sample concentration becomes 8±2%. In terms of measurement reproducibility, it is important that the sample concentration is 8±2%.

A developer according to an embodiment includes the above-described toner according to an embodiment and other components such as a carrier. The developer may be either a one-component developer or a two-component developer. The two-component developer is compatible with high-speed printers, in accordance with recent improvement in information processing speed, owing to its long lifespan.

In the one-component developer according to an embodiment, the average toner size may not vary very much although consumption and supply of toner particles are repeated. Additionally, toner particles may not adhere or fix to a developing roller or a toner layer regulating blade. Thus, the one-component developer reliably provides stable developability and image quality for an extended period of time. In the two-component developer according to an embodiment, the average toner size may not vary very much although consumption and supply of toner particles are repeated. Thus, the two-component developer reliably provides stable developability for an extended period of time.

The carrier may comprise a core material and a covering layer that covers the core material. Specific materials usable as the core material include, but are not limited to, ferrite, magnetite, iron, and nickel. Specific examples of the ferrite include, but are not limited to, copper-zinc ferrite and environmentally-adaptable ferrites such as manganese ferrite, manganese-magnesium ferrite, manganese-strontium ferrite, manganese-magnesium-strontium ferrite, and lithium ferrite.

The core material may further include one or more elements such as Li, Na, K, Ca, Ba, Y, Ti, Zr, V, Ag, Ni, Cu, Zn, Al, Sn, Sb, and Bi, to control resistivity or to improve production stability. The content of these elements may be 5% by atom or less or 3% by atom or less based on total metal element content.

The covering layer includes a binder resin and optionally includes other materials such as fine particles. Specific examples of usable binder resins for the covering layer include, but are not limited to, cross-linked copolymers including polyolefin (e.g., polyethylene, polypropylene) or modified product thereof, styrene, acrylic resin, acrylonitrile, vinyl acetate, vinyl alcohol, vinyl chloride, vinyl carbazole, and/or vinyl ether; silicone resins comprising organosiloxane bonds and modified (e.g., alkyd-resin-modified, polyesterresin-modified, polyurethane-modified, polyimide-modified) products thereof; polyamides; polyesters; polyurethanes; polycarbonates; urea resins; melamine resins; benzoguanamine resins; epoxy resins; ionomer resins; polyimide resins; and derivatives of these materials. Two or more of these resins can be used in combination. In one or more embodiments, an acrylic resin and/or a silicone resin is used.

Acrylic resins have strong adhesiveness to the core material or fine particles included in the covering layer while having low brittleness. Therefore, acrylic resins effectively prevent the covering layer from peeling as well as the fine particles from separating from the covering layer. In particular, fine particles having a diameter greater than the covering layer thickness are more effectively prevented from separating from the covering layer due to the nature of acrylic resin.

In some embodiments, the acrylic resin has a glass transition temperature (Tg) of 20 to 100° C. or 25 to 80° C. Within the above Tg range, the binder resin expresses proper elasticity which reduces impact on the carrier particles upon frictional charging, resulting in prevention of peeling and abrasion of the covering layer.

A cross-linked product of an acrylic resin between an amino resin, as the binder resin, expresses proper elasticity while preventing coalescence of the covering layers (i.e., carrier blocking).

Specific examples of usable amino resins include, but are not limited to, melamine resins and benzoguanamine resins, both of which can improve charge giving ability of the resulting carrier.

To more properly control the charge giving ability of the resulting carrier, melamine and/or benzoguanamine resins may be used in combination with another amino resin. Acrylic resins cross-linkable with such amino resins may include hydroxyl group or carboxyl group. In some embodiments, an acrylic resin having hydroxyl group is used. Due to the presence of hydroxyl group, such acrylic resins have improved adhesiveness to both the core material and fine particles as well as more stabilized dispersing ability. In some embodiments, such acrylic resins have a hydroxyl value of 10 mgKOH/g or more or 20 mgKOH/g or more.

The binder resin which includes silicone units can advantageously reduce surface energy of the carrier particles and thereby prevents toner particles from adhering to or contaminating the surfaces of the carrier particles.

The silicone units may comprise, for example, methyltrisiloxane unit, dimethyldisiloxane unit, and/or trimethylsiloxane unit. The silicone units may be bound chemically to or blended with other binder resins. Alternatively, the silicone units may form a multilayer with other binder resins.

In a case in which the silicone units are blended with other binder resins or form a multilayer with other binder resins, the other binder resin may include a silicone resin and/or a modified product thereof. In particular, the use of a silicone resin having the following formula suppresses attrition, abrasion, and elimination of the binder resins.

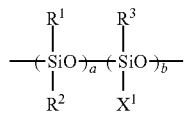

wherein each of $R^1$ to $R^3$ independently represents a hydrocarbon group or a derivative thereof, $X^1$ represents a condensation-reactive group, and a and b independently represents a positive integer.

The $X^1$ group may be, for example, hydroxyl group, alkoxy group, or methyl ethyl ketoxime group. The $X^1$ group causes a condensation reaction due to moisture in the air or upon application of heat and form a three-dimensional network structure. Specific examples of the silicone resins having the above formula include, but are not limited to, straight silicone resins consisting of organosiloxane bonds, and silicone resins modified with alkyd, polyester, epoxy, acrylic, or urethane.

Specific examples of commercially available straight silicone resins include, but are not limited to, KR271, KR272, KR282, KR252, KR255, and KR152 (available from Shin-Etsu Chemical Co., Ltd.); and SR2400, SR2405, and SR2406 (available from Dow Corning Toray Co., Ltd.). Specific examples of commercially available modified silicone resins include, but are not limited to, ES-1001N (epoxy-modified), KR-5208 (acrylic-modified), KR-5203 (polyester-modified), KR-206 (alkyd-modified), and KR-305 (urethane-modified) (available from Shin-Etsu Chemical Co., Ltd.); and SR2115 (epoxy-modified) and SR2110 (alkyd-modified) (available from Dow Corning Toray Co., Ltd.).

The silicone resin can be used alone or in combination with other components such as a cross-linkable component and a charge controlling component. Specific examples of usable cross-linkable components include, but are not limited to, silane coupling agents. Specific examples of the silane coupling agents include, but are not limited to, methyltrimethoxysilane, methyltriethoxysilane, octyltrimethoxysilane, and aminosilane coupling agents.

When the covering layer includes an aminosilane coupling agent, the carrier charge can be more properly controlled. Specific examples of usable aminosilane coupling agents are listed below.

| | |
|---|---|
| $H_2N(CH_2)_3Si(OCH_3)_3$ | MW 179.3 |
| $H_2N(CH_2)_3Si(OC_2H_5)_3$ | MW 221.4 |
| $H_2NCH_2CH_2CH_2Si(CH_3)_2(OC_2H_5)$ | MW 161.3 |
| $H_2NCH_2CH_2CH_2Si(CH_3)(OC_2H_5)_2$ | MW 191.3 |
| $H_2NCH_2CH_2NHCH_2Si(OCH_3)_3$ | MW 194.3 |
| $H_2NCH_2CH_2NHCH_2CH_2CH_2Si(CH_3)(OCH_3)_2$ | MW 206.4 |
| $H_2NCH_2CH_2NHCH_2CH_2CH_2Si(OCH_3)_3$ | MW 224.4 |
| $(CH_3)_2NCH_2CH_2CH_2Si(CH_3)(OC_2H_5)_2$ | MW 219.4 |
| $(C_4H_9)_2NC_3H_6Si(OCH_3)_3$ | MW 291.6 |

In some embodiments, the content of the aminosilane coupling agent in the covering layer is 0.001 to 30% by weight or 0.001 to 10% by weight. When the content is less than 0.001% by weight, chargeability may be easily influenced by environmental conditions and product yield may decrease. When the content is greater than 30% by weight, the covering layer may be too brittle to be resistant to abrasion.

Specific examples of fine particles to be included in the covering layer include, but are not limited to, inorganic fine particles such as metal powder, tin oxide, zinc oxide, silica, titanium oxide, alumina, potassium titanate, barium titanate, and aluminum borate; and organic fine particles such as conductive polymer particles (e.g., polyaniline, polyacetylene, polyparaphenylene, poly(paraphenylene sulfide), polypyrrole, parylene) and carbon black. Two or more of these materials can be used in combination.

The surfaces of these fine particles may be subjected to a conductive treatment. For example, the fine particles may be covered with aluminum, zinc, copper, nickel, silver, alloys thereof, zinc oxide, titanium oxide, tin oxide, antimony oxide, indium oxide, bismuth oxide, tin-doped indium oxide, or antimony-doped tin oxide or zirconium oxide, in the form of solid solution or fusion, to have conductivity. In some embodiments, tin oxide, indium oxide, or tin-doped indium oxide is used for the conductive treatment.

In some embodiments, the fine particles have a volume average particle diameter of 1 μm or less. When the volume average particle diameter is greater than 1 μm, it may be difficult for the covering layer to retain the fine particles and therefore the fine particles may be easily detached from the covering layer, resulting in deterioration of the strength of the covering layer. Volume average particle diameter of the fine particles can be measured by a layer Doppler/dynamic light scattering particle size analyzer, for example.

In some embodiments, the content of the covering layer in the carrier is 5% by weight or more or 5 to 10% by weight.

In some embodiments, the covering layer has a thickness of 0.1 to 5 μm or 0.3 to 2 μm. The thickness of the covering layer can be measured by, for example, preparing cross-sections of carrier particles with a focused ion beam (FIB) and observing 50 or more of the prepared cross-sections with a transmission electron microscope (TEM) or scanning transmission electron microscope (STEM) to measure and average the thicknesses of each covering layer.

The covering layer may be formed by, for example, applying a covering layer liquid that is containing all of the above-described materials to be included in the covering layer such as a binder resin and or precursor thereof, to the surface of the core material by a spraying or dipping method. In some embodiments, the core material applied with the covering layer liquid is subjected to a heating treatment so as to accelerate a polymerization reaction of the binder resin or precursor thereof. The heating treatment may be performed with a coating equipment which has applied the covering layer on the core material, or alternatively performed with another heating equipment such as electric furnace or burning kiln.

In some embodiments, the heating temperature is 120 to 350° C. In some embodiments, the heating temperature is equal to or less than the decomposition temperature of the materials included in the covering layer. In some embodiments, the decomposition temperature of the materials in the covering layer is 220° C. or less and the heating time period is 5 to 120 minutes.

In some embodiments, the carrier has a volume average particle diameter of 10 to 100 μm or 20 to 65 μm. When the volume average particle diameter is less than 10 μm, carrier deposition may occur due to unevenness of the core particles. When the volume average particle diameter is greater than 100 μm, thin lines may not be precisely reproduced in the resulting image. Volume average particle diameter can be measured by a Microtrac particle size analyzer HRA9320-X100 (from Nikkiso Co., Ltd.), for example.

In some embodiments, the carrier has a volume resistivity of 9 to 16 log(Ω·cm) or 10 to 14 log(Ω·cm). When the volume resistivity is less than 9 log(Ω·cm), carrier deposition may occur in non-image area. When the volume resistivity is greater than 16 log(Ω·cm), the edge effect may occur. The edge effect is a phenomenon in which the edge of a latent image is developed into a high-density image while the center of the latent image is developed into a low-density image. Volume resistivity may be arbitrarily controlled by controlling the thickness of the covering layer or the content of the conductive fine particles included in the covering layer.

Volume resistivity can be measured as follows, for example. First, fill a measuring cell with a carrier. The measuring cell is comprised of a fluorocarbon-resin container, and electrodes each having a surface area of 2.5 cm×4 cm are disposed within the cell forming a distance of 0.2 cm therebetween. Tap the measuring cell filled with the carrier from a height of 1 cm at a tapping speed of 30 times/min for 10 times. Next, supply a direct current voltage of 1,000 V between the electrodes for 30 seconds. Thereafter, measure a resistance r (Ω) by a high resistance meter 4329A (from Hewlett-Packard Japan. Ltd.). Volume resistivity is calculated from the following equation.

$$R = \text{Log}[r(\Omega) \times (2.5(\text{cm}) \times 4(\text{cm})/0.2(\text{cm})]$$

In some embodiments, the two-component developer includes the toner in an amount of 2.0 to 12.0% by weight or 2.5 to 10.0% by weight based on the weight of the carrier.

The developer according to an embodiment may be contained in a container. The container may comprise a main body and a lid.

The main body is not limited in size, shape, structure, and material. In one or more embodiments, the main body is comprised of a cylinder, on the inner peripheral surface of which concavities and convexities are formed in a spiral manner, so that the developer is conveyed to a discharge outlet as the main body rotates. At least a part of the spiral concavities and convexities has a function of accordion. Specific examples of usable materials for the container include, but are not limited to, resins providing high dimension accuracy, such as polyester resin, polyethylene resin, polypropylene resin, polystyrene resin, polyvinyl chloride resin, polyacrylic acid resin, polycarbonate resin, ABS resin, and polyacetal resin.

The container containing the developer is easy to store, convey, or handle. The container may be detachably attached to image forming apparatus to supply the developer thereto.

An image forming method according to an embodiment includes at least an electrostatic latent image forming process, a developing process, a transfer process, and a fixing process. The image forming method may optionally include other processes such as a neutralization process, a cleaning process, a recycle process, and a control process, if needed.

An image forming apparatus for practicing the image forming method according to an embodiment include an electrostatic latent image bearing member, an electrostatic latent image forming device, a developing device, a transfer device, and a fixing device. The image forming apparatus may optionally include other members, such as a neutralizer, a cleaner, a recycler, and a controller, if needed.

The electrostatic latent image forming process is a process which forms an electrostatic latent image on an electrostatic latent image bearing member.

The electrostatic latent image bearing member (hereinafter may be referred to as "electrophotographic photoreceptor" or "photoreceptor") is not limited in material, shape, structure, and size. In some embodiments, the electrostatic latent image bearing member has a drum-like shape and is comprised of an inorganic photoconductor, such as amorphous silicone or selenium, or an organic photoconductor, such as polysilane or phthalopolymethyne. Amorphous silicone is advantageous in terms of long lifespan.

In the electrostatic latent image forming process, an electrostatic latent image is formed by the electrostatic latent image forming device. The electrostatic latent image forming device comprises a charger for uniformly charging a surface of the electrostatic latent image bearing member and an irradiator for irradiating the charged surface with light containing image information.

The charger is adapted to charge a surface of the electrostatic latent image bearing member by supplying a voltage thereto. The charger may be, for example, a contact charger equipped with a conductive or semiconductive roll, brush, film, or rubber blade, or a non-contact charger such as corotron and scorotron that use corona discharge. In some embodiments, the charger is disposed in contact or non-contact with the electrostatic latent image bearing member so as to supply an AC-DC superimposed voltage to a surface of the electrostatic latent image bearing member. In some embodiments, the charger is a non-contact charging roller disposed proximal to the electrostatic latent image bearing member, adapted to to supply an AC-DC superimposed voltage to a surface of the electrostatic latent image bearing member.

The irradiator is adapted to irradiate the charged surface of the electrostatic latent image bearing member with light containing image information. The irradiator may be, for example, a radiation optical type, a rod lens array type, a laser optical type, or a liquid crystal shutter optical type.

The electrostatic latent image bearing member may be irradiated with light from the reverse surface (back surface) side thereof.

The developing process is a process which develops the electrostatic latent image into a toner image that is visible with the developer according to an embodiment. In some embodiments, the developing device includes a container for containing the developer according to an embodiment and a developer bearing member adapted to supply the developer to the electrostatic latent image with or without contacting the electrostatic latent image.

The developing device may be either a single-color developing device or a multi-color developing device. The developing device may be comprised of an agitator for frictionally agitating and charging the developer and a rotatable magnet roller.

In these embodiments, toner particles and carrier particles are mixed and agitated within the developing device so that the toner particles are frictionally charged. The charged toner particles and carrier particles are borne on the surface of the magnet roller forming chainlike aggregations (hereinafter "magnetic brush"). The magnet roller is disposed adjacent to the electrostatic latent image bearing member. Therefore, a part of the toner particles in the magnetic brush migrates from the surface of the magnet roller to the surface of the electrostatic latent image bearing member due to electrical attractive force. As a result, the electrostatic latent image formed on the electrostatic latent image bearing member is developed into a toner image.

The transfer process is a process which transfers the toner image onto a recording medium. In some embodiments, the toner image is primarily transferred onto an intermediate transfer medium and secondarily transferred onto the recording medium. In some embodiments, a plurality of toner images with different colors is primarily transferred onto the intermediate transfer medium to form a composite toner image and the composite toner image is secondarily transferred onto the recording medium.

The toner image may be transferred from the electrostatic latent image bearing member upon charging of the electrostatic latent image bearing member by a transfer charger. In some embodiments, the transfer device includes a plurality of primary transfer devices each adapted to transfer a toner image onto the intermediate transfer medium to form a composite toner image, and a secondary transfer device adapted to transfer the composite toner image onto the recording medium. The intermediate transfer medium may be, for example, a transfer belt.

In some embodiments, each transfer device (including the primary transfer device and the secondary transfer device) contains a transfer unit adapted to separate a toner image from the electrostatic latent image bearing member toward a recording medium side. The number of transfer devices is not limited, i.e., one or more.

The transfer unit may be, for example, a corona discharger, a transfer belt, a transfer roller, a pressure transfer roller, or an adhesive transfer unit.

The recording medium is not limited to a specific material, and any kind of material can be used as the recording medium.

The fixing process is a process which fixes the toner image on a recording medium. Each single-color toner image may be independently fixed on a recording medium, or alternatively, a composite toner image including a plurality of color toner images may be fixed on a recording medium at once.

In some embodiments, the fixing device includes fixing members adapted to fix a toner image by application of heat and pressure. For example, the fixing device may include a combination of a heating roller and a pressing roller, or a combination of a heating roller, a pressing roller, and an endless belt.

In some embodiments, the fixing device includes a heater equipped with a heating element, a film in contact with the heater, and a pressing member pressed against the heater with the film therebetween. Such a fixing device is adapted to pass a recording medium having a toner image thereon between the film and the pressing member so that the toner image is fixed on the recording medium upon application of heat and pressure. In some embodiments, the heating member is heated to a temperature of 80 to 200° C.

In the fixing process, an optical fixer can be used in place of or in combination with the fixing device.

The neutralization process is a process in which the neutralizer neutralizes the electrostatic latent image bearing member by supplying a neutralization bias thereto. The neutralizer may be, for example, a neutralization lamp.

The cleaning process is a process in which the cleaner removes residual toner particles remaining on the electrostatic latent image bearing member. The cleaner may be, for example, a magnetic brush cleaner, an electrostatic brush cleaner, a magnetic roller cleaner, a blade cleaner, a brush cleaner, or a web cleaner.

The recycle process is a process in which the recycler supplies the residual toner particles collected in the cleaning process to the developing device. The recycler may be, for example, a conveyer.

The control process is a process in which the controller controls the above-described processes. The controller may be, for example, a sequencer or a computer.

FIG. 1 is a schematic view of an image forming apparatus according to an embodiment. An image forming apparatus 100A includes a photoreceptor drum 10 serving as an electrostatic latent image bearing member, a charging roller 20, an irradiator, a developing device 40, an intermediate transfer belt 50, a cleaning device 60, and a neutralization lamp 70.

An intermediate transfer belt 50 is a seamless belt stretched taut with three rollers 51 and is movable in a direction indicated by arrow in FIG. 1. One of the three rollers 51 is adapted to supply a primary transfer bias to the intermediate transfer belt 50. A cleaner 90 is disposed adjacent to the intermediate transfer belt 50. A transfer roller 80 is disposed facing the intermediate transfer belt 50. The transfer roller 80 is adapted to supply a secondary transfer bias for transferring a toner image onto a recording medium 95. A corona charger 58 is disposed facing the intermediate transfer belt 50 between the contact points of the intermediate transfer belt 50 with the photoreceptor drum 10 and the recording medium 95 with respect to the direction of rotation of the intermediate transfer belt 50.

The developing device 40 includes a black developing unit 45K, an yellow developing unit 45Y, a magenta developing unit 45M, and a cyan developing unit 45C. The developing units 45K, 45Y, 45M, and 45C include respective developer containers 42K, 42Y, 42M, and 42C, respective developer supply rollers 43K, 43Y, 43M, and 43C, and respective developing rollers 44K, 44Y, 44M, and 44C.

The image forming apparatus 100A is adapted to produce an image in the manner described below.

In the image forming apparatus 100A, the photoreceptor drum 10 is uniformly charged by the charging roller 20 and then irradiated with a light beam L containing image information emitted from the irradiator so that an electrostatic latent image is formed on the photoreceptor drum 10. The developing device 40 supplies toner to the electrostatic latent image on the photoreceptor drum 10 to form a toner image. The toner image is primarily transferred onto the intermediate transfer belt 50 by a transfer bias supplied from the roller 51 and is secondarily transferred onto the recording medium 95 by a transfer bias supplied from the transfer roller 80. Residual toner particles remaining on the photoreceptor drum 10 without being transferred onto the intermediate transfer belt 50 are removed by the cleaning device 60. The photoreceptor drum 10 is neutralized by the neutralization lamp 70.

Figure 2:
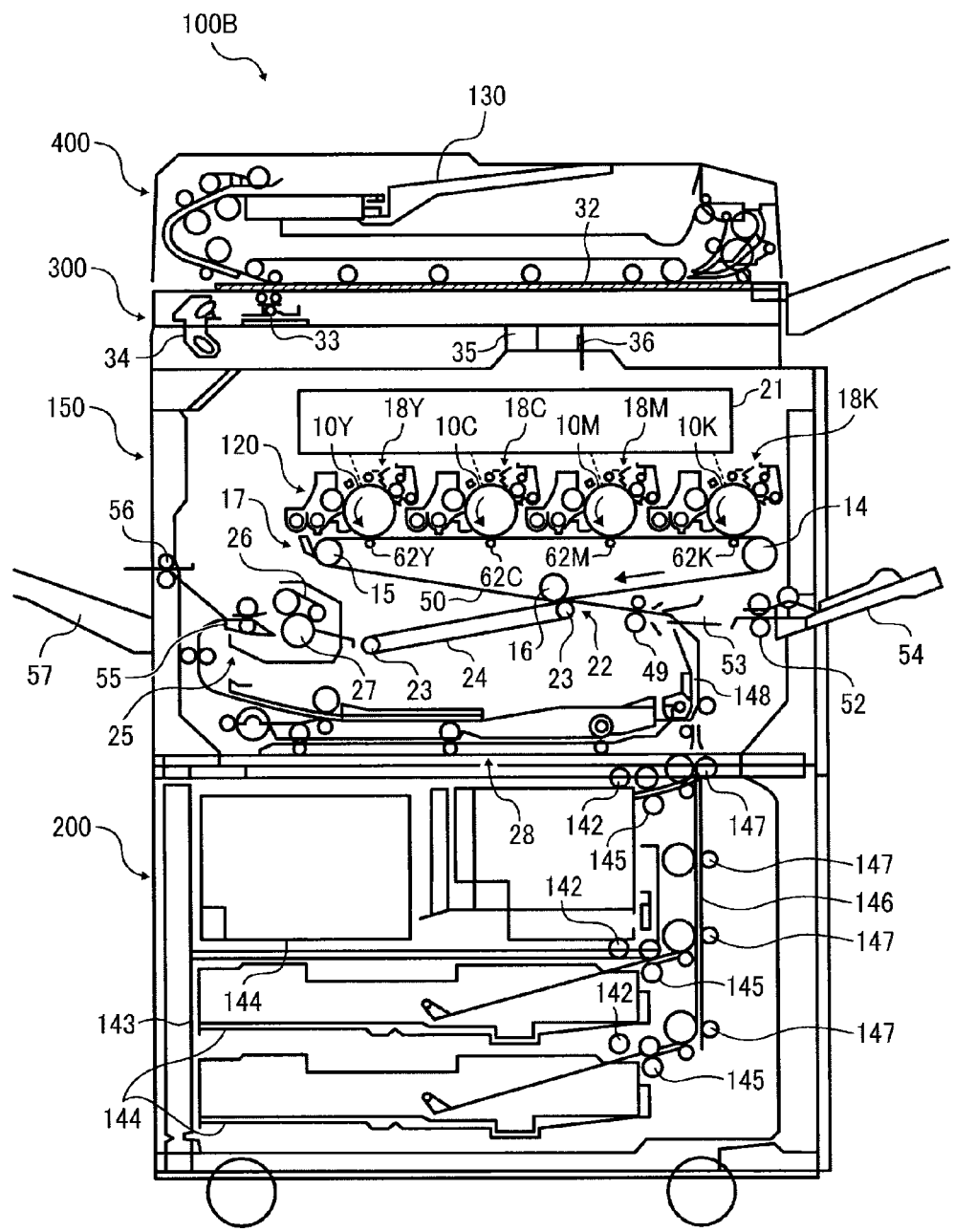
FIG. 2 is a schematic view of an image forming apparatus according to another embodiment.

FIG. 2 is a schematic view of an image forming apparatus according to another embodiment. An image forming apparatus 100B is a tandem-type full-color image forming apparatus including a main body 150, a paper feed table 200, a scanner 300, and an automatic document feeder (ADF) 400.

An intermediate transfer belt 50, disposed at a center part of the main body 150, is a seamless belt stretched taut with three rollers 14, 15, and 16 and is movable in a direction indicated by arrow in FIG. 2. A cleaner 17 is disposed adjacent to the roller 15. The cleaner 17 is adapted to remove residual toner particles remaining on the intermediate transfer belt 50 without being transferred onto a recording medium. An image forming unit 120, including photoreceptor drums 10K, 10M, 10C, and 10Y, is disposed facing the intermediate transfer belt 50 stretched between the rollers 14 and 15. An irradiator 21 is disposed adjacent to the image forming unit 120. A secondary transfer belt 24 is disposed on the opposite side of the image forming unit 120 with respect to the intermediate transfer belt 50. The secondary transfer belt 24 is a seamless belt stretched taut with a pair of rollers 23. A recording medium conveyed by the secondary transfer belt 24 is brought into contact with the intermediate transfer belt 50 in between the rollers 16 and 23. A fixing device 25 is disposed adjacent to the secondary transfer belt 24. The fixing device 25 includes a seamless fixing belt 26 stretched taut with a pair of rollers and a pressing roller 27 pressed against the fixing belt 26. A sheet reversing device 28 adapted to reverse recording medium in duplexing is disposed adjacent to the secondary transfer belt 24 and the fixing device 25. The image forming unit 120 includes image forming units 18K, 18M, 18C, and 18Y. The secondary transfer belt 24 and the rollers 23 form a secondary transfer device 22.

The image forming apparatus 100B produces a full-color image in the manner described below. A document is set on a document table 130 of the automatic document feeder 400. Alternatively, a document is set on a contact glass 32 of the scanner 300 while lifting up the automatic document feeder 400, followed by holding down of the automatic document feeder 400. Upon pressing of a switch, in a case in which a document is set on the contact glass 32, the scanner 300 immediately starts driving so that a first runner 33 and a second runner 34 start moving. In a case in which a document is set on the automatic document feeder 400, the scanner 300 starts driving after the document is fed onto the contact glass 32. The first runner 33 directs light to the document and reflects a light reflected from the document toward the second runner 34. The second runner 34 then reflects the light toward a reading sensor 36 through an imaging lens 35. Thus, image information of black, magenta, cyan, and yellow is read.

Figure 3:
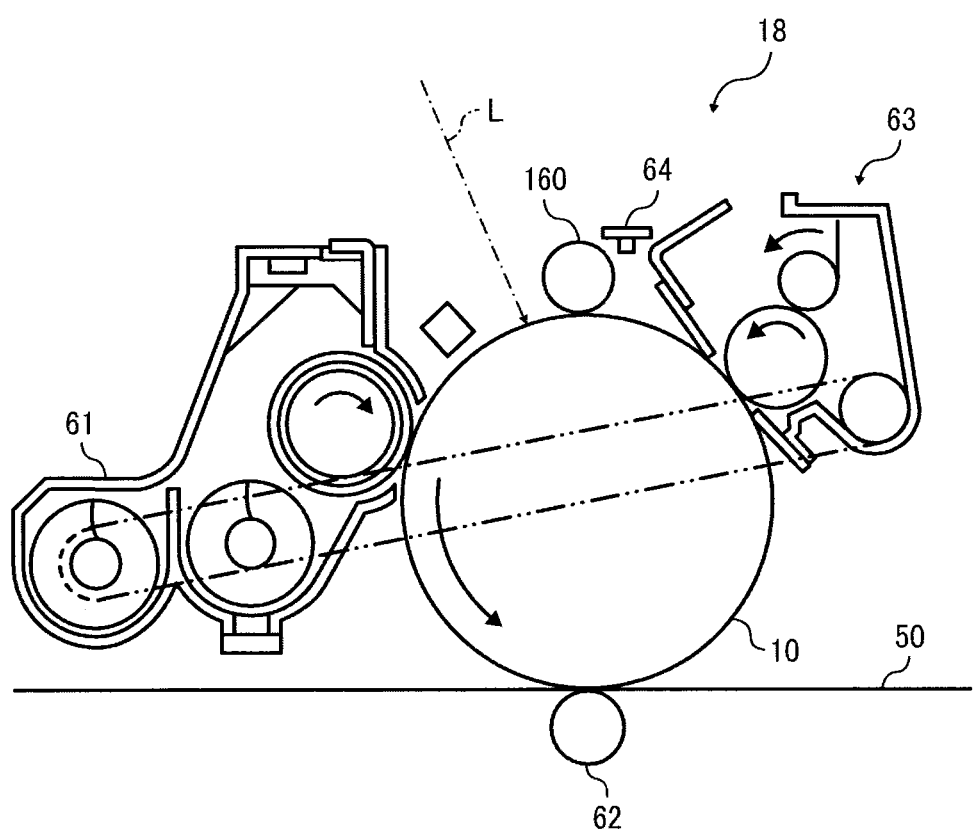
FIG. 3 is a magnified view of one of the image forming units included in the image forming apparatus illustrated in FIG. 2.

The image information is transmitted to each image forming unit 18K, 18M, 18C, or 18Y so that a toner image of black, magenta, cyan, or yellow is formed, respectively. FIG. 3 is a magnified view of one of the image forming units 18. Each of the image forming units 18 includes a photoreceptor drum 10, a charging roller 160 adapted to uniformly charge the photoreceptor drum 10, an irradiator adapted to irradiate the charged surface of the photoreceptor drum 10 with light L containing image information, a developing device 61 adapted to develop an electrostatic latent image into a toner image, a transfer roller 62 adapted to transfer the toner image onto the intermediate transfer belt 50, a cleaner 63, and a neutralization lamp 64.

The toner images formed in the image forming units 18K, 18M, 18C, and 18Y are sequentially transferred onto the intermediate transfer belt 50 while the intermediate transfer belt 50 is endlessly moving so that the toner images are superimposed on one another to form a composite toner image thereon.

On the other hand, upon pressing of the switch, one of paper feed rollers 142 starts rotating in the paper feed table 200 so that a sheet of a recording medium is fed from one of paper feed cassettes 144 in a paper bank 143. The sheet is separated by one of separation rollers 145 and fed to a paper feed path 146. Feed rollers 147 feed the sheet to a paper feed path 148 in the main body 150. The sheet is then stopped by a registration roller 49. Alternatively, a recording medium may be fed from a manual feed tray 54. In this case, a separation roller 52 separates a sheet of the recording medium and feeds it to a manual paper feed path 53. The sheet is then stopped by the registration roller 49. Although the registration roller 49 is generally grounded, the registration roller 49 can be supplied with a bias for the purpose of removing paper powders from the sheet. The registration roller 49 feeds the sheet to the gap between the intermediate transfer belt 50 and the secondary transfer belt 24 in synchronization with an entry of the composite toner image formed on the intermediate transfer belt 50 into the gap. After the composite toner image is transferred, residual toner particles remaining on the intermediate transfer belt 50 are removed by the cleaner 17.

The secondary transfer belt 24 conveys the recording medium having the composite toner image thereon to the fixing device 25. The fixing device 25 fixes the composite toner image on the recording medium. A switch claw 55 switches paper feed paths so that the sheet is discharged onto a discharge tray 57 by rotation of a discharge roller 56. Alternatively, the switch claw 55 switches paper feed paths so that the sheet gets reversed in the sheet reversing device 28. After forming another toner image on the back side of the sheet, the sheet is discharged onto the discharge tray 57 by rotation of the discharge roller 56.

EXAMPLES

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

Preparation of Amorphous Polyester Resin (a-1)

In an autoclave reaction vessel equipped with a thermometer, a stirrer, and a nitrogen inlet pipe, 70 parts of L-lactide, 30 parts of D-lactide, and 5 parts of ε-caprolactone are heated and melted at 120° C. for 20 minutes under nitrogen atmosphere. Thereafter, 0.03 parts of tin 2-ethylhexanoate are further added to the vessel to cause a ring-opening polymerization at 190° C. for 3 hours.

After termination of the reaction, residual lactide and ε-caprolactone are removed under reduced pressures. Thus, an amorphous polyester resin (a-1) having a polyhydroxycarboxylic acid skeleton is prepared.

The amorphous polyester resin (a-1) has a number average molecular weight (Mn) of 9,200, a weight average molecular weight (Mw) of 3,700, and an optical purity (X) of 40% by mole.

Preparation of Amorphous Polyester Resin (a-2) (Polyester Diol)

In an autoclave reaction vessel equipped with a thermometer, a stirrer, and a nitrogen inlet pipe, 0.8 parts of 1,3-propanediol, 76 parts of L-lactide, and 24 parts of D-lactide are heated and melted at 120° C. for 20 minutes under nitrogen atmosphere. Thereafter, 0.03 parts of tin 2-ethylhexanoate are further added to the vessel to cause a ring-opening polymerization at 190° C. for 3 hours.

After termination of the reaction, residual lactide is removed under reduced pressures. Thus, an amorphous polyester resin (a-2) (polyester diol) having a polyhydroxycarboxylic acid skeleton is prepared.

The amorphous polyester resin (a-2) has a number average molecular weight (Mn) of 2,400, a weight average molecular weight (Mw) of 9,000, and an optical purity (X) of 52% by mole.

Preparation of Amorphous Polyester Resin (a-3) (Polyester Diol)

In an autoclave reaction vessel equipped with a thermometer, a stirrer, and a nitrogen inlet pipe, 0.9 parts of 1,4-butanediol, 76 parts of L-lactide, and 24 parts of D-lactide are heated and melted at 120° C. for 20 minutes under nitrogen atmosphere. Thereafter, 0.03 parts of tin 2-ethylhexanoate are further added to the vessel to cause a ring-opening polymerization at 180° C. for 3 hours.

After termination of the reaction, residual lactide is removed under reduced pressures. Thus, an amorphous polyester resin (a-3) (polyester diol) having a polyhydroxycarboxylic acid skeleton is prepared.

The amorphous polyester resin (a-3) has a number average molecular weight (Mn) of 3,200, a weight average molecular weight (Mw) of 11,000, and an optical purity (X) of 52% by mole.

Preparation of Amorphous Polyester Resin (a-4) (Polyester Diol)

In an autoclave reaction vessel equipped with a thermometer, a stiffer, and a nitrogen inlet pipe, 0.7 parts of 1,3-propanediol, 50 parts of L-lactide, and 46 parts of mesolactide are heated and melted at 120° C. for 20 minutes under nitrogen atmosphere. Thereafter, 0.03 parts of tin 2-ethylhexanoate are further added to the vessel to cause a ring-opening polymerization at 180° C. for 3 hours.

After termination of the reaction, residual lactide is removed under reduced pressures. Thus, an amorphous polyester resin (a-4) (polyester diol) having a polyhydroxycarboxylic acid skeleton is prepared.

The amorphous polyester resin (a-4) has a number average molecular weight (Mn) of 4,600, a weight average molecular weight (Mw) of 15,000, and an optical purity (X) of 52% by mole.

Preparation of Amorphous Polyester Resin (a-5) (Polyester Diol)

In an autoclave reaction vessel equipped with a thermometer, a stirrer, and a nitrogen inlet pipe, 0.55 parts of 1,3-propanediol, 50 parts of L-lactide, and 46 parts of mesolactide are heated and melted at 120° C. for 20 minutes under nitrogen atmosphere. Thereafter, 0.03 parts of tin 2-ethylhexanoate are further added to the vessel to cause a ring-opening polymerization at 180° C. for 3 hours.

After termination of the reaction, residual lactide is removed under reduced pressures. Thus, an amorphous polyester resin (a-4) (polyester diol) having a polyhydroxycarboxylic acid skeleton is prepared.

The amorphous polyester resin (a-4) has a number average molecular weight (Mn) of 8,200, a weight average molecular weight (Mw) of 34,000, and an optical purity (X) of 52% by mole.

Preparation of Amorphous Polyester Resin (a-6) (Polyester Diol)

In an autoclave reaction vessel equipped with a thermometer, a stirrer, and a nitrogen inlet pipe, 0.6 parts of 1,4-butanediol, 76 parts of L-lactide, and 24 parts of D-lactide are heated and melted at 120° C. for 20 minutes under nitrogen atmosphere. Thereafter, 0.03 parts of tin 2-ethylhexanoate are further added to the vessel to cause a ring-opening polymerization at 180° C. for 3 hours.

After termination of the reaction, residual lactide is removed under reduced pressures. Thus, an amorphous polyester resin (a-6) (polyester diol) having a polyhydroxycarboxylic acid skeleton is prepared.

The amorphous polyester resin (a-6) has a number average molecular weight (Mn) of 12,000, a weight average molecular weight (Mw) of 41,000, and an optical purity (X) of 52% by mole.

Preparation of Amorphous Polyester Resin (a-7) (Polyester Diol)

In an autoclave reaction vessel equipped with a thermometer, a stirrer, and a nitrogen inlet pipe, 0.65 parts of 1,3-propanediol, 80 parts of L-lactide, and 20 parts of D-lactide are heated and melted at 120° C. for 20 minutes under nitrogen atmosphere. Thereafter, 0.03 parts of tin 2-ethylhexanoate are further added to the vessel to cause a ring-opening polymerization at 180° C. for 3 hours.

After termination of the reaction, residual lactide is removed under reduced pressures. Thus, an amorphous polyester resin (a-7) (polyester diol) having a polyhydroxycarboxylic acid skeleton is prepared.

The amorphous polyester resin (a-7) has a number average molecular weight (Mn) of 7,600, a weight average molecular weight (Mw) of 26,000, and an optical purity (X) of 60% by mole.

Preparation of Amorphous Polyester Resin (a-8)

In an autoclave reaction vessel equipped with a thermometer, a stirrer, and a nitrogen inlet pipe, 85 parts of L-lactide and 25 parts of mesolactide are heated and melted at 120° C. for 20 minutes under nitrogen atmosphere. Thereafter, 0.03 parts of tin 2-ethylhexanoate are further added to the vessel to cause a ring-opening polymerization at 180° C. for 3 hours.

After termination of the reaction, residual lactide is removed under reduced pressures. Thus, an amorphous polyester resin (a-8) having a polyhydroxycarboxylic acid skeleton is prepared.

The amorphous polyester resin (a-8) has a number average molecular weight (Mn) of 8,800, a weight average molecular weight (Mw) of 39,000, and an optical purity (X) of 77% by mole.

Preparation of Amorphous Polyester Resin (a-9) (Polyester Diol)

In an autoclave reaction vessel equipped with a thermometer, a stirrer, and a nitrogen inlet pipe, 1 part of 1,4-butanediol, 50 parts of L-lactide, and 13 parts of D-lactide are heated and melted at 120° C. for 20 minutes under nitrogen atmosphere. Thereafter, 0.03 parts of tin 2-ethylhexanoate are further added to the vessel to cause a ring-opening polymerization at 180° C. for 3 hours.

After termination of the reaction, residual lactide is removed under reduced pressures. Thus, a polyester diol (a11-1) having a polyhydroxycarboxylic acid skeleton is prepared.

In another autoclave reaction vessel equipped with a thermometer, a stirrer, and a nitrogen inlet pipe, a toluene solution of 17.5 parts of EO 2 mol adduct of bisphenol A, 17.5 parts of terephthalic acid, and 0.02 parts of tin 2-ethylhexanoate is subjected to a reaction at 200° C. and 8 kPa for 15 hours. After termination of the reaction, the temperature and pressure are returned to normal temperature and pressure. Thus, a polyester diol (a12-1) is prepared.

The polyester diol (a11-1) in an amount of 70 parts and the polyester diol (a12-1) in an amount of 30 parts are dissolved in methyl ethyl ketone. Isophorone diisocyanate (IPDI), as an elongating agent, in an amount of 8 parts is added thereto to cause a reaction at 50° C. for 6 hours. After termination of the reaction, the solvent is removed. Thus, an amorphous polyester resin (a-9) is prepared.

The amorphous polyester resin (a-9) has a number average molecular weight (Mn) of 5,300, a weight average molecular weight (Mw) of 21,000, and an optical purity (X) of 59% by mole.

Preparation of Amorphous Polyester Resin (a-10)

In an autoclave reaction vessel equipped with a thermometer, a stirrer, and a nitrogen inlet pipe, 92 parts of L-lactide, 8 parts of D-lactide, and 10 parts of ε-caprolactone are heated and melted at 120° C. for 20 minutes under nitrogen atmosphere. Thereafter, 0.03 parts of tin 2-ethylhexanoate are further added to the vessel to cause a ring-opening polymerization at 190° C. for 3 hours.

After termination of the reaction, residual lactide and ε-caprolactone are removed under reduced pressures. Thus, an amorphous polyester resin (a-10) having a polyhydroxycarboxylic acid skeleton is prepared.

The amorphous polyester resin (a-10) has a number average molecular weight (Mn) of 8,200, a weight average molecular weight (Mw) of 31,000, and an optical purity (X) of 84% by mole.

Preparation of Amorphous Polyester Resin (d) Having no Polyhydroxycarboxylic Acid Skeleton In an autoclave reaction vessel equipped with a thermometer, a stirrer, and a nitrogen inlet pipe, a toluene solution of 10 parts of EO 2 mol adduct of bisphenol A, 8 parts of terephthalic acid, 2 parts of adipic acid, and 0.01 parts of tin 2-ethylhexanoate is subjected to a reaction at 200° C. and 8 kPa for 15 hours. Thus, an amorphous polyester resin (d) having no polyhydroxycarboxylic acid skeleton is prepared.

The amorphous polyester resin (d) has a number average molecular weight (Mn) of 2,900 and a weight average molecular weight (Mw) of 6,800.

Compositions and properties of the above-prepared resins, i.e., the first resins are summarized in Table 1.

TABLE 1

| | First Binder Resins | | | | | | | | | | |
|---|---|---|---|---|---|---|---|---|---|---|---|
| | (a-1) | (a-2) | (a-3) | (a-4) | (a-5) | (a-6) | (a-7) | (a-8) | (a-9) | (a-10) | (d) |
| 1,3-Propanediol | 0 | 0.8 | 0 | 0.7 | 0.55 | 0 | 0.65 | 0 | 0 | 0 | 0 |
| 1,4-Butanediol | 0 | 0 | 0.9 | 0 | 0 | 0.6 | 0 | 0 | 1 | 0 | 0 |
| L-Lactide | 70 | 76 | 76 | 50 | 50 | 76 | 80 | 85 | 50 | 92 | 0 |
| D-Lactide | 30 | 24 | 24 | 0 | 0 | 24 | 20 | 0 | 13 | 8 | 0 |
| LD-Mesolactide | 0 | 0 | 0 | 46 | 46 | 0 | 0 | 25 | 0 | 0 | 0 |
| ε-Caprolactone | 5 | 0 | 0 | 0 | 0 | 0 | 0 | 0 | 0 | 10 | 0 |
| Tin 2-Ethylhexanoate | 0.03 | 0.03 | 0.03 | 0.03 | 0.03 | 0.03 | 0.03 | 0.03 | 0.03 | 0.03 | 0 |
| EO 2 mol Adduct of Bisphenol A | 0 | 0 | 0 | 0 | 0 | 0 | 0 | 0 | 17.5 | 0 | 10 |
| Terephthalic Acid | 0 | 0 | 0 | 0 | 0 | 0 | 0 | 0 | 17.5 | 0 | 8 |
| Adipic Acid | 0 | 0 | 0 | 0 | 0 | 0 | 0 | 0 | 0 | 0 | 2 |
| Tin 2-Ethylhexanoate | 0 | 0 | 0 | 0 | 0 | 0 | 0 | 0 | 0.02 | 0 | 0.01 |
| Optical Purity (X) | 40% | 52% | 52% | 52% | 52% | 52% | 60% | 77% | 59% | 84% | — |
| Weight Average Molecular Weight (Mw) | 37,000 | 9,000 | 11,000 | 15,000 | 34,000 | 41,000 | 26,000 | 39,000 | 21,000 | 31,000 | 6,800 |
| Number Average Molecular Weight (Mn) | 9,200 | 2,400 | 3,200 | 4,600 | 8,200 | 12,000 | 7,600 | 8,800 | 5,300 | 8,200 | 2,900 |

Preparation of Water Dispersion of Polyester Resin (b-1) Particles

In an autoclave reaction vessel, a mixture of 79 parts of terephthalic acid, 7 parts of isophthalic acid, 14 parts of ethylene glycol, and 29 parts of neopentyl glycol is heated at 260° C. for 4 hours to cause an esterification reaction. After adding 0.06 parts of tetrabutyl titanate as a catalyst, the reaction system temperature is increased to 280° C. and the reaction system pressure is gradually reduced to 13 Pa over a period of 1.5 hours. The polycondensation reaction is further continued for 2 hours. Thereafter, the reaction system pressure is returned to normal pressure by introducing nitrogen gas and the reaction system temperature is reduced to 270° C. Trimellitic acid in an amount of 2 parts is further added to the vessel at 270° C. and is agitated at 250° C. for 1 hour to cause a depolymerization reaction. Thereafter, the reaction system is put in a pressurized condition with nitrogen gas. Thus, a sheet-like resin is obtained. After being cooled to room temperature, the sheet-like resin is pulverized into particles and the particles are sieved. The particles collected with a sieve having an opening of 1 to 6 mm are collected. Thus, a granular polyester resin (b-1) is prepared.

In a 1-liter glass vessel equipped with a jacket, 100 parts of the granular polyester resin (b-1), 60 parts of isopropyl alcohol, 1.6 parts of 28% ammonia water, and 170 parts of distilled water are agitated by a stirrer (T.K. ROBOMIX from Primix Corporation) at a revolution of 7,000 rpm. The jacket is heated by flowing hot water therein to increase the reaction system temperature to 73 to 75° C. and the agitation is further continued for 60 minutes. Thereafter, the jacket is cooled to room temperature by flowing cold water therein while the agitation revolution is reduced to 5,000 rpm. Thus, a milky aqueous dispersion of the polyester resin (b-1) is prepared.

A 1-liter two-necked round-bottom flask is charged with 300 parts of the aqueous dispersion of the polyester resin (b-1) and 80 parts of distilled water and a mechanical stirrer and a Liebig condenser are put into place. The flask is heated in an oil bath to remove the aqueous medium. The heating of the flask is terminated at the time about 160 parts of the aqueous medium have been removed. The flask is cooled under room temperature. Liquid components remaining in the flask are filtered with a 600 mesh (twilled dutch weave). The solid content in the filtrate is 40% by weight. The filtrate is supplied with distilled water while being agitated so that the solid content becomes 30% by weight. Thus, a water dispersion of the polyester resin (b-1) particles is prepared.

The polyester resin (b-1) particles has a volume average particle diameter of 68 nm, a weight average molecular weight (Mw) of 9,800, a glass transition temperature (Tg) of 68° C., and an acid value of 30 mgKOH/g.

Preparation of Water Dispersion of Polyester Resin (b-2) Particles

In an autoclave reaction vessel, a mixture of 56 parts of terephthalic acid, 27 parts of isophthalic acid, 12 parts of ethylene glycol, and 31 parts of neopentyl glycol is heated at 260° C. for 4 hours to cause an esterification reaction. After adding 0.05 parts of tetrabutyl titanate as a catalyst, the reaction system temperature is increased to 280° C. and the reaction system pressure is gradually reduced to 130 Pa over a period of 1.5 hours. The polycondensation reaction is further continued for 2 hours. Thereafter, the reaction system pressure is returned to normal pressure by introducing nitrogen gas and the reaction system temperature is reduced to 270° C. Trimellitic acid in an amount of 22 parts is further added to the vessel at 270° C. and is agitated at 250° C. for 1 hour to cause a depolymerization reaction. Thereafter, the reaction system is put in a pressurized condition with nitrogen gas. Thus, a sheet-like resin is obtained. After being cooled to room temperature, the sheet-like resin is pulverized into particles and the particles are sieved. The particles collected with a sieve having an opening of 1 to 6 mm are collected. Thus, a granular polyester resin (b-2) is prepared.

In a 1-liter glass vessel equipped with a jacket, 100 parts of the granular polyester resin (b-2), 60 parts of isopropyl alcohol, 1.6 parts of 28% ammonia water, and 170 parts of distilled water are agitated by a stirrer (T.K. ROBOMIX from Primix Corporation) at a revolution of 7,000 rpm. The jacket is heated by flowing hot water therein to increase the reaction system temperature to 73 to 75° C. and the agitation is further continued for 60 minutes. Thereafter, the jacket is cooled to room temperature by flowing cold water therein while the agitation revolution is reduced to 5,000 rpm. Thus, a milky aqueous dispersion of the polyester resin (b-2) is prepared.

A 1-liter two-necked round-bottom flask is charged with 300 parts of the aqueous dispersion of the polyester resin (b-2) and 80 parts of distilled water and a mechanical stirrer and a Liebig condenser are put into place. The flask is heated in an oil bath to remove the aqueous medium. The heating of the flask is terminated at the time about 160 parts of the aqueous medium have been removed. The flask is cooled under room temperature. Liquid components remaining in the flask are filtered with a 600 mesh (twilled dutch weave). The solid content in the filtrate is 40% by weight. The filtrate is supplied with distilled water while being agitated so that the solid content becomes 30% by weight. Thus, a water dispersion of the polyester resin (b-2) particles is prepared.

The polyester resin (b-2) particles has a volume average particle diameter of 107 nm, a weight average molecular weight (Mw) of 13,500, a glass transition temperature (Tg) of 63° C., and an acid value of 22 mgKOH/g.

Preparation of Water Dispersion of Styrene-Acrylic Resin (b-3) Particles

A reaction vessel equipped with a stirrer and a thermometer is charged with 600 parts of water, 120 parts of styrene, 100 parts of methacrylic acid, 45 parts of butyl acrylate, 10 parts of a sodium alkylallylsulfosuccinate (ELEMINOL JS-2 from Sanyo Chemical Industries, Ltd.), and 1 part of ammonium persulfate. The mixture is agitated for 20 minutes at a revolution of 400 rpm. Thus, a white emulsion is prepared. The emulsion is heated to 75° C. and subjected to a reaction for 6 hours. After adding 30 parts of a 1% aqueous solution of ammonium persulfate to the emulsion, the emulsion is aged for 6 hours at 75° C. Thus, a water dispersion of styrene-acrylic resin particles (b-3) is prepared.

The styrene-acrylic resin (b-3) particles have a volume average particle diameter of 80 nm, a weight average molecular weight (Mw) of 160,000, and a glass transition temperature (Tg) of 74° C.

Compositions and properties of the above-prepared resins, i.e., the second resins are summarized in Table 2.

TABLE 2

| | Second Binder Resins | | |
| --- | --- | --- | --- |
| | (b-1) | (b-2) | (b-3) |
| Terephthalic Acid | 79 | 56 | 0 |
| Isophthalic Acid | 7 | 27 | 0 |
| Trimellitic Acid | 2 | 22 | 0 |
| Ethylene Glycol | 14 | 12 | 0 |
| Neopentyl Glycol | 29 | 31 | 0 |
| Tetrabutyl Titanate | 0.06 | 0.05 | 0 |
| Styrene | 0 | 0 | 120 |
| Methacrylic Acid | 0 | 0 | 100 |
| Butyl Acrylate | 0 | 0 | 45 |
| Sodium Alkylallyl-sulfosuccinate | 0 | 0 | 10 |
| Ammonium Persulfate | 0 | 0 | 1 |
| Weight Average Molecular Weight (Mw) | 9,800 | 13,500 | 160,000 |
| Tg (° C.) | 68 | 63 | 74 |
| Volume Average Particle Diameter (nm) | 68 | 107 | 80 |

Preparation of Release Agent Dispersing Resin (c-1) (Graft Polymer)

In a reaction vessel equipped with a stirrer and a thermometer, 100 parts of a low-molecular-weight polyethylene (SANWAX LEL-400 from Sanyo Chemical Industries, Ltd., having a softening point of 128° C.) are dissolved in 480 parts of xylene. After replacing the air in the vessel with nitrogen gas, a mixed solution of 740 parts of styrene, 100 parts of acrylonitrile, 60 parts of butyl acrylate, 36 parts of di-t-butylperoxyhexahydroterephthalate, and 100 parts of xylene is dropped therein at 170° C. over a period of 3 hours to cause a polymerization. The reaction system is kept at 170° C. for 30 minutes. Thereafter, the solvents are removed. Thus, a graft polymer (c-1) is prepared.

The graft polymer (c-1) has a number average molecular weight (Mn) of 4,500 and a weight average molecular weight (Mw) of 24,000, a glass transition temperature (Tg) of 67° C. The vinyl resin portion has a solubility parameter of 10.9 $(cal/cm^3)^{1/2}$.

Preparation of Release Agent Dispersing Resin (c-2) (Graft Polymer)

In a reaction vessel equipped with a stirrer and a thermometer, 150 parts of a low-molecular-weight polyethylene (SANWAX LEL-400 from Sanyo Chemical Industries, Ltd., having a softening point of 128° C.) are dissolved in 480 parts of xylene. After replacing the air in the vessel with nitrogen gas, a mixed solution of 700 parts of styrene, 95 parts of acrylonitrile, 55 parts of butyl acrylate, 36 parts of di-t-butylperoxyhexahydroterephthalate, and 100 parts of xylene is dropped therein at 170° C. over a period of 3 hours to cause a polymerization. The reaction system is kept at 170° C. for 30 minutes. Thereafter, the solvents are removed. Thus, a graft polymer (c-2) is prepared.

The graft polymer (c-2) has a number average molecular weight (Mn) of 3,400 and a weight average molecular weight (Mw) of 16,000, a glass transition temperature (Tg) of 63° C. The vinyl resin portion has a solubility parameter of 10.7 $(cal/cm^3)^{1/2}$.

Preparation of Release Agent Dispersing Resin (c-3) (Graft Polymer)

In a reaction vessel equipped with a stirrer and a thermometer, 200 parts of a low-molecular-weight polypropylene (VISCOL 660P from Sanyo Chemical Industries, Ltd., having a softening point of 145° C.) are dissolved in 480 parts of xylene. After replacing the air in the vessel with nitrogen gas, a mixed solution of 636 parts of styrene, 70 parts of acrylonitrile, 88 parts of butyl acrylate, 6 parts of acrylic acid, 30 parts of di-t-butylperoxyhexahydroterephthalate, and 250 parts of xylene is dropped therein at 170° C. over a period of 3 hours to cause a polymerization. The reaction system is kept at 170° C. for 30 minutes. Thereafter, the solvents are removed. Thus, a graft polymer (c-3) is prepared.

The graft polymer (c-3) has a number average molecular weight (Mn) of 2,800 and a weight average molecular weight (Mw) of 11,000, a glass transition temperature (Tg) of 58° C. The vinyl resin portion has a solubility parameter of 10.8 $(cal/cm^3)^{1/2}$.

Preparation of Release Agent Dispersing Resin (c-4) (Polyester Resin)

In a four-necked flask equipped with a thermometer, a nitrogen inlet pipe, a stirrer, and a condenser, 10 parts of pentaerythritol and 90 parts of stearic acid are subjected to a reaction for 15 hours at 220° C. at normal pressure under nitrogen gas flow while removing the reaction water. The resulting esterification crude product in an amount of 95 parts, ethylene glycol in an amount of 15 parts, and 10% potassium hydroxide water solution in an amount containing potassium hydroxide in an amount 1.5 times the equivalent amount of the acid value of the esterification crude product are mixed and agitated for 30 minutes at 70° C. The mixture is allowed to stand for 30 minutes and then the water layer is removed. Thus, the deoxidation process is terminated. The esterification crude product in an amount of 100 parts and ion-exchange water in an amount of 20 parts are mixed and agitated for 30 minutes at 70° C. The mixture is allowed to stand for 30 minutes and then the water layer is separated and removed. The remaining ester layer is repeatedly washed with water for 4 times until the waste water has expressed a neutral pH. The solvents are removed from the ester layer at 180° C. under a reduced pressure of 1 kPa and the ester layer is then filtered. Thus, an ester compound 1 having a melting point of 79° C., an acid value of 0.2 mgKOH/g, and a hydroxyl value of 1.6 mgKOH/g is prepared.

A reaction vessel equipped with a distillation column is charged with 29 parts of terephthalic acid, 0.4 parts of isophthalic acid, 7 parts of trimellitic anhydride, 8 parts of ethylene glycol, 47 parts of polyoxypropylene(2.3)-2,2-bis(4-hydroxyphenyl)propane, 7 parts of polyoxyethylene(2)-2,2-bis(4-hydroxyphenyl)propane, 2 parts of the ester compound 1, and 800 ppm of antimony trioxide as a catalyst. These materials are subjected to an esterification reaction for 7 hours by being agitated with agitation blades at a revolution of 120 rpm at a reaction system temperature of 265° C. The reaction system temperature is then kept at 235° C. and the reaction system pressure is reduced to 7.5 mmHg (1 kPa) over a period of about 40 minutes to cause a condensation reaction while removing diol components from the reaction system. As the reaction system viscosity increased, the degree of vacuum also increased. The condensation reaction is continued until the agitation blades have expressed a torque corresponding to a desired softening point. Upon reaching a predetermined torque, the reaction system pressure is returned to normal pressure and the heating is terminated. The reaction system is pressurized with nitrogen gas and a reaction product is taken out over a period of about 40 minutes. Thus, a polyester resin (c-4) is prepared.

The polyester resin (c-4) has a number average molecular weight (Mn) of 4,600 and a weight average molecular weight (Mw) of 28,000, and a glass transition temperature (Tg) of 55° C.

Preparation of Release Agent Dispersing Resin (c-5) (Polyester Resin)

A reaction vessel equipped with a distillation column is charged with 30 parts of terephthalic acid, 0.4 parts of isophthalic acid, 8 parts of trimellitic anhydride, 10 parts of ethylene glycol, 48 parts of polyoxypropylene(2.3)-2,2-bis(4-hydroxyphenyl)propane, 4 parts of the ester compound 1, and 800 ppm of antimony trioxide as a catalyst. These materials are subjected to an esterification reaction for 7 hours by being agitated with agitation blades at a revolution of 120 rpm at a reaction system temperature of 265° C. The reaction system temperature is then kept at 235° C. and the reaction system pressure is reduced to 7.5 mmHg (1 kPa) over a period of about 40 minutes to cause a condensation reaction while removing diol components from the reaction system. As the reaction system viscosity increased, the degree of vacuum also increased. The condensation reaction is continued until the agitation blades have expressed a torque corresponding to a desired softening point. Upon reaching a predetermined torque, the reaction system pressure is returned to normal pressure and the heating is terminated. The reaction system is pressurized with nitrogen gas and a reaction product is taken out over a period of about 40 minutes. Thus, a polyester resin (c-5) is prepared.

The polyester resin (c-5) has a number average molecular weight (Mn) of 4,900 and a weight average molecular weight (Mw) of 34,000, and a glass transition temperature (Tg) of 52° C.

Preparation of Release Agent Dispersing Resin (c-6) (Polyester Resin)

In a four-necked flask equipped with a thermometer, a nitrogen inlet pipe, a stirrer, and a condenser, 9 parts of pentaerythritol and 91 parts of behenic acid are subjected to a reaction for 15 hours at 220° C. at normal pressure under nitrogen gas flow while removing the reaction water. The resulting esterification crude product in an amount of 95 parts, ethylene glycol in an amount of 15 parts, and 10% potassium hydroxide water solution in an amount containing potassium hydroxide in an amount 1.5 times the equivalent amount of the acid value of the esterification crude product are mixed and agitated for 30 minutes at 70° C. The mixture is allowed to stand for 30 minutes and then the water layer is removed. Thus, the deoxidation process is terminated. The esterification crude product in an amount of 100 parts and ion-exchange water in an amount of 20 parts are mixed and agitated for 30 minutes at 70° C. The mixture is allowed to stand for 30 minutes and then the water layer is separated and removed. The remaining ester layer is repeatedly washed with water for 4 times until the waste water has expressed a neutral pH. The solvents are removed from the ester layer at 180° C. under a reduced pressure of 1 kPa and the ester layer is then filtered. Thus, an ester compound 2 having a melting point of 85° C., an acid value of 0.2 mgKOH/g, and a hydroxyl value of 1.6 mgKOH/g is prepared.

A reaction vessel equipped with a distillation column is charged with 29 parts of terephthalic acid, 0.4 parts of isophthalic acid, 7 parts of trimellitic anhydride, 8 parts of ethylene glycol, 47 parts of polyoxypropylene(2.3)-2,2-bis(4-hydroxyphenyl)propane, 7 parts of polyoxyethylene(2)-2,2-bis(4-hydroxyphenyl)propane, 2 parts of the ester compound 2, and 800 ppm of antimony trioxide as a catalyst. These materials are subjected to an esterification reaction for 7 hours by being agitated with agitation blades at a revolution of 120 rpm at a reaction system temperature of 265° C. The reaction system temperature is then kept at 235° C. and the reaction system pressure is reduced to 7.5 mmHg (1 kPa) over a period of about 40 minutes to cause a condensation reaction while removing diol components from the reaction system. As the reaction system viscosity increased, the degree of vacuum also increased. The condensation reaction is continued until the agitation blades have expressed a torque corresponding to a desired softening point. Upon reaching a predetermined torque, the reaction system pressure is returned to normal pressure and the heating is terminated. The reaction system is pressurized with nitrogen gas and a reaction product is taken out over a period of about 40 minutes. Thus, a polyester resin (c-6) is prepared.

The polyester resin (c-6) has a number average molecular weight (Mn) of 6,500 and a weight average molecular weight (Mw) of 43,000, and a glass transition temperature (Tg) of 60° C.

Preparation of Release Agent Dispersing Resin (c-7) (Polyester Resin)

In a four-necked flask equipped with a thermometer, a nitrogen inlet pipe, a stirrer, and a condenser, 11 parts of pentaerythritol and 89 parts of palmitic acid are subjected to a reaction for 15 hours at 220° C. at normal pressure under nitrogen gas flow while removing the reaction water. The resulting esterification crude product in an amount of 95 parts, ethylene glycol in an amount of 15 parts, and 10% potassium hydroxide water solution in an amount containing potassium hydroxide in an amount 1.5 times the equivalent amount of the acid value of the esterification crude product are mixed and agitated for 30 minutes at 70° C. The mixture is allowed to stand for 30 minutes and then the water layer is separated and removed. Thus, the deoxidation process is terminated. The esterification crude product in an amount of 100 parts and ion-exchange water in an amount of 20 parts are mixed and agitated for 30 minutes at 70° C. The mixture is allowed to stand for 30 minutes and then the water layer is separated and removed. The remaining ester layer is repeatedly washed with water for 4 times until the waste water has expressed a neutral pH. The solvents are removed from the ester layer at 180° C. under a reduced pressure of 1 kPa and the ester layer is then filtered. Thus, an ester compound 3 having a melting point of 72° C., an acid value of 0.2 mgKOH/g, and a hydroxyl value of 0.8 mgKOH/g is prepared.

A reaction vessel equipped with a distillation column is charged with 29 parts of terephthalic acid, 0.4 parts of isophthalic acid, 7 parts of trimellitic anhydride, 8 parts of ethylene glycol, 47 parts of polyoxypropylene(2.3)-2,2-bis(4-hydroxyphenyl)propane, 7 parts of polyoxyethylene(2)-2,2-bis(4-hydroxyphenyl)propane, 2 parts of the ester compound 3, and 800 ppm of antimony trioxide as a catalyst. These materials are subjected to an esterification reaction for 7 hours by being agitated with agitation blades at a revolution of 120 rpm at a reaction system temperature of 265° C. The reaction system temperature is then kept at 235° C. and the reaction system pressure is reduced to 7.5 mmHg (1 kPa) over a period of about 40 minutes to cause a condensation reaction while removing diol components from the reaction system. As the reaction system viscosity increased, the degree of vacuum also increased. The condensation reaction is continued until the agitation blades have expressed a torque corresponding to a desired softening point. Upon reaching a predetermined torque, the reaction system pressure is returned to normal pressure and the heating is terminated. The reaction system is pressurized with nitrogen gas and a reaction product is taken out over a period of about 40 minutes. Thus, a polyester resin (c-7) is prepared.

The polyester resin (c-7) has a number average molecular weight (Mn) of 5,700 and a weight average molecular weight (Mw) of 38,000, and a glass transition temperature (Tg) of 48° C.

Preparation of Release Agent Dispersing Resin (c-8) (Polyester Resin)

In a four-necked flask equipped with a thermometer, a nitrogen inlet pipe, a stirrer, and a condenser, 10 parts of glycerin and 90 parts of stearic acid are subjected to a reaction for 15 hours at 220° C. at normal pressure under nitrogen gas flow while removing the reaction water. The resulting esterification crude product in an amount of 95 parts, ethylene glycol in an amount of 15 parts, and 10% potassium hydroxide water solution in an amount containing potassium hydroxide in an amount 1.5 times the equivalent amount of the acid value of the esterification crude product are mixed and agitated for 30 minutes at 70° C. The mixture is allowed to stand for 30 minutes and then the water layer is separated and removed. Thus, the deoxidation process is terminated. The esterification crude product in an amount of 100 parts and ion-exchange water in an amount of 20 parts are mixed and agitated for 30 minutes at 70° C. The mixture is allowed to stand for 30 minutes and then the water layer is separated and removed. The remaining ester layer is repeatedly washed with water for 4 times until the waste water has expressed a neutral pH. The solvents are removed from the ester layer at 180° C. under a reduced pressure of 1 kPa and the ester layer is then filtered. Thus, an ester compound 4 having a melting point of 62° C., an acid value of 0.3 mgKOH/g, and a hydroxyl value of 1.5 mgKOH/g is prepared.

A reaction vessel equipped with a distillation column is charged with 29 parts of terephthalic acid, 0.4 parts of isophthalic acid, 7 parts of trimellitic anhydride, 8 parts of ethylene glycol, 47 parts of polyoxypropylene(2.3)-2,2-bis(4-hydroxyphenyl)propane, 7 parts of polyoxyethylene(2)-2,2-bis(4-hydroxyphenyl)propane, 2 parts of the ester compound 4, and 800 ppm of antimony trioxide as a catalyst. These materials are subjected to an esterification reaction for 7 hours by being agitated with agitation blades at a revolution of 120 rpm at a reaction system temperature of 265° C. The reaction system temperature is then kept at 235° C. and the reaction system pressure is reduced to 7.5 mmHg (1 kPa) over a period of about 40 minutes to cause a condensation reaction while removing diol components from the reaction system. As the reaction system viscosity increased, the degree of vacuum also increased. The condensation reaction is continued until the agitation blades have expressed a torque corresponding to a desired softening point. Upon reaching a predetermined torque, the reaction system pressure is returned to normal pressure and the heating is terminated. The reaction system is pressurized with nitrogen gas and a reaction product is taken out over a period of about 40 minutes. Thus, a polyester resin (c-8) is prepared.

TABLE 4

|  | Ester Compound 1 | Ester Compound 2 | Ester Compound 3 | Ester Compound 4 |
|---|---|---|---|---|
| Palmitic Acid | 0 | 0 | 89 | 0 |
| Stearic Acid | 90 | 0 | 0 | 90 |
| Behenic Acid | 0 | 91 | 0 | 0 |
| Glycerin | 0 | 0 | 0 | 10 |
| Pentaerythritol | 10 | 9 | 11 | 0 |
| Acid Value (mgKOH/g) | 0.2 | 0.2 | 0.2 | 0.3 |
| Hydroxyl Value (mgKOH/g) | 1.6 | 1.6 | 0.8 | 1.5 |
| Melting Point (° C.) | 79 | 85 | 72 | 62 |

TABLE 5

| | Release Agent Dispersing Resins (Polyester Resins comprising Fatty Acid having Branched Structure) | | | | |
|---|---|---|---|---|---|
| | (c-4) | (c-5) | (c-6) | (c-7) | (c-8) |
| Terephthalic Acid | 29 | 30 | 29 | 29 | 29 |
| Isophthalic Acid | 0.4 | 0.4 | 0.4 | 0.4 | 0.4 |
| Trimellitic Anhydride | 7 | 8 | 7 | 7 | 7 |
| Ethylene Glycol | 8 | 10 | 8 | 8 | 8 |
| Polyoxypropylene(2.3)-2,2-bis(4-hydroxyphenyl)propane | 47 | 48 | 47 | 47 | 47 |
| Polyoxyethylene(2)-2,2-bis(4-hydroxyphenyl)propane | 7 | 0 | 7 | 7 | 7 |
| Ester Compound 1 | 2 | 4 | 0 | 0 | 0 |
| Ester Compound 2 | 0 | 0 | 2 | 0 | 0 |
| Ester Compound 3 | 0 | 0 | 0 | 2 | 0 |
| Ester Compound 4 | 0 | 0 | 0 | 0 | 2 |
| Weight Average Molecular Weight (Mw) | 28,000 | 34,000 | 43,000 | 38,000 | 31,000 |
| Number Average Molecular Weight (Mn) | 4,600 | 4,900 | 6,500 | 5,700 | 4,700 |
| Tg (° C.) | 55 | 52 | 60 | 48 | 42 |

The polyester resin (c-8) has a number average molecular weight (Mn) of 4,700 and a weight average molecular weight (Mw) of 31,000, and a glass transition temperature (Tg) of 42° C.

Compositions and properties of the above-prepared resins, i.e., the release agent dispersing resins are summarized in Tables 3 to 5.

TABLE 3

| | Release Agent Dispersing Resins (Graft Polymers) | | |
|---|---|---|---|
| | (c-1) | (c-2) | (c-3) |
| Low-molecular-weight Polyethylene | 100 | 150 | 0 |
| Low-molecular-weight Polypropylene | 0 | 0 | 200 |
| Styrene | 740 | 700 | 636 |
| Acrylonitrile | 100 | 95 | 70 |
| Butyl Acrylate | 60 | 55 | 88 |
| Acrylic Acid | 0 | 0 | 6 |
| Di-t-butylperoxyhexahydro-terephthalate | 36 | 36 | 30 |
| Weight Average Molecular Weight (Mw) | 24,000 | 16,000 | 11,000 |
| Number Average Molecular Weight (Mn) | 4,500 | 3,400 | 2,800 |
| Tg (° C.) | 67 | 63 | 58 |
| Solubility Parameter (cal/cm$^3$)$^{1/2}$ | 10.9 | 10.7 | 10.8 |

Preparation of Glycerin or Polyglycerin Esters (1)-(16)

In a reaction vessel, each combination of a glycerin and a fatty acid in amounts as described in Table 6 is subjected to an esterification reaction at 240° C. under nitrogen gas flow. Thus, glycerin or polyglycerin esters (1) to (16) are prepared. Properties of the glycerin or polyglycerin esters (1) to (16) are shown in Table 7. Raw material glycerins listed in Table 6, i.e., DIGLYCERIN S, POLYGLYCERIN #310, #500, and #750 (available from Sakamoto Yakuhin Kogyo Co., Ltd.) have an average polymerization degree of 2, 4, 6, and 10, respectively, which is calculated from the hydroxyl value. With respect to "Main Component" listed in Table 7, it is to be noted that the glycerin esters (1) and (2) each consist essentially of the listed glycerin esters while the polyglycerin esters (3) to (16) each comprise the listed glycerin esters only as main components because the raw material diglycerins and polyglycerins have a distribution in polymerization degree.

TABLE 6

|  | Glycerin | Fatty Acid | Molar ratio (Fatty Acid/Glycerin) |
|---|---|---|---|
| Glycerin Ester (1) | Purified Glycerin | Behenic Acid | 3/1 |
| Glycerin Ester (2) | Purified Glycerin | Stearic Acid | 3/1 |
| Polyglycerin Ester (3) | DIGLYCERIN S | Stearic Acid | 4/1 |
| Polyglycerin Ester (4) | DIGLYCERIN S | Behenic Acid | 4/1 |
| Polyglycerin Ester (5) | POLYGLYCERIN #310 | Palmitic Acid | 6/1 |
| Polyglycerin Ester (6) | POLYGLYCERIN #310 | Stearic Acid | 6/1 |
| Polyglycerin Ester (7) | POLYGLYCERIN #310 | Behenic Acid | 4/1 |
| Polyglycerin Ester (8) | POLYGLYCERIN #310 | Behenic Acid | 6/1 |
| Polyglycerin Ester (9) | POLYGLYCERIN #500 | Stearic Acid | 8/1 |
| Polyglycerin Ester (10) | POLYGLYCERIN #500 | Behenic Acid | 2/1 |
| Polyglycerin Ester (11) | POLYGLYCERIN #500 | Behenic Acid | 8/1 |
| Polyglycerin Ester (12) | POLYGLYCERIN #750 | Stearic Acid | 10/1 |
| Polyglycerin Ester (13) | POLYGLYCERIN #750 | Stearic Acid | 12/1 |
| Polyglycerin Ester (14) | POLYGLYCERIN #750 | Behenic Acid | 10/1 |
| Polyglycerin Ester (15) | POLYGLYCERIN #750 | Lignoceric Acid | 12/1 |
| Polyglycerin Ester (16) | Dodecaglycerin | Behenic Acid | 10/1 |

TABLE 7

|  | Main Component | Carbon Number of Fatty Acid | Average Polymerization Degree of Polyglycerin | Average Esterification Degree (%) | Melting Point (° C.) |
|---|---|---|---|---|---|
| Glycerin Ester (1) | Glycerin Tribehenate | 22 | — | 98 | 68 |
| Glycerin Ester (2) | Glycerin Tristearate | 18 | — | 98 | 55 |
| Polyglycerin Ester (3) | Diglycerin Tetrastearate | 18 | 2 | 97 | 58 |
| Polyglycerin Ester (4) | Diglycerin Tetrabehenate | 22 | 2 | 97 | 71 |
| Polyglycerin Ester (5) | Tetraglycerin Hexapalmitate | 16 | 4 | 96 | 52 |
| Polyglycerin Ester (6) | Tetraglycerin Hexastearate | 18 | 4 | 95 | 58 |
| Polyglycerin Ester (7) | Tetraglycerin Tetrabehenate | 22 | 4 | 66 | 71 |
| Polyglycerin Ester (8) | Tetraglycerin Hexabehenate | 22 | 4 | 95 | 66 |
| Polyglycerin Ester (9) | Hexaglycerin Octastearate | 18 | 6 | 96 | 57 |
| Polyglycerin Ester (10) | Hexaglycerin Dibehenate | 22 | 6 | 25 | 75 |
| Polyglycerin Ester (11) | Hexaglycerin Octabehenate | 22 | 6 | 93 | 70 |
| Polyglycerin Ester (12) | Decaglycerin Decastearate | 18 | 10 | 82 | 55 |
| Polyglycerin Ester (13) | Decaglycerin Dodecastearate | 18 | 10 | 96 | 56 |
| Polyglycerin Ester (14) | Decaglycerin Decabehenate | 22 | 10 | 83 | 70 |
| Polyglycerin Ester (15) | Decaglycerin Dodecalignocerate | 24 | 10 | 95 | 82 |
| Polyglycerin Ester (16) | Dodecaglycerin Decabehenate | 22 | 12 | 70 | 72 |

Toner Examples

Preparation of Aqueous Phase (1) to (26)

Aqueous phases (1) to (26) are prepared by mixing 83 parts of a water dispersion of each particulate second binder resin listed in Table 8 with 990 parts of water, 37 parts of a 48.5% aqueous solution of dodecyl diphenyl ether sodium disulfonate (ELEMINOL MON-7 from Sanyo Chemical Industries, Ltd.), and 90 parts of ethyl acetate.

TABLE 8

| Aqueous Phase No. | Second Binder Resin |
|---|---|
| (1) | (b-2) |
| (2) | (b-3) |
| (3) | (b-2) |
| (4) | (b-1) |
| (5) | (b-1) |
| (6) | — |
| (7) | (b-2) |
| (8) | (b-1) |
| (9) | (b-3) |

TABLE 8-continued

| Aqueous Phase No. | Second Binder Resin |
|---|---|
| (10) | — |
| (11) | (b-1) |
| (12) | (b-1) |
| (13) | (b-2) |
| (14) | — |
| (15) | (b-3) |
| (16) | — |
| (17) | (b-2) |
| (18) | (b-3) |
| (19) | (b-3) |
| (20) | (b-3) |
| (21) | (b-3) |
| (22) | (b-3) |
| (23) | (b-2) |
| (24) | (b-3) |
| (25) | (b-3) |
| (26) | (b-3) |

Preparation of Polyester Prepolymer

In a reaction vessel equipped with a condenser, a stirrer, and a nitrogen inlet pipe, 720 parts of ethylene oxide 2 mol adduct of bisphenol A, 90 parts of propylene oxide 2 mol adduct of bisphenol A, 290 parts of terephthalic acid, 25 parts of trimellitic anhydride, and 2 parts of dibutyltin oxide are subjected to a reaction for 8 hours at 230° C. under normal pressure and subsequent 7 hours under reduced pressures of 10 to 15 mmHg. Thus, an intermediate polyester resin is prepared.

The intermediate polyester resin has a number average molecular weight (Mn) of 2,500, a weight average molecular weight (Mw) of 10,700, a peak molecular weight of 3,400, a glass transition temperature (Tg) of 57° C., an acid value of 0.4 mgKOH/g, and a hydroxyl value of 49 mgKOH/g.

In another reaction vessel equipped with a condenser, a stirrer, and a nitrogen inlet pipe, 400 parts of the intermediate polyester resin, 95 parts of isophorone diisocyanate, and 500 parts of ethyl acetate are subjected to a reaction for 8 hours at 100° C. Thus, a 50% ethyl acetate solution of a polyester prepolymer is prepared. The prepolymer has a free isocyanate content of 1.42%.

Preparation of Ketimine Compound

In a reaction vessel equipped with a stirrer and a thermometer, 30 parts of isophoronediamine and 70 parts of methyl ethyl ketone are subjected to a reaction for 5 hours at 50° C. Thus, a ketimine compound is prepared. The ketimine compound has an amine value of 423 mgKOH/g.

Preparation of Master Batch (1)

First, 100 parts of the amorphous polyester resin (a-1), 100 parts of a carbon black (PRINTEX 35 from Degussa, having a DBP oil absorption of 42 ml/100 g and a pH of 9.5), and 50 parts of water are mixed by a HENSCHEL MIXER (from Mitsui Mining and Smelting Co., Ltd.).

The resulting mixture is kneaded for 30 minutes at 80° C. by double rolls, the kneaded mixture is then rolled and cooled, and the rolled mixture is then pulverized into particles by a pulverizer (available from Hosokawa Micron Corporation). Thus, a master batch (1) is prepared.

Preparation of Master Batches (2) to (11)

The procedure in preparation of the master batch (1) is repeated expect for replacing the amorphous polyester resin (a-1) with each amorphous polyester resin listed in Table 9. Thus, master batches (2) to (11) are prepared.

TABLE 9

| Master Batch No. | Amorphous Polyester Resin (First Binder Resin) |
|---|---|
| (1) | (a-1) |
| (2) | (a-2) |
| (3) | (a-3) |
| (4) | (a-4) |
| (5) | (a-5) |
| (6) | (a-6) |
| (7) | (a-7) |
| (8) | (a-8) |
| (9) | (a-9) |
| (10) | (a-10) |
| (11) | (d) |

Preparation of Release Agent Dispersions (1) to (26)

Each combination of a release agent, a first binder resin, a release agent dispersing agent, and ethyl acetate in amounts described in Table 10 is heated to above the melting point of the release agent while being agitated, and the resulting liquid is thereafter rapidly cooled to 0° C. The liquid is subjected to a dispersion treatment using a bead mill (ULTRAVISCOMILL (trademark) from Aimex Co., Ltd.) filled with 80% by volume of zirconia beads having a diameter of 0.5 mm, at a liquid feeding speed of 1 kg/hour and a disc peripheral speed of 6 msec. This dispersing operation is repeated 3 times (3 passes). Thus, release agent dispersions (1) to (26) are prepared.

TABLE 10

| Release Agent Dispersion | Release Agent | | First Binder Resin | | Release Agent Dispersing Resin | | Ethyl Acetate |
|---|---|---|---|---|---|---|---|
| (1) | Polyglycerin Ester (11) | 100 | (a-1) | 100 | (c-6) | 60 | 740 |
| (2) | Glycerin Ester (2) | 100 | (a-2) | 100 | (c-7) | 60 | 740 |
| (3) | Glycerin Ester (1) | 100 | (a-3) | 100 | (c-1) | 60 | 740 |
| (4) | Glycerin Ester (1) | 100 | (a-3) | 100 | (c-2) | 60 | 740 |
| (5) | Glycerin Ester (1) | 100 | (a-4) | 100 | (c-2) | 60 | 740 |
| (6) | Polyglycerin Ester (6) | 100 | (a-4) | 100 | (c-5) | 60 | 740 |
| (7) | Polyglycerin Ester (10) | 100 | (a-4) | 100 | (c-3) | 60 | 740 |
| (8) | Polyglycerin Ester (4) | 100 | (a-5) | 100 | (c-1) | 60 | 740 |
| (9) | Polyglycerin Ester (9) | 100 | (a-5) | 100 | (c-2) | 60 | 740 |
| (10) | Polyglycerin Ester (14) | 100 | (a-5) | 100 | (c-3) | 60 | 740 |
| (11) | Polyglycerin Ester (3) | 100 | (a-6) | 100 | (c-8) | 40 | 760 |
| (12) | Glycerin Ester (1) | 100 | (a-7) | 100 | (c-4) | 60 | 740 |
| (13) | Polyglycerin Ester (8) | 100 | (a-7) | 100 | (c-6) | 60 | 740 |
| (14) | Polyglycerin Ester (12) | 100 | (a-7) | 100 | (c-5) | 35 | 765 |
| (15) | Glycerin Ester (1) | 100 | (a-8) | 100 | (c-4) | 60 | 740 |

TABLE 10-continued

| Release Agent Dispersion | Release Agent | | First Binder Resin | | Release Agent Dispersing Resin | | Ethyl Acetate |
|---|---|---|---|---|---|---|---|
| (16) | Polyglycerin Ester (4) | 100 | (a-9) | 100 | (c-2) | 60 | 740 |
| (17) | Polyglycerin Ester (7) | 100 | (a-9) | 100 | (c-3) | 90 | 710 |
| (18) | Polyglycerin Ester (13) | 100 | (a-9) | 100 | (c-7) | 100 | 700 |
| (19) | Polyglycerin Ester (16) | 100 | (a-9) | 100 | (c-1) | 60 | 740 |
| (20) | Polyglycerin Ester (5) | 100 | (a-9) | 100 | (c-1) | 60 | 740 |
| (21) | Polyglycerin Ester (15) | 100 | (a-9) | 100 | (c-1) | 60 | 740 |
| (22) | Glycerin Ester (1) | 100 | (a-5) | 100 | — | — | 800 |
| (23) | Polyglycerin Ester (8) | 100 | (a-10) | 100 | (c-2) | 60 | 740 |
| (24) | Carnauba Wax | 100 | (a-4) | 100 | (c-1) | 60 | 740 |
| (25) | Paraffin Wax | 100 | (a-7) | 100 | (c-1) | 60 | 740 |
| (26) | Polyglycerin Ester (4) | 100 | (d) | 100 | (c-1) | 60 | 740 |

Preparation of Oily Phase (1) to (26)

Each combination of raw materials listed in Table 11 is subjected to a dispersion treatment using a bead mill (UL-TRAVISCOMILL (trademark) from Aimex Co., Ltd.) filled with 80% by volume of zirconia beads having a diameter of 0.5 mm, at a liquid feeding speed of 1 kg/hour and a disc peripheral speed of 6 msec. This dispersing operation is repeated 3 times (3 passes). Further, 2.5 parts of the ketimine compound are added to the resulting liquid. Thus, oily phases (1) to (26) are prepared.

TABLE 11

| Oily Phase No. | First Binder Resin | Prepolymer | Release Agent Dispersion | | Master Batch | | Ethyl Acetate |
|---|---|---|---|---|---|---|---|
| (1) | (a-1) | 62 | 22 | (1) | 80 | (1) | 12 | 60 |
| (2) | (a-2) | 86 | — | (2) | 30 | (2) | 12 | 108 |
| (3) | (a-3) | 69 | 24 | (3) | 50 | (3) | 12 | 81 |
| (4) | (a-3) | 62 | 22 | (4) | 80 | (3) | 12 | 60 |
| (5) | (a-4) | 62 | 22 | (5) | 80 | (4) | 12 | 60 |
| (6) | (a-4) | 45 | 20 | (6) | 150 | (4) | 12 | 9 |
| (7) | (a-4) | 62 | 22 | (7) | 80 | (4) | 12 | 60 |
| (8) | (a-5) | 73 | — | (8) | 80 | (5) | 12 | 71 |
| (9) | (a-5) | 73 | — | (9) | 80 | (5) | 12 | 71 |
| (10) | (a-5) | 62 | 22 | (10) | 80 | (5) | 12 | 60 |
| (11) | (a-6) | 75 | — | (11) | 80 | (6) | 12 | 69 |
| (12) | (a-7) | 62 | 22 | (12) | 80 | (7) | 12 | 60 |
| (13) | (a-7) | 62 | 22 | (13) | 80 | (7) | 12 | 60 |
| (14) | (a-7) | 75 | — | (14) | 80 | (7) | 12 | 69 |
| (15) | (a-8) | 62 | 22 | (15) | 80 | (8) | 12 | 60 |
| (16) | (a-9) | 52 | 22 | (16) | 120 | (9) | 12 | 30 |
| (17) | (a-9) | 60 | 22 | (17) | 80 | (9) | 12 | 62 |
| (18) | (a-9) | 59 | 22 | (18) | 80 | (9) | 12 | 63 |
| (19) | (a-9) | 73 | — | (19) | 80 | (9) | 12 | 71 |
| (20) | (a-9) | 73 | — | (20) | 80 | (9) | 12 | 71 |
| (21) | (a-9) | 73 | — | (21) | 80 | (9) | 12 | 71 |
| (22) | (a-5) | 66 | 24 | (22) | 80 | (5) | 12 | 54 |
| (23) | (a-10) | 73 | — | (23) | 80 | (10) | 12 | 71 |
| (24) | (a-4) | 62 | 22 | (24) | 80 | (4) | 12 | 60 |
| (25) | (a-7) | 62 | 22 | (25) | 80 | (7) | 12 | 60 |
| (26) | (d) | 62 | 22 | (26) | 80 | (11) | 12 | 60 |

Preparation of Mother Toners 1 to 26

In a vessel, 150 parts of the aqueous phase (1) are mixed and agitated with 100 parts of the oily phase (1) for 10 minutes by a TK HOMOMIXER (from PRIMIX Corporation) at a revolution of 12,000 rpm. Thus, an emulsion slurry is prepared.

A flask equipped with a stirrer and a thermometer is charged with 100 parts of the emulsion slurry. The emulsion slurry is agitated for 10 hours at 30° C. at a peripheral speed of 20 m/min so that the solvents are removed therefrom, followed by washing, filtering, and drying. The dried product is further sieved with a mesh having openings of 75 μm. Thus, a mother toner (1) is prepared.

The above procedure for preparing the mother toner (1) is repeated except for replacing the water phase (1) and the oily phase (1) with each of the water phases (2) to (26) and the oily phases (2) to (26), respectively. Thus, mother toners (2) to (26) are prepared.

Preparation of Toners (1) to (26)

Each of the mother toners (1) to (26) in an amount of 100 parts and a hydrophobized silica (H2000 available from Clariant Japan K.K.) in an amount of 1.0 part are mixed by a HENSCHEL MIXER (from Mitsui Mining and Smelting Co., Ltd.) at a peripheral speed of 30 m/sec for 30 minutes, followed by a pause for 1 minute. This mixing operation is repeated 5 times. The mixture is sieved with a mesh having openings of 35 μm. Thus, toners (1) to (26) are prepared.

Preparation of Carrier

A resin layer coating liquid is prepared by mixing 100 parts of a silicone resin (organo straight silicone), 5 parts of γ-(2-aminoethyl)aminopropyl trimethoxysilane, 10 parts of a carbon black, and 100 parts of toluene by a homomixer for 20 minutes.

The resin layer coating liquid is applied to the surfaces of 1,000 parts of ferrite particles having a volume average particle diameter of 35 μm using a fluidized bed coating device. Thus, a carrier is prepared.

Preparation of Developer

Each of the toners (1) to (26) in an amount of 5 parts and the carrier in an amount of 95 parts are mixed. Thus, developers (1) to (26) are prepared.

The above-prepared developers are subjected to the following evaluations.

Evaluations

Measurement of Volume Average Particle Diameter (Dv) and Number Average Particle Diameter (Dn)

As a measuring instrument, COULTER MULTISIZER III (available from Beckman Coulter Inc.) is used connecting to an interface (available from Nikkaki-Bios K.K.) and a personal computer for outputting number and volume distributions. As an electrolyte, 1% water solution of the first grade sodium chloride is prepared. In 100 to 150 mL of the electrolyte, 0.1 to 5 mL of a surfactant (alkylbenzene sulfonate) and 2 to 20 mg of each toner are dispersed by an ultrasonic disperser for about 1 to 3 minutes, thus obtaining a primary dispersion. In another beaker, 100 to 200 mL of the electrolyte is mixed with an amount of the primary dispersion, thus obtaining a measuring dispersion having a predetermined toner concentration. Thus, 50,000 toner particles in the measuring dispersion are subjected to a measurement of volume and number distributions by the COULTER MULTISIZER III equipped with an aperture of 100 μm. The volume average particle diameter (Dv) and number average particle diameter (Dn) are determined from the measured volume and number distributions, respectively.

Measurement of Dispersion Diameter of Release Agent

Each toner is embedded in an epoxy resin and cut into a ultrathin section having a thickness of about 100 nm. The ultrathin section is dyed with ruthenium tetraoxide and observed and photographed with a transmission electron microscope (TEM) at a magnification of 10,000. The photographed image is processed to determine the average longest diameter of the release agent in 50 toner particles.

Measurement of Melting Point of Release Agent

Melting point of each release agent is measured by a differential scanning calorimeter (DSC-60 from Shimadzu Corporation) as follows. First, 5.0 mg of each release agent is put in an aluminum container. The container is put on a holder unit and set in an electric furnace. The container is heated from 20° C. to 200° C. at a heating rate of 10° C./min under nitrogen atmosphere. The container is then cooled from 200° C. to 0° C. at a cooling rate of 10° C./min and heated again to 200° C. at a heating rate of 10° C./min, thus obtaining a DSC curve. The DSC curve is analyzed with an analysis program in the DSC-60 to determine an endothermic peak observed in the second heating. The melting point of the sample is determined from a temperature at which the endothermic peak is observed.

Evaluation of Fixability

An electrophotographic copier (MF-200 from Ricoh Co., Ltd.) employing a TEFLON® fixing roller is modified so that the temperature of the fixing roller is variable. Each developer is mounted on the copier, and a solid image having 0.85±0.1 mg/cm$^2$ of toner is formed on sheets of a normal paper TYPE 6200 (from Ricoh Co., Ltd.) and a thick paper <135> (from NBS Ricoh) while varying the temperature of the fixing roller to determine the maximum and minimum fixable temperatures. The maximum fixable temperature is a temperature above which hot offset occurs on the normal paper. The minimum fixable temperature is a temperature below which the residual rate of image density after rubbing the solid image falls below 70% on the thick paper. The maximum and minimum temperatures thus determined are graded as follows.

Maximum Fixable Temperatures
AA: not less than 190° C.
A: not less than 180° C. and less than 190° C.
B: not less than 170° C. and less than 180° C.
C: less than 170° C.

Minimum Fixable Temperatures
AA: less than 115° C.
A: not less than 115° C. and less than 125° C.
B: not less than 125° C. and less than 135° C.
C: not less than 135° C.

Evaluation of Heat-Resistant Storage Stability (Penetration)

Each toner is contained in a 50-mL glass vessel and left in a constant temperature chamber at 50° C. for 24 hours. After being cooled to 24° C., the toner is subjected to a penetration test (JIS K2235-1991) to determine a penetration (mm).

The measured penetrations are graded as follows. The greater the penetration, the better the heat-resistant storage stability. Toners having a penetration less than 5 mm are not suitable for practical use.

AA: not less than 25 mm
A: not less than 15 mm and less than 25 mm
B: not less than 5 mm and less than 15 mm
C: less than 5 mm Evaluation of Filming Resistance Each developer is mounted on a tandem full-color image forming apparatus (IMAGIO NEO 450 from Ricoh Co., Ltd.). An image chart having an image area occupancy of 20% is printed out while controlling the toner concentration so that the resulting image density becomes 1.4±0.2. An initial charge quantity A (μC/g) of the developer and a charge quantity B (μC/g) of the developer after printing 200,000th sheets are measured by a blow off method and the degree of decrease is calculated from the following equation: $[(A-B)/A] \times 100(\%)$.

When toner particles form their film on carrier particles in the developer, charging ability of the carrier particles deteriorate. The smaller the degree of decrease of charge quantity, the smaller the degree of toner film formation on carrier particles.

Filming resistance is evaluated by the degree of decrease in charge quantity and graded as follows.

AA: less than 15%
A: not less than 15% and less than 30%
B: not less than 30% and less than 50%
C: not less than 50%

Evaluation of Image Density

Each developer is mounted on a tandem full-color image forming apparatus (IMAGIO NEO 450 from Ricoh Co., Ltd.), and a solid image having 1.00±0.05 mg/cm$^2$ of toner is formed on a sheet of a paper TYPE 6000<70W> (from Ricoh Co., Ltd.) while setting the temperature of the fixing roller to 160±2° C. Six randomly-selected portions in the solid image are subjected to a measurement of image density using a spectrophotometer (938 spectrodensitometer from X-Rite). The measured image density values are averaged and graded as follows.

A: not less than 2.0
B: not less than 1.70 and less than 2.0
C: less than 1.70

Overall Evaluation

The above results are comprehensively evaluated as follows.

AA: Very good (3 or more "AA"s and no "B" and "C")
A: Good (2 or less "B"s and no "C")
B: Poor (3 or more "B"s and no "C")
C: Very poor (1 or more "C"s)

The evaluation results are shown in Tables 12-1, 12-2, 13-1, and 13-2. The toners (1) to (18) are examples and the toners (19) to (26) are comparative examples.

TABLE 12-1

| Toner No. | Dv (μm) | Dn (μm) | Dv/Dn | Release Agent Dispersion Diameter (μm) | Release Agent Dispersion State |
|---|---|---|---|---|---|
| (1) | 5.4 | 4.6 | 1.17 | 1.1 | Inner dispersion |
| (2) | 5.2 | 4.3 | 1.21 | 1.3 | Inner dispersion |
| (3) | 5.6 | 4.9 | 1.14 | 0.4 | Inner dispersion |
| (4) | 5.3 | 4.6 | 1.15 | 0.1 | Inner dispersion |
| (5) | 5.5 | 4.8 | 1.15 | 0.4 | Inner dispersion |
| (6) | 5.7 | 4.6 | 1.24 | 1.3 | Partially surface localization |
| (7) | 5.6 | 4.8 | 1.17 | 1.1 | Inner dispersion |
| (8) | 5.9 | 5.2 | 1.13 | 0.4 | Inner dispersion |
| (9) | 5.3 | 4.4 | 1.20 | 1.3 | Inner dispersion |
| (10) | 5.8 | 4.7 | 1.23 | 1.1 | Inner dispersion |
| (11) | 5.5 | 4.6 | 1.20 | 1.3 | Inner dispersion |
| (12) | 5.4 | 4.7 | 1.15 | 0.4 | Inner dispersion |
| (13) | 6.0 | 5.2 | 1.15 | 1.0 | Inner dispersion |
| (14) | 6.1 | 4.9 | 1.24 | 1.3 | Partially surface localization |
| (15) | 5.2 | 4.6 | 1.13 | 0.2 | Inner dispersion |
| (16) | 6.0 | 4.8 | 1.25 | 0.4 | Inner dispersion |
| (17) | 5.7 | 4.8 | 1.19 | 1.1 | Inner dispersion |
| (18) | 5.9 | 4.9 | 1.20 | 1.3 | Inner dispersion |

TABLE 12-2

| Toner No. | Fixability Minimum Fixable Temp. | Fixability Maximum Fixable Temp. | Heat-Resistant Storage Stability | Filming Resistance | Image Density | Overall Evaluation |
|---|---|---|---|---|---|---|
| (1) | AA | A | AA | A | A | A |
| (2) | AA | B | B | A | A | A |
| (3) | AA | AA | A | AA | A | AA |
| (4) | AA | B | A | AA | A | A |
| (5) | AA | AA | AA | AA | A | AA |
| (6) | A | AA | B | B | A | A |
| (7) | AA | A | AA | A | A | A |
| (8) | AA | AA | AA | AA | A | AA |
| (9) | AA | A | A | A | A | A |
| (10) | AA | A | B | A | A | A |
| (11) | A | AA | A | A | A | A |
| (12) | AA | AA | AA | AA | A | AA |
| (13) | AA | A | AA | AA | A | AA |
| (14) | A | A | B | B | A | A |
| (15) | AA | AA | AA | AA | A | AA |
| (16) | AA | AA | B | A | A | A |
| (17) | AA | A | AA | A | A | A |
| (18) | A | A | A | A | A | A |

TABLE 13-1

| Comparative Toner No. | Dv (μm) | Dn (μm) | Dv/Dn | Release Agent Dispersion Diameter (μm) | Release Agent Dispersion State |
|---|---|---|---|---|---|
| (19) | 5.6 | 4.7 | 1.19 | 1.1 | Inner dispersion |
| (20) | 5.5 | 4.5 | 1.22 | 1.8 | Inner dispersion |
| (21) | 5.3 | 4.5 | 1.18 | 1.0 | Inner dispersion |
| (22) | 5.5 | 4.4 | 1.25 | 0.4 | Surface localization |
| (23) | 5.9 | 4.1 | 1.44 | 1.0 | Partially surface localization |
| (24) | 5.6 | 4.4 | 1.27 | 2.0 | Surface localization |
| (25) | 5.4 | 4.3 | 1.26 | 2.2 | Surface localization |
| (26) | 5.5 | 4.8 | 1.15 | 0.4 | Inner dispersion |

TABLE 13-2

| Comparative Toner No. | Fixability Minimum Fixable Temp. | Fixability Maximum Fixable Temp. | Heat-Resistant Storage Stability | Filming Resistance | Image Density | Overall Evaluation |
|---|---|---|---|---|---|---|
| (19) | C | B | AA | A | A | C |
| (20) | AA | B | C | C | C | C |
| (21) | C | A | AA | AA | A | C |
| (22) | C | A | C | C | C | C |
| (23) | C | A | C | B | B | C |
| (24) | C | A | C | C | C | C |
| (25) | C | A | C | C | C | C |
| (26) | C | AA | AA | AA | A | C |

Additional modifications and variations in accordance with further embodiments of the present invention are possible in light of the above teachings. It is therefore to be understood that within the scope of the appended claims the invention may be practiced other than as specifically described herein.

What is claimed is:

1. A toner, comprising:
   a first binder resin, including:
   an amorphous polyester resin (a) having a polyhydroxycarboxylic acid skeleton in its main chain, the polyhydroxycarboxylic acid skeleton comprising optically-active monomers having an optical purity X of 80% by mole or less, the optical purity X being represented by the following formula:

$X(\% \text{ by mole}) = |X(L\text{-form}) - X(D\text{-form})|$ wherein X(L-form) and X(D-form) represent ratios (% by mole) of L-form and D-form optically-active monomers, respectively;
   a release agent, including:
   an ester of a fatty acid having an average carbon number of 18 to 24 with glycerin or a polyglycerin having an average polymerization degree of 2 to 10, the ester having a melting point of 55 to 80° C.;
   a release agent dispersing resin, wherein the release agent dispersing resin includes a polyester resin comprising a fatty acid ester having a branched structure comprising a fatty acid having a carbon number of 16 to 24 and a polyol having 3 or more valences; and
   a colorant.

2. The toner according to claim 1, wherein the amorphous polyester resin (a) has a weight average molecular weight (Mw) of 10,000 to 40,000.

3. The toner according to claim 1, wherein the ester is dispersed in the toner with a dispersion diameter of 0.2 to 1.0 μm.

4. The toner according to claim 1, wherein the fatty acid includes behenic acid.

5. The toner according to claim 1, wherein the release agent includes a glycerin ester or a diglycerin ester.

6. The toner according to claim 1, wherein a content of the release agent dispersing resin is 40 to 90 parts by weight based on 100 parts by weight of the release agent.

7. The toner according to claim 1, wherein the toner further comprising particles of a second binder resin (b), the particles being adhered to a surface of the toner.

8. The toner according to claim 1, wherein the amorphous polyester resin (a) includes a straight-chain polyester diol having the polyhydroxycarboxylic acid skeleton.

9. The toner according to claim 1, wherein the polyhydroxycarboxylic acid skeleton is obtained from a ring-opening polymerization of a mixture of L-lactide and D-lactide.

10. The toner according to claim 1, wherein the polyhydroxycarboxylic acid skeleton is obtained from a ring-opening polymerization of mesolactide.

11. The toner according to claim 1, wherein the toner is manufactured by a method including:
   dissolving or dispersing at least the first binder resin, the release agent, the release agent dispersing resin, and the colorant in an organic solvent to prepare an oily toner components liquid; and
   emulsifying the oily toner components liquid in an aqueous medium.

12. A developer, comprising the toner according to claim 1 and a carrier.

13. An image forming method, comprising:
   forming an electrostatic latent image on an electrostatic latent image bearing member;
   developing the electrostatic latent image into a toner image with the developer according to claim 12;
   transferring the toner image from the electrostatic latent image bearing member onto a recording medium; and
   fixing the toner image on the recording medium.

* * * * *